US 11,819,257 B2

United States Patent
O'Neil et al.

(10) Patent No.: US 11,819,257 B2
(45) Date of Patent: Nov. 21, 2023

(54) COMPOSITIONS, TREATMENT SYSTEMS AND METHODS FOR IMPROVED COOLING OF LIPID-RICH TISSUE

(71) Applicant: Zeltiq Aesthetics, Inc., Pleasanton, CA (US)

(72) Inventors: Michael P. O'Neil, Dublin, CA (US); Leonard C. DeBenedictis, Dublin, CA (US); George Frangineas, Jr., Fremont, CA (US)

(73) Assignee: Zeltiq Aesthetics, Inc., Pleasanton, CA (US)

( * ) Notice: Subject to any disclaimer, the term of this patent is extended or adjusted under 35 U.S.C. 154(b) by 281 days.

(21) Appl. No.: 17/143,163

(22) Filed: Jan. 7, 2021

(65) Prior Publication Data
US 2021/0282829 A1 Sep. 16, 2021

Related U.S. Application Data

(63) Continuation of application No. 15/833,329, filed on Dec. 6, 2017, now Pat. No. 10,912,599, which is a
(Continued)

(51) Int. Cl.
*A61B 18/02* (2006.01)
*A61F 7/00* (2006.01)
(Continued)

(52) U.S. Cl.
CPC .......... *A61B 18/02* (2013.01); *A61B 18/0206* (2013.01); *A61B 90/04* (2016.02);
(Continued)

(58) Field of Classification Search
CPC ..... A61B 18/02; A61B 18/0206; A61B 90/04; A61B 2090/0463; A61B 2018/00464;
(Continued)

(56) References Cited

U.S. PATENT DOCUMENTS 681,806 A 9/1901 Mignault et al.
889,810 A 6/1908 Robinson et al.
(Continued)

FOREIGN PATENT DOCUMENTS

AU 2011253768 6/2012
CA 2441489 3/2005
(Continued)

OTHER PUBLICATIONS

Aguilar et al., "Modeling Cryogenic Spray Temperature and Evaporation Rate Based on Single-Droplet Analysis," Eighth International Conference on Liquid Atomization and Spray Systems, Pasadena, CA, USA, Jul. 2000, 7 pages.
(Continued)

*Primary Examiner* — Thomas A Giuliani
(74) *Attorney, Agent, or Firm* — Mintz, Levin, Cohn, Ferris, Glovsky and Popeo, P.C.

(57) ABSTRACT

Compositions and formulations for use with devices and systems that enable tissue cooling, such as cryotherapy applications, for alteration and reduction of adipose tissue are described. Aspects of the technology are further directed to methods, compositions and devices that provide protection of non-targeted cells (e.g., non-lipid-rich cells) from freeze damage during dermatological and related aesthetic procedures that require sustained exposure to cold temperatures. Further aspects of the technology include systems for enhancing sustained and/or replenishing release of cryoprotectant to a treatment site prior to and during cooling applications.

14 Claims, 8 Drawing Sheets

Related U.S. Application Data continuation of application No. 14/610,807, filed on Jan. 30, 2015, now Pat. No. 9,861,421.

(60) Provisional application No. 61/943,250, filed on Feb. 21, 2014, provisional application No. 61/943,257, filed on Feb. 21, 2014, provisional application No. 61/934,549, filed on Jan. 31, 2014.

(51) Int. Cl.
| | |
|---|---|
| *A61H 1/00* | (2006.01) |
| *A61N 7/00* | (2006.01) |
| *A61K 31/045* | (2006.01) |
| *A61K 31/047* | (2006.01) |
| *A61B 90/00* | (2016.01) |
| *A61B 18/00* | (2006.01) |

(52) U.S. Cl.
CPC .............. *A61F 7/00* (2013.01); *A61F 7/007* (2013.01); *A61H 1/006* (2013.01); *A61H 1/008* (2013.01); *A61K 31/045* (2013.01); *A61K 31/047* (2013.01); *A61N 7/00* (2013.01); *A61B 2018/00291* (2013.01); *A61B 2018/00464* (2013.01); *A61B 2018/00714* (2013.01); *A61B 2018/00791* (2013.01); *A61B 2018/00875* (2013.01); *A61B 2018/00994* (2013.01); *A61B 2018/0237* (2013.01); *A61B 2018/0262* (2013.01); *A61B 2090/0463* (2016.02); *A61B 2090/065* (2016.02); *A61F 2007/0003* (2013.01); *A61F 2007/0004* (2013.01); *A61F 2007/0019* (2013.01); *A61F 2007/0036* (2013.01); *A61F 2007/0045* (2013.01); *A61F 2007/0047* (2013.01); *A61F 2007/0052* (2013.01); *A61F 2007/0056* (2013.01); *A61F 2007/0075* (2013.01); *A61F 2007/0087* (2013.01); *A61F 2007/0093* (2013.01); *A61F 2007/0096* (2013.01)

(58) Field of Classification Search
CPC .. A61B 2018/00994; A61B 2018/0237; A61B 2018/0262; A61F 7/00; A61F 2007/0052; A61F 2007/0056; A61F 2007/0075; A61N 7/00; A61K 31/045; A61K 31/047
USPC .......................... 606/20, 22, 23; 607/96, 104
See application file for complete search history.

(56) References Cited

U.S. PATENT DOCUMENTS

| | | |
|---|---|---|
| 1,093,868 A | 4/1914 | Leighty |
| 2,516,491 A | 7/1950 | Swastek |
| 2,521,780 A | 9/1950 | Dodd et al. |
| 2,726,658 A | 12/1955 | Chessey |
| 2,766,619 A | 10/1956 | Tribus et al. |
| 2,851,602 A | 9/1958 | Cramwinckel et al. |
| 3,093,135 A | 6/1963 | Hirschhorn |
| 3,132,688 A | 5/1964 | Nowak |
| 3,133,539 A | 5/1964 | William et al. |
| 3,282,267 A | 11/1966 | Eidus |
| 3,341,230 A | 9/1967 | Wichers |
| 3,502,080 A | 3/1970 | Hirschhorn |
| 3,566,871 A | 3/1971 | Richter et al. |
| 3,587,577 A | 6/1971 | Zubkov et al. |
| 3,591,645 A | 7/1971 | Selwitz |
| 3,692,338 A | 9/1972 | Didier |
| 3,703,897 A | 11/1972 | Mack et al. |
| 3,710,784 A | 1/1973 | Taylor |
| 3,786,814 A | 1/1974 | Armao |
| 3,827,436 A | 8/1974 | Andera et al. |
| 3,942,519 A | 3/1976 | Shock |
| 3,948,269 A | 4/1976 | Zimmer |
| 3,986,385 A | 10/1976 | Johnston et al. |
| 3,993,053 A | 11/1976 | Grossan |
| 4,002,221 A | 1/1977 | Buchalter |
| 4,008,910 A | 2/1977 | Roche |
| 4,026,299 A | 5/1977 | Sauder |
| 4,140,130 A | 2/1979 | Storm |
| 4,149,529 A | 4/1979 | Copeland et al. |
| 4,178,429 A | 12/1979 | Scheffer |
| 4,202,336 A | 5/1980 | Van Gerven |
| 4,266,043 A | 5/1981 | Fujii et al. |
| 4,269,068 A | 5/1981 | Molina |
| D260,173 S | 8/1981 | Wiebe |
| 4,381,009 A | 4/1983 | Del Bon |
| 4,396,011 A | 8/1983 | Mack et al. |
| 4,459,854 A | 7/1984 | Richardson et al. |
| 4,470,263 A | 9/1984 | Lehovec et al. |
| 4,483,341 A | 11/1984 | Witteles |
| 4,528,979 A | 7/1985 | Marchenko et al. |
| 4,531,524 A | 7/1985 | Mioduski |
| 4,548,212 A | 10/1985 | Leung |
| 4,555,313 A | 11/1985 | Duchane et al. |
| 4,585,002 A | 4/1986 | Kissin |
| 4,603,076 A | 7/1986 | Bowditch et al. |
| 4,614,191 A | 9/1986 | Perler et al. |
| 4,644,955 A | 2/1987 | Mioduski |
| 4,664,110 A | 5/1987 | Schanzlin |
| 4,700,701 A | 10/1987 | Montaldi |
| 4,718,429 A | 1/1988 | Smidt |
| 4,741,338 A | 5/1988 | Miyamae |
| 4,758,217 A | 7/1988 | Gueret |
| 4,764,463 A | 8/1988 | Mason et al. |
| 4,802,475 A | 2/1989 | Weshahy |
| 4,832,022 A | 5/1989 | Tjulkov et al. |
| 4,846,176 A | 7/1989 | Golden |
| 4,850,340 A | 7/1989 | Onishi |
| 4,869,250 A | 9/1989 | Bitterly |
| 4,880,564 A | 11/1989 | Abel et al. |
| 4,905,697 A | 3/1990 | Heggs et al. |
| 4,906,463 A | 3/1990 | Cleary et al. |
| 4,930,317 A | 6/1990 | Klein |
| 4,935,345 A | 6/1990 | Guilbeau et al. |
| 4,961,422 A | 10/1990 | Marchosky et al. |
| 4,962,761 A | 10/1990 | Golden |
| 4,990,144 A | 2/1991 | Blott et al. |
| 5,007,433 A | 4/1991 | Hermsdoerffer et al. |
| 5,018,521 A | 5/1991 | Campbell et al. |
| 5,024,650 A | 6/1991 | Hagiwara et al. |
| 5,065,752 A | 11/1991 | Sessions et al. |
| 5,069,208 A | 12/1991 | Noppel et al. |
| 5,084,671 A | 1/1992 | Miyata et al. |
| 5,108,390 A | 4/1992 | Potocky et al. |
| 5,119,674 A | 6/1992 | Nielsen |
| 5,139,496 A | 8/1992 | Hed |
| 5,143,063 A | 9/1992 | Fellner |
| 5,148,804 A | 9/1992 | Hill et al. |
| 5,158,070 A | 10/1992 | Dory |
| 5,160,312 A | 11/1992 | Voelkel |
| 5,169,384 A | 12/1992 | Bosniak et al. |
| 5,197,466 A | 3/1993 | Marchosky et al. |
| 5,207,674 A | 5/1993 | Hamilton |
| 5,209,227 A | 5/1993 | Deutsch |
| 5,221,726 A | 6/1993 | Dabi et al. |
| 5,264,234 A | 11/1993 | Windhab et al. |
| 5,277,030 A | 1/1994 | Miller |
| 5,314,423 A | 5/1994 | Seney et al. |
| 5,327,886 A | 7/1994 | Chiu |
| 5,330,745 A | 7/1994 | Mcdow et al. |
| 5,333,460 A | 8/1994 | Lewis et al. |
| 5,334,131 A | 8/1994 | Omandam et al. |
| 5,336,616 A | 8/1994 | Livesey et al. |
| 5,339,541 A | 8/1994 | Owens |
| 5,342,617 A | 8/1994 | Gold et al. |
| 5,351,677 A | 10/1994 | Kami et al. |
| 5,358,467 A | 10/1994 | Milstein et al. |
| 5,362,966 A | 11/1994 | Rosenthal et al. |
| 5,363,347 A | 11/1994 | Nguyen |
| 5,372,608 A | 12/1994 | Johnson |
| 5,386,837 A | 2/1995 | Sterzer |
| 5,411,541 A | 5/1995 | Bell et al. |

(56) References Cited

U.S. PATENT DOCUMENTS

| | | |
|---|---|---|
| 5,427,772 A | 6/1995 | Hagan et al. |
| 5,433,717 A | 7/1995 | Rubinsky et al. |
| D362,091 S | 9/1995 | Tomasiak et al. |
| 5,456,703 A | 10/1995 | Beeuwkes, III et al. |
| 5,472,416 A | 12/1995 | Blugerman et al. |
| 5,486,207 A | 1/1996 | Mahawili |
| 5,497,596 A | 3/1996 | Zatkulak |
| 5,501,655 A | 3/1996 | Rolt et al. |
| 5,505,726 A | 4/1996 | Meserol |
| 5,505,730 A | 4/1996 | Edwards et al. |
| 5,507,790 A | 4/1996 | Weiss |
| 5,514,105 A | 5/1996 | Goodman, Jr. et al. |
| 5,514,170 A | 5/1996 | Mauch |
| 5,516,505 A | 5/1996 | McDow |
| 5,531,742 A | 7/1996 | Barken |
| 5,558,376 A | 9/1996 | Woehl |
| 5,562,604 A | 10/1996 | Yablon et al. |
| 5,571,801 A | 11/1996 | Segall et al. |
| 5,575,812 A | 11/1996 | Owens et al. |
| 5,603,221 A | 2/1997 | Maytal |
| 5,628,769 A | 5/1997 | Saringer |
| 5,634,890 A | 6/1997 | Morris |
| 5,634,940 A | 6/1997 | Panyard |
| 5,647,051 A | 7/1997 | Neer |
| 5,647,868 A | 7/1997 | Chinn |
| 5,650,450 A | 7/1997 | Lovette et al. |
| 5,651,773 A | 7/1997 | Perry et al. |
| 5,654,279 A | 8/1997 | Rubinsky et al. |
| 5,654,546 A | 8/1997 | Lindsay et al. |
| 5,660,836 A | 8/1997 | Knowlton et al. |
| 5,665,053 A | 9/1997 | Jacobs |
| 5,672,172 A | 9/1997 | Zupkas |
| 5,700,284 A | 12/1997 | Owens et al. |
| 5,725,483 A | 3/1998 | Podolsky |
| 5,733,280 A | 3/1998 | Avitall |
| 5,741,248 A | 4/1998 | Stern et al. |
| 5,746,702 A | 5/1998 | Gelfgat et al. |
| 5,746,736 A | 5/1998 | Tankovich |
| 5,755,663 A | 5/1998 | Larsen et al. |
| 5,755,753 A | 5/1998 | Knowlton et al. |
| 5,755,755 A | 5/1998 | Panyard |
| 5,759,182 A | 6/1998 | Varney et al. |
| 5,759,764 A | 6/1998 | Polovina et al. |
| 5,764,794 A | 6/1998 | Perlin |
| 5,769,879 A | 6/1998 | Richards et al. |
| 5,785,955 A | 7/1998 | Fischer |
| 5,792,080 A | 8/1998 | Ookawa et al. |
| 5,800,490 A | 9/1998 | Patz et al. |
| 5,802,865 A | 9/1998 | Strauss |
| 5,814,040 A | 9/1998 | Nelson et al. |
| D399,493 S | 10/1998 | Nakajima et al. |
| 5,817,050 A | 10/1998 | Klein et al. |
| 5,817,145 A | 10/1998 | Augustine |
| 5,817,149 A | 10/1998 | Owens et al. |
| 5,817,150 A | 10/1998 | Owens et al. |
| 5,830,208 A | 11/1998 | Muller et al. |
| 5,833,685 A | 11/1998 | Tortal et al. |
| 5,844,013 A | 12/1998 | Kenndoff et al. |
| 5,853,364 A | 12/1998 | Baker et al. |
| 5,865,841 A | 2/1999 | Kolen et al. |
| 5,871,524 A | 2/1999 | Knowlton |
| 5,871,526 A | 2/1999 | Gibbs et al. |
| 5,885,211 A | 3/1999 | Eppstein et al. |
| 5,891,617 A | 4/1999 | Watson et al. |
| 5,895,418 A | 4/1999 | Saringer |
| 5,901,707 A | 5/1999 | Goncalves |
| 5,902,256 A | 5/1999 | Benaron |
| 5,919,219 A | 7/1999 | Knowlton et al. |
| 5,944,748 A | 8/1999 | Mager et al. |
| 5,948,011 A | 9/1999 | Knowlton et al. |
| 5,954,680 A | 9/1999 | Augustine et al. |
| 5,964,092 A | 10/1999 | Tozuka et al. |
| 5,964,749 A | 10/1999 | Eckhouse et al. |
| 5,967,976 A | 10/1999 | Larsen et al. |
| 5,980,561 A | 11/1999 | Kolen et al. |
| 5,986,167 A | 11/1999 | Arteman et al. |
| 5,989,286 A | 11/1999 | Owens et al. |
| 5,997,530 A | 12/1999 | Nelson et al. |
| 6,017,337 A | 1/2000 | Pira |
| 6,023,932 A | 2/2000 | Johnston |
| 6,031,525 A | 2/2000 | Perlin |
| 6,032,675 A | 3/2000 | Rubinsky |
| 6,039,694 A | 3/2000 | Larson et al. |
| 6,041,787 A | 3/2000 | Rubinsky |
| 6,047,215 A | 4/2000 | McClure et al. |
| 6,049,927 A | 4/2000 | Thomas et al. |
| 6,051,159 A | 4/2000 | Hao et al. |
| D424,699 S | 5/2000 | Allen |
| 6,071,239 A | 6/2000 | Cribbs et al. |
| 6,074,415 A | 6/2000 | Der Ovanesian |
| 6,093,230 A | 7/2000 | Johnson et al. |
| 6,102,885 A | 8/2000 | Bass |
| 6,104,952 A | 8/2000 | Tu et al. |
| 6,104,959 A | 8/2000 | Spertell et al. |
| 6,106,517 A | 8/2000 | Zupkas |
| 6,113,558 A | 9/2000 | Rosenschein et al. |
| 6,113,559 A | 9/2000 | Klopotek |
| 6,113,626 A | 9/2000 | Clifton et al. |
| 6,120,519 A | 9/2000 | Weber et al. |
| 6,139,544 A | 10/2000 | Mikus et al. |
| 6,139,545 A | 10/2000 | Utley et al. |
| 6,150,148 A | 11/2000 | Nanda et al. |
| 6,151,735 A | 11/2000 | Koby et al. |
| 6,152,952 A | 11/2000 | Owens et al. |
| 6,171,301 B1 | 1/2001 | Nelson et al. |
| 6,176,869 B1 | 1/2001 | Mason et al. |
| 6,180,867 B1 | 1/2001 | Hedengren et al. |
| 6,226,996 B1 | 5/2001 | Weber et al. |
| 6,241,753 B1 | 6/2001 | Knowlton |
| 6,264,649 B1 | 7/2001 | Whitcroft et al. |
| 6,273,884 B1 | 8/2001 | Altshuler et al. |
| 6,290,988 B1 | 9/2001 | Van Vilsteren et al. |
| 6,311,090 B1 | 10/2001 | Knowlton |
| 6,311,497 B1 | 11/2001 | Chung |
| 6,312,453 B1 | 11/2001 | Stefanile et al. |
| 6,350,276 B1 | 2/2002 | Knowlton |
| 6,354,297 B1 | 3/2002 | Eiseman |
| 6,357,907 B1 | 3/2002 | Cleveland et al. |
| 6,375,673 B1 | 4/2002 | Clifton et al. |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,401,722 B1 | 6/2002 | Krag |
| 6,405,090 B1 | 6/2002 | Knowlton |
| 6,413,255 B1 | 7/2002 | Stern |
| 6,425,912 B1 | 7/2002 | Knowlton |
| 6,426,445 B1 | 7/2002 | Young et al. |
| 6,430,446 B1 | 8/2002 | Knowlton |
| 6,430,956 B1 | 8/2002 | Haas et al. |
| 6,438,424 B1 | 8/2002 | Knowlton |
| 6,438,954 B1 | 8/2002 | Goetz et al. |
| 6,438,964 B1 | 8/2002 | Giblin |
| 6,453,202 B1 | 9/2002 | Knowlton |
| 6,458,888 B1 | 10/2002 | Hood et al. |
| 6,461,378 B1 | 10/2002 | Knowlton |
| 6,470,216 B1 | 10/2002 | Knowlton |
| 6,471,693 B1 | 10/2002 | Carroll et al. |
| 6,475,211 B2 | 11/2002 | Chess et al. |
| 6,478,811 B1 | 11/2002 | Dobak, III et al. |
| 6,494,844 B1 | 12/2002 | Van Bladel et al. |
| 6,497,721 B2 | 12/2002 | Ginsburg et al. |
| 6,508,831 B1 | 1/2003 | Kushnir |
| 6,514,244 B2 | 2/2003 | Pope et al. |
| 6,519,964 B2 | 2/2003 | Bieberich |
| 6,523,354 B1 | 2/2003 | Tolbert |
| D471,982 S | 3/2003 | Cheng |
| 6,527,765 B2 | 3/2003 | Kelman et al. |
| 6,527,798 B2 | 3/2003 | Ginsburg et al. |
| 6,544,248 B1 | 4/2003 | Bass |
| 6,547,811 B1 | 4/2003 | Becker et al. |
| 6,548,297 B1 | 4/2003 | Kuri-Harcuch et al. |
| 6,551,255 B2 | 4/2003 | Van Bladel et al. |

(56) References Cited

U.S. PATENT DOCUMENTS

| | | |
|---|---|---|
| 6,551,341 B2 | 4/2003 | Boylan et al. |
| 6,551,348 B1 | 4/2003 | Blalock et al. |
| 6,551,349 B2 | 4/2003 | Lasheras et al. |
| 6,569,189 B1 | 5/2003 | Augustine et al. |
| 6,585,652 B2 | 7/2003 | Lang et al. |
| 6,592,577 B2 | 7/2003 | Abboud et al. |
| 6,605,080 B1 | 8/2003 | Altshuler et al. |
| 6,607,498 B2 | 8/2003 | Eshel |
| 6,620,187 B2 | 9/2003 | Carson et al. |
| 6,620,188 B1 | 9/2003 | Ginsburg et al. |
| 6,620,189 B1 | 9/2003 | Machold et al. |
| 6,623,430 B1 | 9/2003 | Slayton et al. |
| 6,626,854 B2 | 9/2003 | Friedman et al. |
| 6,632,219 B1 | 10/2003 | Baranov et al. |
| 6,635,053 B1 | 10/2003 | Lalonde et al. |
| 6,643,535 B2 | 11/2003 | Damasco et al. |
| 6,645,162 B2 | 11/2003 | Friedman et al. |
| 6,645,229 B2 | 11/2003 | Matsumura et al. |
| 6,645,232 B2 | 11/2003 | Carson |
| 6,648,904 B2 | 11/2003 | Altshuler et al. |
| 6,656,208 B2 | 12/2003 | Grahn et al. |
| 6,660,027 B2 | 12/2003 | Gruszecki et al. |
| 6,662,054 B2 | 12/2003 | Kreindel et al. |
| 6,682,524 B1 | 1/2004 | Elbrecht et al. |
| 6,682,550 B2 | 1/2004 | Clifton et al. |
| 6,685,731 B2 | 2/2004 | Kushnir et al. |
| 6,694,170 B1 | 2/2004 | Mikus et al. |
| 6,695,874 B2 | 2/2004 | Machold et al. |
| 6,697,670 B2 | 2/2004 | Chornenky |
| 6,699,237 B2 | 3/2004 | Weber et al. |
| 6,699,266 B2 | 3/2004 | Lachenbruch et al. |
| 6,699,267 B2 | 3/2004 | Voorhees et al. |
| 6,718,785 B2 | 4/2004 | Bieberich |
| 6,741,895 B1 | 5/2004 | Gafni et al. |
| 6,743,222 B2 | 6/2004 | Durkin et al. |
| 6,746,474 B2 | 6/2004 | Saadat |
| 6,749,624 B2 | 6/2004 | Knowlton |
| 6,753,182 B1 | 6/2004 | Kadkade et al. |
| 6,764,493 B1 | 7/2004 | Weber et al. |
| 6,764,502 B2 | 7/2004 | Bieberich |
| 6,789,545 B2 | 9/2004 | Littrup et al. |
| 6,795,728 B2 | 9/2004 | Chornenky et al. |
| 6,820,961 B2 | 11/2004 | Johnson |
| 6,821,274 B2 | 11/2004 | McHale et al. |
| 6,840,955 B2 | 1/2005 | Ein |
| 6,849,075 B2 | 2/2005 | Bertolero et al. |
| 6,878,144 B2 | 4/2005 | Altshuler et al. |
| 6,889,090 B2 | 5/2005 | Kreindel |
| 6,892,099 B2 | 5/2005 | Jaafar et al. |
| 6,904,956 B2 | 6/2005 | Noel |
| 6,918,903 B2 | 7/2005 | Bass |
| 6,927,316 B1 | 8/2005 | Faries, Jr. et al. |
| 6,942,022 B2 | 9/2005 | Blangetti et al. |
| 6,945,942 B2 | 9/2005 | Van Bladel et al. |
| 6,948,903 B2 | 9/2005 | Ablabutyan et al. |
| 6,969,399 B2 | 11/2005 | Schock et al. |
| 7,005,558 B1 | 2/2006 | Johansson et al. |
| 7,006,874 B2 | 2/2006 | Knowlton et al. |
| 7,022,121 B2 | 4/2006 | Stern et al. |
| 7,037,326 B2 | 5/2006 | Lee |
| 7,054,685 B2 | 5/2006 | Dimmer et al. |
| 7,060,061 B2 | 6/2006 | Altshuler et al. |
| D525,592 S | 7/2006 | Nguyen |
| 7,077,858 B2 | 7/2006 | Fletcher et al. |
| 7,081,111 B2 | 7/2006 | Svaasand et al. |
| 7,083,612 B2 | 8/2006 | Littrup et al. |
| 7,096,204 B1 | 8/2006 | Chen et al. |
| 7,112,712 B1 | 9/2006 | Ancell |
| 7,115,123 B2 | 10/2006 | Knowlton et al. |
| 7,141,049 B2 | 11/2006 | Stern et al. |
| 7,183,360 B2 | 2/2007 | Daniel et al. |
| 7,189,252 B2 | 3/2007 | Krueger |
| 7,192,426 B2 | 3/2007 | Baust et al. |
| 7,204,832 B2 | 4/2007 | Altshuler et al. |
| 7,220,778 B2 | 5/2007 | Anderson et al. |
| 7,229,436 B2 | 6/2007 | Stern et al. |
| D546,949 S | 7/2007 | Green |
| 7,258,674 B2 | 8/2007 | Cribbs et al. |
| D550,362 S | 9/2007 | Olivera et al. |
| 7,267,675 B2 | 9/2007 | Stern et al. |
| 7,276,058 B2 | 10/2007 | Altshuler et al. |
| 7,318,821 B2 | 1/2008 | Lalonde et al. |
| 7,331,951 B2 | 2/2008 | Eshel et al. |
| 7,347,855 B2 | 3/2008 | Eshel et al. |
| D568,258 S | 5/2008 | Adam |
| 7,367,341 B2 | 5/2008 | Anderson et al. |
| 7,532,201 B2 | 5/2009 | Quistgaard et al. |
| 7,572,268 B2 | 8/2009 | Babaev |
| 7,604,632 B2 | 10/2009 | Howlett et al. |
| 7,613,523 B2 | 11/2009 | Eggers et al. |
| 7,615,016 B2 | 11/2009 | Barthe et al. |
| 7,713,266 B2 | 5/2010 | Elkins et al. |
| 7,780,656 B2 | 8/2010 | Tankovich |
| 7,799,018 B2 | 9/2010 | Goulko |
| 7,824,437 B1 | 11/2010 | Saunders |
| 7,828,831 B1 | 11/2010 | Tanhehco et al. |
| 7,850,683 B2 | 12/2010 | Elkins et al. |
| 7,854,754 B2 | 12/2010 | Ting et al. |
| 7,862,558 B2 | 1/2011 | Elkins et al. |
| RE42,277 E | 4/2011 | Jaafar et al. |
| 7,938,824 B2 | 5/2011 | Chornenky et al. |
| 7,959,657 B1 | 6/2011 | Harsy et al. |
| 7,963,959 B2 | 6/2011 | Da Silva et al. |
| 7,967,763 B2 | 6/2011 | Deem et al. |
| 7,993,330 B2 | 8/2011 | Goulko |
| 7,998,137 B2 | 8/2011 | Elkins et al. |
| RE42,835 E | 10/2011 | Chornenky et al. |
| RE43,009 E | 12/2011 | Chornenky et al. |
| 8,133,180 B2 | 3/2012 | Slayton et al. |
| 8,133,191 B2 | 3/2012 | Rosenberg et al. |
| 8,192,474 B2 | 6/2012 | Levinson |
| 8,246,611 B2 | 8/2012 | Paithankar et al. |
| 8,247,221 B2 | 8/2012 | Fawcett |
| 8,275,442 B2 | 9/2012 | Allison |
| 8,285,390 B2 | 10/2012 | Levinson et al. |
| 8,333,700 B1 | 12/2012 | Barthe et al. |
| 8,337,539 B2 | 12/2012 | Ting et al. |
| 8,366,622 B2 | 2/2013 | Slayton et al. |
| 8,372,130 B2 | 2/2013 | Young et al. |
| 8,387,631 B1 | 3/2013 | Thonghara et al. |
| 8,397,518 B1 | 3/2013 | Vistakula et al. |
| 8,414,631 B2 | 4/2013 | Quisenberry et al. |
| 8,433,400 B2 | 4/2013 | Prushinskaya et al. |
| 8,506,486 B2 | 8/2013 | Slayton et al. |
| 8,523,775 B2 | 9/2013 | Barthe et al. |
| 8,523,791 B2 | 9/2013 | Castel |
| 8,523,927 B2 | 9/2013 | Levinson et al. |
| 8,535,228 B2 | 9/2013 | Slayton et al. |
| 8,603,073 B2 | 12/2013 | Allison |
| 8,636,665 B2 | 1/2014 | Slayton et al. |
| 8,641,622 B2 | 2/2014 | Barthe et al. |
| 8,663,112 B2 | 3/2014 | Slayton et al. |
| 8,672,848 B2 | 3/2014 | Slayton et al. |
| 8,676,332 B2 | 3/2014 | Fahey |
| D702,848 S | 4/2014 | Mendoza et al. |
| 8,690,778 B2 | 4/2014 | Slayton et al. |
| 8,690,779 B2 | 4/2014 | Slayton et al. |
| 8,690,780 B2 | 4/2014 | Slayton et al. |
| 8,702,774 B2 | 4/2014 | Baker et al. |
| 8,758,215 B2 | 6/2014 | Legendre et al. |
| 8,764,693 B1 | 7/2014 | Graham et al. |
| 8,834,547 B2 | 9/2014 | Anderson et al. |
| 8,840,608 B2 | 9/2014 | Anderson et al. |
| 9,132,031 B2 | 9/2015 | Levinson et al. |
| 9,149,322 B2 | 10/2015 | Knowlton |
| 9,308,120 B2 | 4/2016 | Anderson et al. |
| 9,314,368 B2 | 4/2016 | Allison et al. |
| 9,358,149 B2 | 6/2016 | Anderson et al. |
| 9,375,345 B2 | 6/2016 | Levinson et al. |
| 9,408,745 B2 | 8/2016 | Levinson et al. |
| D777,338 S | 1/2017 | Coakley et al. |
| 9,545,523 B2 | 1/2017 | Nanda |
| 9,581,942 B1 | 2/2017 | Shippert |
| 9,649,220 B2 | 5/2017 | Anderson et al. |

(56) References Cited

U.S. PATENT DOCUMENTS

| | | |
|---|---|---|
| 9,655,770 B2 | 5/2017 | Levinson et al. |
| 9,737,434 B2 | 8/2017 | Allison |
| 9,752,856 B2 | 9/2017 | Rashad |
| 9,844,460 B2 | 12/2017 | Weber et al. |
| 9,844,461 B2 | 12/2017 | Levinson et al. |
| 9,855,166 B2 | 1/2018 | Anderson et al. |
| 9,861,421 B2 | 1/2018 | O'Neil et al. |
| 9,861,520 B2 | 1/2018 | Baker et al. |
| 10,092,346 B2 | 10/2018 | Levinson |
| 10,201,380 B2 | 2/2019 | DeBenedictis et al. |
| 10,292,859 B2 | 5/2019 | Levinson et al. |
| 10,383,787 B2 | 8/2019 | Rosen et al. |
| 10,524,956 B2 | 1/2020 | DeBenedictis et al. |
| 10,555,831 B2 | 2/2020 | Jimenez Lozano et al. |
| 10,568,759 B2 | 2/2020 | Yee et al. |
| 10,575,890 B2 | 3/2020 | DeBenedictis et al. |
| 10,675,176 B1 | 6/2020 | Coakley et al. |
| 10,765,552 B2 | 9/2020 | Root et al. |
| 10,806,500 B2 | 10/2020 | DeBenedictis et al. |
| 10,912,599 B2 | 2/2021 | O'Neil et al. |
| 10,952,891 B1 | 3/2021 | Yee et al. |
| D921,211 S | 6/2021 | Jeong et al. |
| D921,911 S | 6/2021 | Jeong et al. |
| 11,076,879 B2 | 8/2021 | Yee et al. |
| 11,452,634 B2 | 9/2022 | Baker et al. |
| 2001/0005791 A1 | 6/2001 | Ginsburg et al. |
| 2001/0007952 A1 | 7/2001 | Shimizu |
| 2001/0023364 A1 | 9/2001 | Ahn |
| 2001/0031459 A1 | 10/2001 | Fahy et al. |
| 2001/0039439 A1 | 11/2001 | Elkins et al. |
| 2001/0041886 A1 | 11/2001 | Durkin et al. |
| 2001/0045104 A1 | 11/2001 | Bailey, Sr. et al. |
| 2001/0047196 A1 | 11/2001 | Ginsburg et al. |
| 2002/0026226 A1 | 2/2002 | Ein |
| 2002/0032473 A1 | 3/2002 | Kushnir et al. |
| 2002/0042607 A1 | 4/2002 | Palmer et al. |
| 2002/0049483 A1 | 4/2002 | Knowlton |
| 2002/0058975 A1 | 5/2002 | Bieberich |
| 2002/0062142 A1 | 5/2002 | Knowlton |
| 2002/0068338 A1 | 6/2002 | Nanda et al. |
| 2002/0068874 A1 | 6/2002 | Zuckerwar et al. |
| 2002/0082668 A1 | 6/2002 | Ingman |
| 2002/0103520 A1 | 8/2002 | Latham |
| 2002/0107558 A1 | 8/2002 | Clifton et al. |
| 2002/0117293 A1 | 8/2002 | Campbell |
| 2002/0120315 A1 | 8/2002 | Furuno et al. |
| 2002/0128648 A1 | 9/2002 | Weber et al. |
| 2002/0151830 A1 | 10/2002 | Kahn |
| 2002/0151887 A1 | 10/2002 | Stern et al. |
| 2002/0156509 A1 | 10/2002 | Cheung |
| 2002/0161357 A1 | 10/2002 | Anderson et al. |
| 2002/0188286 A1 | 12/2002 | Quijano et al. |
| 2002/0198518 A1 | 12/2002 | Mikus et al. |
| 2003/0032900 A1 | 2/2003 | Ella |
| 2003/0044764 A1 | 3/2003 | Soane et al. |
| 2003/0055414 A1 | 3/2003 | Altshuler et al. |
| 2003/0062040 A1 | 4/2003 | Lurie et al. |
| 2003/0069618 A1 | 4/2003 | Smith, III et al. |
| 2003/0077326 A1 | 4/2003 | Newton et al. |
| 2003/0077329 A1 | 4/2003 | Kipp et al. |
| 2003/0079488 A1 | 5/2003 | Bieberich |
| 2003/0100936 A1 | 5/2003 | Altshuler et al. |
| 2003/0109908 A1 | 6/2003 | Lachenbruch et al. |
| 2003/0109910 A1 | 6/2003 | Lachenbruch et al. |
| 2003/0109911 A1 | 6/2003 | Lachenbruch et al. |
| 2003/0109912 A1 | 6/2003 | Joye et al. |
| 2003/0114885 A1 | 6/2003 | Nova et al. |
| 2003/0120268 A1 | 6/2003 | Bertolero et al. |
| 2003/0125649 A1 | 7/2003 | McIntosh et al. |
| 2003/0187488 A1 | 10/2003 | Kreindel et al. |
| 2003/0199226 A1 | 10/2003 | Sommer et al. |
| 2003/0199859 A1 | 10/2003 | Altshuler et al. |
| 2003/0220594 A1 | 11/2003 | Halvorson et al. |
| 2003/0220635 A1 | 11/2003 | Knowlton et al. |
| 2003/0220674 A1 | 11/2003 | Anderson et al. |
| 2003/0236487 A1 | 12/2003 | Knowlton |
| 2004/0002705 A1 | 1/2004 | Knowlton et al. |
| 2004/0006328 A1 | 1/2004 | Anderson |
| 2004/0009936 A1 | 1/2004 | Tang et al. |
| 2004/0024437 A1 | 2/2004 | Machold et al. |
| 2004/0030332 A1 | 2/2004 | Knowlton et al. |
| 2004/0034341 A1 | 2/2004 | Altshuler et al. |
| 2004/0039312 A1 | 2/2004 | Hillstead et al. |
| 2004/0044384 A1 | 3/2004 | Leber et al. |
| 2004/0049178 A1 | 3/2004 | Abboud et al. |
| 2004/0073079 A1 | 4/2004 | Altshuler et al. |
| 2004/0074629 A1 | 4/2004 | Noel |
| 2004/0077977 A1 | 4/2004 | Ella et al. |
| 2004/0082886 A1 | 4/2004 | Timpson |
| 2004/0093042 A1 | 5/2004 | Altshuler et al. |
| 2004/0104012 A1 | 6/2004 | Zhou et al. |
| 2004/0106867 A1 | 6/2004 | Eshel et al. |
| 2004/0116866 A1 | 6/2004 | Gorman et al. |
| 2004/0133251 A1 | 7/2004 | Altshuler et al. |
| 2004/0159109 A1 | 8/2004 | Harvie |
| 2004/0162596 A1 | 8/2004 | Altshuler et al. |
| 2004/0176667 A1 | 9/2004 | Mihai et al. |
| 2004/0186535 A1 | 9/2004 | Knowlton |
| 2004/0199226 A1 | 10/2004 | Shadduck |
| 2004/0206365 A1 | 10/2004 | Knowlton |
| 2004/0210214 A1 | 10/2004 | Knowlton |
| 2004/0210287 A1 | 10/2004 | Greene |
| 2004/0215294 A1 | 10/2004 | Littrup et al. |
| 2004/0249427 A1 | 12/2004 | Nabilsi et al. |
| 2004/0259855 A1 | 12/2004 | Anderson et al. |
| 2004/0260209 A1 | 12/2004 | Ella et al. |
| 2004/0260210 A1 | 12/2004 | Ella et al. |
| 2004/0260211 A1 | 12/2004 | Maalouf |
| 2004/0267339 A1 | 12/2004 | Yon et al. |
| 2005/0010197 A1 | 1/2005 | Lau et al. |
| 2005/0033957 A1 | 2/2005 | Enokida |
| 2005/0038422 A1 | 2/2005 | Maurice |
| 2005/0049526 A1 | 3/2005 | Baer |
| 2005/0049543 A1 | 3/2005 | Anderson et al. |
| 2005/0049661 A1 | 3/2005 | Koffroth |
| 2005/0113725 A1 | 5/2005 | Masuda |
| 2005/0143781 A1 | 6/2005 | Carbunaru et al. |
| 2005/0145372 A1 | 7/2005 | Noel |
| 2005/0149153 A1 | 7/2005 | Nakase et al. |
| 2005/0154314 A1 | 7/2005 | Quistgaard |
| 2005/0154431 A1 | 7/2005 | Quistgaard et al. |
| 2005/0159986 A1 | 7/2005 | Breeland et al. |
| 2005/0177075 A1 | 8/2005 | Meunier et al. |
| 2005/0182462 A1 | 8/2005 | Chornenky et al. |
| 2005/0187495 A1 | 8/2005 | Quistgaard et al. |
| 2005/0187597 A1 | 8/2005 | Vanderschuit |
| 2005/0203446 A1 | 9/2005 | Takashima |
| 2005/0215987 A1 | 9/2005 | Slatkine |
| 2005/0222565 A1 | 10/2005 | Manstein |
| 2005/0251117 A1 | 11/2005 | Anderson et al. |
| 2005/0251120 A1 | 11/2005 | Anderson et al. |
| 2005/0261753 A1 | 11/2005 | Littrup et al. |
| 2005/0277859 A1 | 12/2005 | Carlsmith et al. |
| 2005/0283144 A1 | 12/2005 | Shiono et al. |
| 2006/0030778 A1 | 2/2006 | Mendlein et al. |
| 2006/0035380 A1 | 2/2006 | Saint-Leger |
| 2006/0036300 A1 | 2/2006 | Kreindel |
| 2006/0041704 A1 | 2/2006 | Choi |
| 2006/0074313 A1 | 4/2006 | Slayton et al. |
| 2006/0079852 A1 | 4/2006 | Bubb et al. |
| 2006/0094988 A1 | 5/2006 | Tosaya et al. |
| 2006/0106836 A1 | 5/2006 | Masugi et al. |
| 2006/0111613 A1 | 5/2006 | Boutillette et al. |
| 2006/0122509 A1 | 6/2006 | Desilets |
| 2006/0188832 A1 | 8/2006 | McCarren |
| 2006/0189964 A1 | 8/2006 | Anderson et al. |
| 2006/0195168 A1 | 8/2006 | Dunbar et al. |
| 2006/0200063 A1 | 9/2006 | Munro et al. |
| 2006/0206040 A1 | 9/2006 | Greenberg et al. |
| 2006/0206110 A1 | 9/2006 | Knowlton et al. |
| 2006/0234899 A1 | 10/2006 | Nekmard et al. |
| 2006/0259102 A1 | 11/2006 | Slatkine |
| 2006/0265032 A1 | 11/2006 | Hennings et al. |
| 2006/0270745 A1 | 11/2006 | Hunt et al. |

(56) References Cited

U.S. PATENT DOCUMENTS

| | | |
|---|---|---|
| 2006/0293734 A1 | 12/2006 | Scott et al. |
| 2007/0010811 A1 | 1/2007 | Stern et al. |
| 2007/0010861 A1 | 1/2007 | Anderson et al. |
| 2007/0032561 A1 | 2/2007 | Lin et al. |
| 2007/0038156 A1 | 2/2007 | Rosenberg |
| 2007/0055156 A1 | 3/2007 | Desilets et al. |
| 2007/0055173 A1 | 3/2007 | DeLonzor et al. |
| 2007/0055179 A1 | 3/2007 | Deem et al. |
| 2007/0055180 A1 | 3/2007 | Deem et al. |
| 2007/0055181 A1 | 3/2007 | Deem et al. |
| 2007/0073367 A1 | 3/2007 | Jones et al. |
| 2007/0078502 A1 | 4/2007 | Weber et al. |
| 2007/0088413 A1 | 4/2007 | Weber et al. |
| 2007/0100398 A1 | 5/2007 | Sloan |
| 2007/0106342 A1 | 5/2007 | Schumann |
| 2007/0129441 A1 | 6/2007 | Koulen |
| 2007/0129714 A1 | 6/2007 | Elkins et al. |
| 2007/0135876 A1 | 6/2007 | Weber |
| 2007/0141265 A1 | 6/2007 | Thomson |
| 2007/0179482 A1 | 8/2007 | Anderson |
| 2007/0193278 A1 | 8/2007 | Polacek et al. |
| 2007/0198071 A1 | 8/2007 | Ting et al. |
| 2007/0219540 A1 | 9/2007 | Masotti et al. |
| 2007/0233226 A1 | 10/2007 | Kochamba et al. |
| 2007/0239062 A1 | 10/2007 | Chopra et al. |
| 2007/0239075 A1 | 10/2007 | Rosenberg et al. |
| 2007/0239150 A1 | 10/2007 | Zvuloni et al. |
| 2007/0249519 A1 | 10/2007 | Guha et al. |
| 2007/0255187 A1 | 11/2007 | Branch |
| 2007/0255274 A1 | 11/2007 | Stern et al. |
| 2007/0255362 A1* | 11/2007 | Levinson ............... A61F 7/10 607/96 |
| 2007/0265585 A1 | 11/2007 | Joshi et al. |
| 2007/0265614 A1 | 11/2007 | Stern et al. |
| 2007/0270925 A1 | 11/2007 | Levinson |
| 2007/0282249 A1 | 12/2007 | Quisenberry et al. |
| 2007/0282318 A1 | 12/2007 | Spooner et al. |
| 2008/0014627 A1 | 1/2008 | Merchant et al. |
| 2008/0046047 A1 | 2/2008 | Jacobs |
| 2008/0058784 A1 | 3/2008 | Manstein et al. |
| 2008/0077201 A1 | 3/2008 | Levinson et al. |
| 2008/0077202 A1 | 3/2008 | Levinson |
| 2008/0077211 A1 | 3/2008 | Levinson et al. |
| 2008/0097207 A1 | 4/2008 | Cai et al. |
| 2008/0114348 A1 | 5/2008 | Vancelette et al. |
| 2008/0139901 A1 | 6/2008 | Altshuler et al. |
| 2008/0140061 A1 | 6/2008 | Toubia et al. |
| 2008/0140371 A1 | 6/2008 | Warner |
| 2008/0154254 A1 | 6/2008 | Burger et al. |
| 2008/0160480 A1 | 7/2008 | Ruddle et al. |
| 2008/0161892 A1 | 7/2008 | Mercuro et al. |
| 2008/0183164 A1 | 7/2008 | Elkins et al. |
| 2008/0188915 A1 | 8/2008 | Mills et al. |
| 2008/0195036 A1 | 8/2008 | Merchant et al. |
| 2008/0208181 A1 | 8/2008 | Toubia et al. |
| 2008/0248554 A1 | 10/2008 | Merchant et al. |
| 2008/0269851 A1 | 10/2008 | Deem et al. |
| 2008/0287839 A1 | 11/2008 | Rosen et al. |
| 2008/0300529 A1 | 12/2008 | Reinstein |
| 2008/0312651 A1 | 12/2008 | Pope et al. |
| 2009/0012434 A1 | 1/2009 | Anderson |
| 2009/0018623 A1 | 1/2009 | Levinson et al. |
| 2009/0018624 A1 | 1/2009 | Levinson et al. |
| 2009/0018625 A1 | 1/2009 | Levinson et al. |
| 2009/0018626 A1 | 1/2009 | Levinson et al. |
| 2009/0018627 A1 | 1/2009 | Levinson et al. |
| 2009/0024023 A1 | 1/2009 | Welches et al. |
| 2009/0054882 A1 | 2/2009 | Hansen et al. |
| 2009/0076488 A1 | 3/2009 | Welches et al. |
| 2009/0112134 A1 | 4/2009 | Avni |
| 2009/0118684 A1 | 5/2009 | Da Silva et al. |
| 2009/0118722 A1 | 5/2009 | Ebbers et al. |
| 2009/0149929 A1 | 6/2009 | Levinson et al. |
| 2009/0149930 A1 | 6/2009 | Schenck |
| 2009/0171253 A1 | 7/2009 | Davenport |
| 2009/0171334 A1 | 7/2009 | Elkins et al. |
| 2009/0209886 A1 | 8/2009 | Tudico |
| 2009/0221938 A1 | 9/2009 | Rosenberg et al. |
| 2009/0226424 A1 | 9/2009 | Hsu |
| 2009/0276018 A1 | 11/2009 | Brader |
| 2009/0281464 A1 | 11/2009 | Cioanta et al. |
| 2009/0299234 A1 | 12/2009 | Cho et al. |
| 2009/0306749 A1 | 12/2009 | Mulindwa |
| 2009/0312676 A1 | 12/2009 | Rousso et al. |
| 2009/0312693 A1 | 12/2009 | Thapliyal et al. |
| 2009/0318851 A1 | 12/2009 | Schenck |
| 2009/0326621 A1 | 12/2009 | El-Galley |
| 2010/0015190 A1 | 1/2010 | Hassler |
| 2010/0028432 A1 | 2/2010 | Gasco |
| 2010/0028969 A1 | 2/2010 | Mueller et al. |
| 2010/0030306 A1 | 2/2010 | Edelman et al. |
| 2010/0036295 A1 | 2/2010 | Altshuler et al. |
| 2010/0042087 A1 | 2/2010 | Goldboss et al. |
| 2010/0047360 A1 | 2/2010 | Klaveness et al. |
| 2010/0049178 A1 | 2/2010 | Deem et al. |
| 2010/0081971 A1 | 4/2010 | Allison |
| 2010/0087806 A1 | 4/2010 | Da Silva et al. |
| 2010/0152824 A1 | 6/2010 | Allison |
| 2010/0168726 A1 | 7/2010 | Brookman |
| 2010/0179531 A1 | 7/2010 | Nebrigic et al. |
| 2010/0198064 A1 | 8/2010 | Perl et al. |
| 2010/0198204 A1 | 8/2010 | Rogers |
| 2010/0217349 A1 | 8/2010 | Fahey et al. |
| 2010/0217357 A1 | 8/2010 | Da Silva et al. |
| 2010/0241023 A1 | 9/2010 | Gilbert |
| 2010/0268220 A1 | 10/2010 | Johnson et al. |
| 2010/0280582 A1 | 11/2010 | Baker et al. |
| 2011/0009860 A1 | 1/2011 | Chornenky et al. |
| 2011/0040265 A1 | 2/2011 | Castel |
| 2011/0040299 A1 | 2/2011 | Kim et al. |
| 2011/0046523 A1 | 2/2011 | Altshuler et al. |
| 2011/0060323 A1 | 3/2011 | Baust et al. |
| 2011/0066083 A1 | 3/2011 | Tosaya et al. |
| 2011/0066216 A1 | 3/2011 | Ting et al. |
| 2011/0077557 A1 | 3/2011 | Wing et al. |
| 2011/0077723 A1 | 3/2011 | Parish et al. |
| 2011/0112405 A1 | 5/2011 | Barthe et al. |
| 2011/0112520 A1 | 5/2011 | Kreindel |
| 2011/0144631 A1 | 6/2011 | Elkins et al. |
| 2011/0152849 A1 | 6/2011 | Baust et al. |
| 2011/0172651 A1 | 7/2011 | Altshuler et al. |
| 2011/0189129 A1 | 8/2011 | Qiu et al. |
| 2011/0196395 A1 | 8/2011 | Maschke |
| 2011/0196438 A1 | 8/2011 | Mnozil et al. |
| 2011/0202048 A1 | 8/2011 | Nebrigic et al. |
| 2011/0238050 A1 | 9/2011 | Allison et al. |
| 2011/0238051 A1 | 9/2011 | Levinson et al. |
| 2011/0257642 A1 | 10/2011 | Griggs, III |
| 2011/0288537 A1 | 11/2011 | Halaka |
| 2011/0300079 A1* | 12/2011 | Martens ............... A61P 39/00 424/10.1 |
| 2011/0301585 A1 | 12/2011 | Goulko |
| 2011/0313411 A1 | 12/2011 | Anderson et al. |
| 2011/0313412 A1 | 12/2011 | Kim et al. |
| 2012/0010609 A1 | 1/2012 | Deem et al. |
| 2012/0016239 A1 | 1/2012 | Barthe et al. |
| 2012/0022518 A1 | 1/2012 | Levinson |
| 2012/0022622 A1 | 1/2012 | Johnson et al. |
| 2012/0035475 A1 | 2/2012 | Barthe et al. |
| 2012/0035476 A1 | 2/2012 | Barthe et al. |
| 2012/0041525 A1 | 2/2012 | Karni |
| 2012/0046547 A1 | 2/2012 | Barthe et al. |
| 2012/0053458 A1 | 3/2012 | Barthe et al. |
| 2012/0065629 A1 | 3/2012 | Elkins et al. |
| 2012/0083862 A1 | 4/2012 | Altshuler et al. |
| 2012/0089211 A1 | 4/2012 | Curtis et al. |
| 2012/0101549 A1 | 4/2012 | Schumann |
| 2012/0109041 A1 | 5/2012 | Munz |
| 2012/0158100 A1 | 6/2012 | Schomacker |
| 2012/0209363 A1 | 8/2012 | Williams, III et al. |
| 2012/0233736 A1 | 9/2012 | Tepper et al. |
| 2012/0238901 A1 | 9/2012 | Augustine |
| 2012/0239123 A1 | 9/2012 | Weber et al. |
| 2012/0253416 A1 | 10/2012 | Erez et al. |

(56) References Cited

U.S. PATENT DOCUMENTS

| | | |
|---|---|---|
| 2012/0259322 A1 | 10/2012 | Fourkas et al. |
| 2012/0277674 A1 | 11/2012 | Clark, III et al. |
| 2012/0303104 A1 | 11/2012 | Levy |
| 2012/0310232 A1 | 12/2012 | Erez |
| 2013/0018236 A1 | 1/2013 | Altshuler et al. |
| 2013/0019374 A1 | 1/2013 | Schwartz |
| 2013/0035680 A1 | 2/2013 | Ben-Haim et al. |
| 2013/0066309 A1 | 3/2013 | Levinson |
| 2013/0073017 A1 | 3/2013 | Liu et al. |
| 2013/0079684 A1 | 3/2013 | Rosen et al. |
| 2013/0116758 A1 | 5/2013 | Levinson et al. |
| 2013/0116759 A1 | 5/2013 | Levinson et al. |
| 2013/0150844 A1 | 6/2013 | Deem et al. |
| 2013/0158440 A1 | 6/2013 | Allison |
| 2013/0158636 A1 | 6/2013 | Ting et al. |
| 2013/0166003 A1 | 6/2013 | Johnson et al. |
| 2013/0185440 A1 | 7/2013 | Blau et al. |
| 2013/0190744 A1 | 7/2013 | Avram et al. |
| 2013/0238062 A1 | 9/2013 | Ron Edoute et al. |
| 2013/0245507 A1 | 9/2013 | Khorassani Zadeh |
| 2013/0253384 A1 | 9/2013 | Anderson et al. |
| 2013/0253493 A1 | 9/2013 | Anderson et al. |
| 2013/0253494 A1 | 9/2013 | Anderson et al. |
| 2013/0253495 A1 | 9/2013 | Anderson et al. |
| 2013/0253496 A1 | 9/2013 | Anderson et al. |
| 2013/0303904 A1 | 11/2013 | Barthe et al. |
| 2013/0303905 A1 | 11/2013 | Barthe et al. |
| 2013/0331914 A1 | 12/2013 | Lee et al. |
| 2014/0005759 A1 | 1/2014 | Fahey et al. |
| 2014/0005760 A1 | 1/2014 | Levinson et al. |
| 2014/0067025 A1 | 3/2014 | Levinson et al. |
| 2014/0142469 A1 | 5/2014 | Britva et al. |
| 2014/0163582 A1 | 6/2014 | Austen et al. |
| 2014/0200487 A1 | 7/2014 | Ramdas et al. |
| 2014/0200488 A1 | 7/2014 | Seo et al. |
| 2014/0222121 A1 | 8/2014 | Spence et al. |
| 2014/0228718 A1 | 8/2014 | Diller et al. |
| 2014/0277219 A1 | 9/2014 | Nanda |
| 2014/0277302 A1 | 9/2014 | Weber et al. |
| 2014/0277303 A1 | 9/2014 | Biser et al. |
| 2014/0303697 A1 | 10/2014 | Anderson et al. |
| 2014/0316393 A1 | 10/2014 | Levinson |
| 2015/0005760 A1 | 1/2015 | Poulsen |
| 2015/0141797 A1 | 5/2015 | Turnquist et al. |
| 2015/0209174 A1 | 7/2015 | Abreu |
| 2015/0216719 A1 | 8/2015 | DeBenedictis et al. |
| 2015/0216720 A1 | 8/2015 | DeBenedictis et al. |
| 2015/0216816 A1 | 8/2015 | O'Neil et al. |
| 2015/0223975 A1 | 8/2015 | Anderson et al. |
| 2015/0283022 A1 | 10/2015 | Lee et al. |
| 2015/0328077 A1 | 11/2015 | Levinson |
| 2015/0328478 A1 | 11/2015 | McDaniel |
| 2015/0335468 A1 | 11/2015 | Rose et al. |
| 2015/0342780 A1 | 12/2015 | Levinson et al. |
| 2016/0045755 A1 | 2/2016 | Chun et al. |
| 2016/0051308 A1 | 2/2016 | Pennybacker et al. |
| 2016/0051401 A1 | 2/2016 | Yee et al. |
| 2016/0089550 A1 | 3/2016 | DeBenedictis et al. |
| 2016/0135985 A1 | 5/2016 | Anderson |
| 2016/0143771 A1 | 5/2016 | Swyer et al. |
| 2016/0220849 A1 | 8/2016 | Knowlton |
| 2016/0296269 A1 | 10/2016 | Rubinsky et al. |
| 2016/0317346 A1 | 11/2016 | Kovach |
| 2016/0324684 A1 | 11/2016 | Levinson et al. |
| 2017/0007309 A1 | 1/2017 | DeBenedictis et al. |
| 2017/0065323 A1 | 3/2017 | Rosen et al. |
| 2017/0079833 A1 | 3/2017 | Frangineas, Jr. et al. |
| 2017/0105869 A1 | 4/2017 | Frangineas, Jr. et al. |
| 2017/0165105 A1 | 6/2017 | Anderson et al. |
| 2017/0196731 A1 | 7/2017 | DeBenedictis et al. |
| 2017/0224528 A1 | 8/2017 | Berg et al. |
| 2017/0239079 A1 | 8/2017 | Root et al. |
| 2017/0319378 A1 | 11/2017 | Anderson et al. |
| 2017/0325992 A1 | 11/2017 | DeBenedictis et al. |
| 2017/0325993 A1 | 11/2017 | Jimenez Lozano et al. |
| 2017/0326042 A1 | 11/2017 | Zeng et al. |
| 2017/0326346 A1 | 11/2017 | Jimenez Lozano et al. |
| 2018/0161197 A1 | 6/2018 | Baker et al. |
| 2018/0185081 A1 | 7/2018 | O'Neil et al. |
| 2018/0185189 A1 | 7/2018 | Weber et al. |
| 2018/0263677 A1 | 9/2018 | Hilton et al. |
| 2018/0271767 A1 | 9/2018 | Jimenez Lozano et al. |
| 2018/0310950 A1 | 11/2018 | Yee et al. |
| 2019/0000663 A1 | 1/2019 | Anderson et al. |
| 2019/0125424 A1 | 5/2019 | DeBenedictis et al. |
| 2019/0133642 A1 | 5/2019 | Ignon et al. |
| 2019/0142493 A1 | 5/2019 | Debenedictis et al. |
| 2019/0224042 A1 | 7/2019 | Ting et al. |
| 2019/0365595 A1 | 12/2019 | Rosen et al. |
| 2020/0038234 A1 | 2/2020 | Jimenez Lozano et al. |
| 2020/0069458 A1 | 3/2020 | Pham |
| 2020/0100935 A1 | 4/2020 | Debenedictis et al. |
| 2020/0138501 A1 | 5/2020 | DeBenedictis et al. |
| 2020/0155215 A1 | 5/2020 | Levinson et al. |
| 2020/0297526 A1 | 9/2020 | Yee et al. |
| 2022/0047315 A1 | 2/2022 | Baker et al. |

FOREIGN PATENT DOCUMENTS

| | | |
|---|---|---|
| CA | 2585214 | 10/2007 |
| CH | 333982 | 11/1958 |
| CN | 86200604 | 10/1987 |
| CN | 2514795 | 10/2002 |
| CN | 2514811 | 10/2002 |
| CN | 2617189 Y | 5/2004 |
| CN | 1511503 | 7/2004 |
| CN | 1520276 A | 8/2004 |
| CN | 1741777 | 3/2006 |
| CN | 1817990 | 8/2006 |
| CN | 2843367 | 12/2006 |
| CN | 2850584 | 12/2006 |
| CN | 2850585 | 12/2006 |
| CN | 200970265 | 11/2007 |
| CN | 101259329 | 9/2008 |
| CN | 101309657 | 11/2008 |
| CN | 101351167 A | 1/2009 |
| CN | 101489541 A | 7/2009 |
| CN | 101909603 A | 12/2010 |
| CN | 102026596 A | 4/2011 |
| CN | 104127279 A | 11/2014 |
| CN | 104394813 A | 3/2015 |
| CN | 105473087 A | 4/2016 |
| DE | 532976 | 9/1931 |
| DE | 2851602 | 6/1980 |
| DE | 4213584 | 11/1992 |
| DE | 4224595 | 1/1994 |
| DE | 4238291 | 5/1994 |
| DE | 4445627 | 6/1996 |
| DE | 19800416 | 7/1999 |
| EP | 263069 | 4/1988 |
| EP | 0397043 | 11/1990 |
| EP | 0406244 | 1/1991 |
| EP | 560309 | 9/1993 |
| EP | 0598824 | 6/1994 |
| EP | 1030611 | 8/2000 |
| EP | 1201266 | 5/2002 |
| EP | 1568395 | 8/2005 |
| EP | 2260801 | 12/2010 |
| EP | 2289598 | 3/2011 |
| EP | 2527005 | 11/2012 |
| EP | 2904986 A1 | 8/2015 |
| FR | 854937 | 4/1940 |
| FR | 2744358 | 8/1997 |
| FR | 2745935 | 9/1997 |
| FR | 2767476 | 2/1999 |
| FR | 2776920 | 10/1999 |
| FR | 2789893 | 8/2000 |
| FR | 2805989 | 9/2001 |
| GB | 387960 | 2/1933 |
| GB | 578157 A | 6/1946 |
| GB | 2120944 | 12/1983 |
| GB | 2202447 | 9/1988 |
| GB | 2248183 | 4/1992 |
| GB | 2263872 | 8/1993 |

(56) References Cited

FOREIGN PATENT DOCUMENTS

| | | |
|---|---|---|
| GB | 2286660 | 8/1995 |
| GB | 2323659 | 9/1998 |
| GB | 2565139 A | 2/2019 |
| JP | 58187454 | 11/1983 |
| JP | S6094113 | 6/1985 |
| JP | 62082977 | 4/1987 |
| JP | 63076895 | 4/1988 |
| JP | 01223961 | 9/1989 |
| JP | 03051964 | 3/1991 |
| JP | 03259975 | 11/1991 |
| JP | 04093597 | 3/1992 |
| JP | 06261933 | 9/1994 |
| JP | 07194666 | 8/1995 |
| JP | 07268274 | 10/1995 |
| JP | 09164163 | 6/1997 |
| JP | 10216169 | 8/1998 |
| JP | 10223961 | 8/1998 |
| JP | 2000503154 | 3/2000 |
| JP | 3065657 | 7/2000 |
| JP | 2001046416 | 2/2001 |
| JP | 2002125993 | 5/2002 |
| JP | 2002224051 | 8/2002 |
| JP | 2002282295 | 10/2002 |
| JP | 2002290397 | 10/2002 |
| JP | 2002543668 | 12/2002 |
| JP | 2003190201 | 7/2003 |
| JP | 2004013600 | 1/2004 |
| JP | 2004073812 | 3/2004 |
| JP | 2004159666 | 6/2004 |
| JP | 2005039790 | 2/2005 |
| JP | 2005065984 | 3/2005 |
| JP | 2005110755 | 4/2005 |
| JP | 2005509977 | 4/2005 |
| JP | 3655820 | 6/2005 |
| JP | 2005520608 | 7/2005 |
| JP | 2005237908 | 9/2005 |
| JP | 2005323716 | 11/2005 |
| JP | 2006026001 | 2/2006 |
| JP | 2006130055 | 5/2006 |
| JP | 2006520949 | 9/2006 |
| JP | 2007270459 | 10/2007 |
| JP | 2008532591 | 8/2008 |
| JP | 2009515232 | 4/2009 |
| JP | 2009189757 | 8/2009 |
| KR | 200173222 | 12/1999 |
| KR | 1020040094508 | 11/2004 |
| KR | 20090000258 | 1/2009 |
| KR | 1020130043299 | 4/2013 |
| KR | 1020140038165 | 3/2014 |
| RU | 2036667 | 6/1995 |
| SU | 532976 | 11/1978 |
| TW | 0476644 | 2/2002 |
| WO | 8503216 | 8/1985 |
| WO | 9114417 | 10/1991 |
| WO | 9300807 | 1/1993 |
| WO | 9404116 | 3/1994 |
| WO | 9623447 | 8/1996 |
| WO | 9626693 | 9/1996 |
| WO | 9636293 | 11/1996 |
| WO | 9637158 | 11/1996 |
| WO | 9704832 | 2/1997 |
| WO | 9705828 | 2/1997 |
| WO | 9722262 | 6/1997 |
| WO | 9724088 | 7/1997 |
| WO | 9725798 | 7/1997 |
| WO | 9748440 | 12/1997 |
| WO | 9829134 | 7/1998 |
| WO | 9831321 | 7/1998 |
| WO | 9841156 | 9/1998 |
| WO | 9841157 | 9/1998 |
| WO | 9909928 | 3/1999 |
| WO | 9916502 | 4/1999 |
| WO | 9938469 | 8/1999 |
| WO | 9949937 | 10/1999 |
| WO | 0044346 | 8/2000 |
| WO | 0044349 | 8/2000 |
| WO | 0065770 | 11/2000 |
| WO | 0067685 | 11/2000 |
| WO | 0100269 | 1/2001 |
| WO | 0113989 | 3/2001 |
| WO | 0114012 | 3/2001 |
| WO | 0134048 | 5/2001 |
| WO | 0205736 | 1/2002 |
| WO | 02102921 | 12/2002 |
| WO | 03007859 | 1/2003 |
| WO | 03078596 | 9/2003 |
| WO | 03079916 | 10/2003 |
| WO | 2004000098 | 12/2003 |
| WO | 2004080279 | 9/2004 |
| WO | 2004090939 | 10/2004 |
| WO | WO-2005/018433 A2 | 3/2005 |
| WO | WO-2005/023200 A2 | 3/2005 |
| WO | 2005033957 | 4/2005 |
| WO | 2005046540 | 5/2005 |
| WO | 2005060354 | 7/2005 |
| WO | 2005096979 | 10/2005 |
| WO | 2005112815 | 12/2005 |
| WO | 2006066226 | 6/2006 |
| WO | 2006094348 | 9/2006 |
| WO | 2006106836 | 10/2006 |
| WO | 2006116603 | 11/2006 |
| WO | 2006127467 | 11/2006 |
| WO | 2007012083 | 1/2007 |
| WO | 2007028975 | 3/2007 |
| WO | 2007041642 | 4/2007 |
| WO | 2007101039 | 9/2007 |
| WO | 2007127924 | 11/2007 |
| WO | 2007145421 | 12/2007 |
| WO | 2007145422 | 12/2007 |
| WO | 2008006018 | 1/2008 |
| WO | 2008039556 | 4/2008 |
| WO | 2008039557 | 4/2008 |
| WO | 2008055243 | 5/2008 |
| WO | 2008143678 | 11/2008 |
| WO | 2009011708 | 1/2009 |
| WO | 2009026471 | 2/2009 |
| WO | 2010077841 | 7/2010 |
| WO | 2010127315 | 11/2010 |
| WO | 2012012296 | 1/2012 |
| WO | 2012103242 | 8/2012 |
| WO | 2013013059 | 1/2013 |
| WO | 2013075006 | 5/2013 |
| WO | 2013075016 | 5/2013 |
| WO | 2013190337 | 12/2013 |
| WO | 2014151872 | 9/2014 |
| WO | 2014191263 | 12/2014 |
| WO | WO-2015/088368 A1 | 6/2015 |
| WO | 2015117001 | 8/2015 |
| WO | 2015117005 | 8/2015 |
| WO | 2015117026 | 8/2015 |
| WO | 2015117032 | 8/2015 |
| WO | 2015117036 | 8/2015 |
| WO | 2016028796 | 2/2016 |
| WO | 2016048721 | 3/2016 |

OTHER PUBLICATIONS

Al-Sakere, B. et al. "Tumor Ablation with Irreversible Electroporation," PLoS One, Issue 11, Nov. 2007, 8 pages.

Alster, T. et al., "Cellulite Treatment Using a Novel Combination Radiofrequency, Infrared Light, and Mechanical Tissue Manipulation Device," Journal of Cosmetic and Laser Therapy, vol. 7, 2005, pp. 81-85.

Ardevol, A. et al., "Cooling Rates of Tissue Samples During Freezing with Liquid Nitrogen," Journal of Biochemical and Biophysical Methods, vol. 27, 1993, pp. 77-86.

Arena, C. B. et al., "High-Frequency Irreversible Electroporation (H-FIRE) for Non-Thermal Ablation Without Muscle Contraction," BioMedical Engineering OnLine 2011, 10:102, Nov. 21, 2011, 21 pgs.

Becker, S. M. et al. "Local Temperature Rises Influence In Vivo Electroporation Pore Development: A Numerical Stratum Corneum

(56) References Cited

OTHER PUBLICATIONS

Lipid Phase Transition Model," Journal of Biomechanical Engineering, vol. 129, Oct. 2007, pp. 712-721.
Bohm, T. et al., "Saline-Enhanced Radiofrequency Ablation of Breast Tissue: an in Vitro Feasibility Study," Investigative Radiology, vol. 35 (3), 2000, pp. 149-157.
Bondei, E. et al., "Disorders of Subcutaneous Tissue (Cold Panniculitis)," Dermatology in General Medicine, Fourth Edition, vol. 1, Chapter 108, 1993, Section 16, pp. 1333-1334.
Burge, S.M. et al., "Hair Follicle Destruction and Regeneration in Guinea Pig Skin after Cutaneous Freeze Injury," Cryobiology, 27(2), 1990, pp. 153-163.
Coban, Y. K. et al., "Ischemia-Reperfusion Injury of Adipofascial Tissue: An Experimental Study Evaluating Early Histologic and Biochemical Alterations in Rats," Mediators of Inflammation, 2005, 5, pp. 304-308.
Del Pino, M. E. et al. "Effect of Controlled Volumetric Tissue Heating with Radiofrequency on Cellulite and the Subcutaneous Tissue of the Buttocks and Thighs," Journal of Drugs in Dermatology, vol. 5, Issue 8, Sep. 2006, pp. 714-722.
Donski, P. K. et al., "The Effects of Cooling no Experimental Free Flap Survival," British Journal of Plastic Surgery, vol. 33, 1980, pp. 353-360.
Duck, F. A., Physical Properties of Tissue, Academic Press Ltd., chapters 4 & 5, 1990, pp. 73-165.
Duncan, W. C. et al., "Cold Panniculitis," Archives of Dermatology, vol. 94, Issue 6, Dec. 1966, pp. 722-724.
Epstein, E. H. et al., "Popsicle Panniculitis," The New England Journal of Medicine, 282(17), Apr. 23, 1970, pp. 966-967.
Fournier, L. et al. "Lattice Model for the Kinetics of Rupture of Fluid Bilayer Membranes," Physical Review, vol. 67, 2003, pp. 051908-1-051908-11.
Gabriel, S. et al., "The Dielectric Properties Of Biological Tissues: II. Measurements in the Frequency Range 10 Hz to 20 GHz," Physics in Medicine and Biology, vol. 41, 1996, pp. 2251-2269.
Gage, A. "Current Progress in Cryosurgery," Cryobiology 25, 1988, pp. 483-486.
Gatto, H. "Effects of Thermal Shocks on Interleukin-1 Levels and Heat Shock Protein 72 (HSP72) Expression in Normal Human Keratinocytes," PubMed, Archives of Dermatological Research, vol. 284, Issue 7, 1992: pp. 414-417 [Abstract].
Hale, H. B. et al., "Influence of Chronic Heat Exposure and Prolonged Food Deprivation on Excretion of Magnesium, Phosphorus, Calcium, Hydrogen Ion & Ketones," Aerospace Medicine, vol. 39—No. 9, Sep. 1968, pp. 919-926.
Heller Page, E. et al., "Temperature-dependent skin disorders," Journal of the American Academy of Dermatology, vol. 18, No. 5, Pt 1, May 1988, pp. 1003-1019.
Hemmingsson, A. et al. "Attenuation in Human Muscle and Fat Tissue in Vivo and in Vitro," Acra Radiologica Diagnosis, vol. 23, No. 2, 1982, pp. 149-151.
Henry, F. et al., "Les Dermatoses Hivernales," Rev Med Liege, 54:11, 1999, pp. 864-866. [Abstract Attached].
Hernan, P. et al., "Study for the evaluation of the efficacy of Lipocryolysis (EEEL)", Nov. 30, 2011.
Hernan, R. P., "A Study to Evaluate the Action of Lipocryolysis", 33(3) CryoLellers, 2012, pp. 176-180.
Holland, DB. et al. "Cold shock induces the synthesis of stress proteins in human keratinocytes," PubMed Journal of Investigative Dermatology; 101(2): Aug. 1993, pp. 196-199.
Holman, W. L. et al., "Variation in Cryolesion Penetration Due to Probe Size and Tissue Thermal Conductivity," The Annals of Thoracic Surgery, vol. 53, 1992, pp. 123-126.
Hong, J.S. et al., "Patterns of Ice Formation in Normal and Malignant Breast Tissue," Cryobiology 31, 1994, pp. 109-120.
Huang et al. "Comparative Proteomic Profiling of Murine Skin," Journal of Investigative Dermatology, vol. 121(1), Jul. 2003, pp. 51-64.

Isambert, H. "Understanding the Electroporation of Cells and Artificial Bilayer Membranes," Physical Review Letters, vol. 80, No. 15, 1998, pp. 3404-3707.
Jalian, H. R. et al., "Cryolipolysis: A Historical Perspective and Current Clinical Practice", 32(1) Semin. Cutan. Med. Surg., 2013, pp. 31-34.
Kellum, R. E. et al., "Sclerema Neonatorum: Report of Case and Analysis of Subcutaneous and Epidermal-Dermal Lipids by Chromatographic Methods," Archives of Dermatology, vol. 97, Apr. 1968, pp. 372-380.
Koska, J. et al., "Endocrine Regulation of Subcutaneous Fat Metabolism During Cold Exposure in Humans," Annals of the New York Academy of Sciences, vol. 967, 2002, pp. 500-505.
Kundu, S. K. et al., "Breath Acetone Analyzer: Diagnostic Tool to Monitor Dietary Fat Loss," Clinical Chemistry, vol. 39, Issue (1), 1993, pp. 87-92.
Kundu, S. K. et al., "Novel Solid-Phase Assay of Ketone Bodies in Urine," Clinical Chemistry, vol. 37, Issue (9), 1991, pp. 1565-1569.
Kuroda, S. et al. "Thermal Distribution of Radio-Frequency Inductive Hyperthermia Using an Inductive Aperture-Type Applicator: Evaluation of the Effect of Tumor Size and Depth", Medical and Biological Engineering and Computing, vol. 37, 1999, pp. 285-290.
Laugier, P. et al., "In Vivo Results with a New Device for Ultrasonic Monitoring of Pig Skin Cryosurgery: The Echographic Cryprobe," The Society for Investigative Dermatology, Inc., vol. 111, No. 2, Aug. 1998, pp. 314-319.
Levchenko et al., "Effect of Dehydration on Lipid Metabolism" Ukrainskii Biokhimicheskii Zhurnal, vol. 50, Issue 1, 1978, pp. 95-97.
Lidagoster, MD et al., "Comparison of Autologous Fat Transfer in Fresh, Refrigerated, and Frozen Specimens: An Animal Model," Annals of Plastic Surgery, vol. 44, No. 5, May 2000, pp. 512-515.
Liu, A. Y.-C. et al., "Transient Cold Shock Induces the Heat Shock Response upon Recovery at 37 C in Human Cells," Journal of Biological Chemistry, , 269(20), May 20, 1994, pp. 14768-14775.
L'Vova, S.P. "Lipid Levels and Lipid Peroxidation in Frog Tissues During Hypothermia and Hibernation" Ukrainskii Biokhimicheskii Zhurnal, vol. 62, Issue 1, 1990, pp. 65-70.
Maize, J.C. "Panniculitis," Cutaneous Pathology, Chapter 13, 1998, 327-344.
Malcolm, G. T. et al., "Fatty Acid Composition of Adipose Tissue in Humans: Differences between Subcutaneous Sites," The American Journal of Clinical Nutrition, vol. 50, 1989, pp. 288-291.
Manstein, D. et al. "A Novel Cryotherapy Method of Non-invasive, Selective Lipolysis," LasersSurg.Med 40:S20, 2008, p. 104.
Manstein, D. et al. "Selective Cryolysis: A Novel Method of Non-Invasive Fat Removal," Lasers in Surgery and Medicine: The Official Journal of the ASLMS, vol. 40, No. 9, Nov. 2008, pp. 595-604.
Mayoral, "Case Reports: Skin Tightening with a Combined Unipolar and Bipolar Radiofrequency Device," Journal of Drugs in Dermatology, 2007, pp. 212-215.
Mazur, P. "Cryobiology: The Freezing of Biological Systems," Science, 68, 1970, pp. 939-949.
Merrill, T. "A Chill to the Heart: A System to Deliver Local Hypothermia Could One Day Improve the Lives of Heart-Attack Patients," Mechanical Engineering Magazine, Oct. 2010, 10 pages.
Miklavcic, D. et al. "Electroporation-Based Technologies and Treatments," The Journal of Membrane Biology (2010) 236:1-2, 2 pgs.
Moschella, S. L. et al., "Diseases of the Subcutaneous Tissue," in Dermatology, Second Edition, vol. 2, 1985 Chapter 19, Section II (W.B. Saunders Company, 1980) pp. 1169-1181.
Murphy, J. V. et al., "Frostbite: Pathogenesis and Treatment" The Journal of Trauma: Injury, Infection, and Critical Care, vol. 48, No. 1, Jan. 2000, pp. 171-178.
Nagao, T. et al., "Dietary Diacylglycerol Suppresses Accumulation of Body Fat Compared to Triacylglycerol in Men a Double-Blind Controlled Trial," The Journal of Nutrition, vol. 130, Issue (4), 2000, pp. 792-797.
Nagle, W. A. et al., "Cultured Chinese Hamster Cells Undergo Apoptosis After Exposure to Cold but Nonfreezing Temperatures," Cryobiology 27, 1990, pp. 439-451.

(56) References Cited

OTHER PUBLICATIONS

Nagore, E. et al., "Lipoatrophia Semicircularis—a Traumatic Panniculitis: Report of Seven Cases and Review of the Literature," Journal of the American Academy of Dermatology, vol. 39, Nov. 1998, pp. 879-881.
Nanda, G.S. et al., "Studies on electroporation of thermally and chemically treated human erythrocytes," Bioelectrochemistry and Bioenergetics, 34, 1994, pp. 129-134, 6 pgs.
Narins, D.J. et al. "Non-Surgical Radiofrequency Facelift", The Journal of Drugs in Dermatology, vol. 2, Issue 5, 2003, pp. 495-500.
Nielsen, B. "Thermoregulation in Rest and Exercise," Acta Physiologica Scandinavica Supplementum, vol. 323 (Copenhagen 1969), pp. 7-74.
Nishikawa, H. et al. "Ultrastructural Changes and Lipid Peroxidation in Rat Adipomusculocutaneous Flap Isotransplants after Normothermic Storage and Reperfusion," Transplantation, vol. 54, No. 5, 1992, pp. 795-801.
Nurnberger, F. "So-Called Cellulite: An Invented Disease," Journal of Dermatologic Surgery and Oncology, Mar. 1978, pp. 221-229.
Pease, G. R. et al., "An Integrated Probe for Magnetic Resonance Imaging Monitored Skin Cryosurgery," Journal of Biomedical Engineering, vol. 117, Feb. 1995, pp. 59-63.
Pech, P. et al., "Attenuation Values, Volume Changes and Artifacts in Tissue Due to Freezing," Acta Radiologica, vol. 28, Issue 6, 1987, pp. 779-782.
Peterson, L. J. et al., "Bilateral Fat Necrosis of the Scrotum," Journal of Urology, vol. 116, 1976, pp. 825-826.
Phinney, S. D. et al., "Human Subcutaneous Adipose Tissue Shows Site-Specific Differences in Fatty Acid Composition," The American Journal of Clinical Nutrition, vol. 60, 1994, pp. 725-729.
Pierard, G.E. et al., "Cellulite: From Standing Fat Herniation to Hypodermal Stretch Marks," The American Journal of Dermatology, vol. 22, Issue 1, 2000, pp. 34-37, [Abstract].
Pope, K. et al. "Selective Fibrous Septae Heating: An Additional Mechanism of Action for Capacitively Coupled Monopolar Radiofrequency" Thermage, Inc. Article, Feb. 2005, 6pgs.
Quinn, P. J. "A Lipid-Phase Separation Model of Low-Temperature Damage to Biological Membranes," Cryobiology, 22, 1985, 128-146.
Rabi, T. et al., "Metabolic Adaptations in Brown Adipose Tissue of the Hamster in Extreme Ambient Temperatures," American Journal of Physiology, vol. 231, Issue 1, Jul. 1976, pp. 153-160.
Renold, A.E. et al. "Adipose Tissue" in Handbook of Physiology, Chapter 15, (Washington, D.C., 1965) pp. 169-176.
Rossi, A. B. R. et al. "Cellulite: a Review," European Academy of Dermatology and Venercology, 2000, pp. 251-262, 12 pgs.
Rubinsky, B. "Principles of Low Temperature Cell Preservation," Heart Failure Reviews, vol. 8, 2003, pp. 277-284.
Rubinsky, B. et al., "Cryosurgery: Advances in the Application of low Temperatures to Medicine," International Journal of Refrigeration, vol. 14, Jul. 1991, pp. 190-199.
Saleh, K.Y. et al., "Two-Dimensional Ultrasound Phased Array Design for Tissue Ablation for Treatment of Benign Prostatic Hyperplasia," International Journal of Hyperthermia, vol. 20, No. 1, Feb. 2004, pp. 7-31.
Schoning, P. et al., "Experimental Frostbite: Freezing Times, Rewarming Times, and Lowest Temperatures of Pig Skin Exposed to Chilled Air," Cryobiology 27, 1990, pp. 189-193.
Shephard, R. J. "Adaptation to Exercise in the Cold," Sports Medicine, vol. 2, 1985, pp. 59-71.
Sigma-Aldrich "Poly(ethylene glycol) and Poly(ethylene oxide)," http://www.sigmaaldrich.com/materials-science/materialscience-;products.htmi?TablePage=2020411 0, accessed Oct. 19, 2012.
Smalls, L. K. et al. "Quantitative Model of Cellulite: Three-Dimensional Skin Surface Topography, Biophysical Characterization, and Relationship to Human Perception," International Journal of Cosmetic Science, vol. 27, Issue 5, Oct. 2005, 17 pgs.
Thermage, News Release, "Study Published in Facial Plastic Surgery Journal Finds Selective Heating of Fibrous Septae Key to Success and Safety of Thermage ThermaCool System," Jun. 20, 2005, 2 pages.
"ThermaCool Monopolar Capacitive Radiofrequency, The one choice for nonablative tissue tightening and contouring", Thermage, Inc. Tech Brochure, Nov. 30, 2005, 8 pgs.
Vallerand et al. "Cold Stress Increases Lipolysis, FFA Ra and TG/FFA Cycling in Humans," Aviation, Space, and Environmental Medicine 70(1), 1999, pp. 42-50.
Wang, X. et al., "Cryopreservation of Cell/Hydrogel Constructs Based on a new Cell-Assembling Technique," Sep. 5, 2009, 40 pages.
Wharton, D. A. et al., "Cold Acclimation and Cryoprotectants in a Freeze-Tolerant Antarctic Nematode, Panagrolaimus Davidi,", Journal of Comparative Physiology, vol. 170, No. 4, Mar. 2000, 2 pages.
Winkler, C. et al., "Gene Transfer in Laboratory Fish: Model Organisms for the Analysis of Gene Function," in Transgenic Animals, Generation and Use (The Netherlands 1997), pp. 387-395.
Young, H. E. et al. "Isolation of Embryonic Chick Myosatellite and Pluripotent Stem Cells" The Journal of Tissue Culture Methods, vol. 14, Issue 2, 1992, pp. 85-92.
Zelickson, B. et al., "Cryolipolysis for Noninvasive Fat Cell Destruction: Initial Results from a Pig Model", 35 Dermatol. Sug., 2009, pp. 1-9.
Zouboulis, C. C. et al., "Current Developments and Uses of Cryosurgery in the Treatment of Keloids and Hypertrophic Scars," Wound Repair and Regeneration, vol. 10, No. 2, 2002, pp. 98-102.
International Search Report and Written Opinion of International Application No. PCT/US2015/013912; dated Jun. 5, 2015; 14 pages.
Beise, R.D. et al. (Jan. 1, 1998). "Psychophysical study of stinging pain evoked by brief freezing of superficial skin and ensuing short-lasting changes in sensations of cool and cold pain." Pain, vol. 74, Jan. 1, 1998 (Jan. 1, 1998), pp. 275-286, XP055620108, DOI: 10.1016/S0304-3959(97)00179-6.
Cohen, ML. (1977). "Measurement of The Thermal Properties of Human Skin. A review." J. Invest. Dermatol., 69, pp. 333-338.
Disclosure re: "Method and Apparatus for Regional Fat Reduction Using Controlled and Sustained Cooling of Skin Surface." Oct. 12, 2006. 7 pages.
Gao, D. (1991). "A Study of Physical and Biological Mechanisms of Cryoinjury and Cryoprotection of Human Erythrocytes in Freezing Preservation" Department of Mechanical Engineering Thesis, Concordia University, Mar. 1991. 253 pages.
Golstein, P. et al. (2007). "Cell death by necrosis: Towards a molecular definition." Trends Biochem Sci. 32:1 37-43.
Groenendaal, et al. (2010). Quantifying the Composition of Human Skin for Glucose Sensor Development, Journal of Diabetes Science and Technology, vol. 4, Issue 5, Sep. 2010, pp. 1032-1040.
Jimenez Lozano, J.N. et al. (2013). "Effect of Fibrous Septa in Radiofrequency Heating of Cutaneous and Subcutaneous Tissues: Computational Study," Lasers in Surgery and Medicine, 45 (5), pp. 326-338.
Karch, J. et al. (2015). "Regulated Necrotic Cell Death." Circulation Research, 116: 1800-1809.
Ribeiro, A.S. et al. (2015). "Main Benefits and Applicability of Plant Extracts in Skin Care Products." Cosmetics 2(2): 48-65. cosmetics2020048.
Rock, K. L. et al. (2008). "The Inflammatory Response to Cell Death" Annual Review Pathology 3:1, 99-126.
Schmidt, B. A., et al., "Intradermal adipocytes mediate fibroblast recruitment during skin wound healing," (2013) Development (Cambridge), 140 (7), pp. 1517-1527.

* cited by examiner

COMPOSITIONS, TREATMENT SYSTEMS AND METHODS FOR IMPROVED COOLING OF LIPID-RICH TISSUE

CROSS-REFERENCE TO RELATED APPLICATIONS

This application is continuation of U.S. patent application Ser. No. 15/833,329, filed Dec. 6, 2017 (U.S. Pat. No. 10,912,599), which is a continuation of U.S. application Ser. No. 14/610,807, filed Jan. 30, 2015 (U.S. Pat. No. 9,861, 421), which claims priority to U.S. Provisional Patent Application No. 61/934,549, filed Jan. 31, 2014, entitled "COMPOSITIONS, TREATMENT SYSTEMS AND METHODS FOR IMPROVED COOLING OF LIPID-RICH TISSUE," U.S. Provisional Patent Application No. 61/943,250, filed Feb. 21, 2014, entitled "TREATMENT SYSTEMS, METHODS, AND APPARATUSES FOR IMPROVING THE APPEARANCE OF SKIN;" and U.S. Provisional Patent Application No. 61/943,257, filed Feb. 21, 2014, entitled "TREATMENT SYSTEMS, METHODS AND APPARATUS FOR REDUCING SKIN IRREGULARITIES CAUSED BY CELLULITE," which are all incorporated herein by reference in their entireties.

INCORPORATION BY REFERENCE OF COMMONLY-OWNED APPLICATIONS AND PATENTS

The following commonly assigned U.S. patent applications and U.S. patents are incorporated herein by reference in their entirety:

U.S. Patent Publication No. 2008/0287839 entitled "METHOD OF ENHANCED REMOVAL OF HEAT FROM SUBCUTANEOUS LIPID-RICH CELLS AND TREATMENT APPARATUS HAVING AN ACTUATOR";

U.S. Pat. No. 6,032,675 entitled "FREEZING METHOD FOR CONTROLLED REMOVAL OF FATTY TISSUE BY LIPOSUCTION";

U.S. Patent Publication No. 2007/0255362 entitled "CRYOPROTECTANT FOR USE WITH A TREATMENT DEVICE FOR IMPROVED COOLING OF SUBCUTANEOUS LIPID-RICH CELLS";

U.S. Pat. No. 7,854,754 entitled "COOLING DEVICE FOR REMOVING HEAT FROM SUBCUTANEOUS LIPID-RICH CELLS";

U.S. Patent Publication No. 2011/0066216 entitled "COOLING DEVICE FOR REMOVING HEAT FROM SUBCUTANEOUS LIPID-RICH CELLS";

U.S. Patent Publication No. 2008/0077201 entitled "COOLING DEVICES WITH FLEXIBLE SENSORS";

U.S. Patent Publication No. 2008/0077211 entitled "COOLING DEVICE HAVING A PLURALITY OF CONTROLLABLE COOLING ELEMENTS TO PROVIDE A PREDETERMINED COOLING PROFILE";

U.S. Patent Publication No. 2009/0118722, filed Oct. 31, 2007, entitled "METHOD AND APPARATUS FOR COOLING SUBCUTANEOUS LIPID-RICH CELLS OR TISSUE";

U.S. Patent Publication No. 2009/0018624 entitled "LIMITING USE OF DISPOSABLE SYSTEM PATIENT PROTECTION DEVICES";

U.S. Patent Publication No. 2009/0018623 entitled "SYSTEM FOR TREATING LIPID-RICH REGIONS";

U.S. Patent Publication No. 2009/0018625 entitled "MANAGING SYSTEM TEMPERATURE TO REMOVE HEAT FROM LIPID-RICH REGIONS";

U.S. Patent Publication No. 2009/0018627 entitled "SECURE SYSTEM FOR REMOVING HEAT FROM LIPID-RICH REGIONS";

U.S. Patent Publication No. 2009/0018626 entitled "USER INTERFACES FOR A SYSTEM THAT REMOVES HEAT FROM LIPID-RICH REGIONS";

U.S. Pat. No. 6,041,787 entitled "USE OF CRYOPROTECTIVE AGENT COMPOUNDS DURING CRYOSURGERY";

U.S. Pat. No. 8,285,390 entitled "MONITORING THE COOLING OF SUBCUTANEOUS LIPID-RICH CELLS, SUCH AS THE COOLING OF ADIPOSE TISSUE";

U.S. Provisional Patent Application Ser. No. 60/941,567 entitled "METHODS, APPARATUSES AND SYSTEMS FOR COOLING THE SKIN AND SUBCUTANEOUS TISSUE";

U.S. Pat. No. 8,275,442 entitled "TREATMENT PLANNING SYSTEMS AND METHODS FOR BODY CONTOURING APPLICATIONS";

U.S. patent application Ser. No. 12/275,002 entitled "APPARATUS WITH HYDROPHILIC RESERVOIRS FOR COOLING SUBCUTANEOUS LIPID-RICH CELLS";

U.S. patent application Ser. No. 12/275,014 entitled "APPARATUS WITH HYDROPHOBIC FILTERS FOR REMOVING HEAT FROM SUBCUTANEOUS LIPID-RICH CELLS";

U.S. Patent Publication No. 2010/0152824 entitled "SYSTEMS AND METHODS WITH INTERRUPT/RESUME CAPABILITIES FOR COOLING SUBCUTANEOUS LIPID-RICH CELLS";

U.S. Pat. No. 8,192,474 entitled "TISSUE TREATMENT METHODS";

U.S. Patent Publication No. 2010/0280582 entitled "DEVICE, SYSTEM AND METHOD FOR REMOVING HEAT FROM SUBCUTANEOUS LIPID-RICH CELLS";

U.S. Patent Publication No. 2012/0022518 entitled "COMBINED MODALITY TREATMENT SYSTEMS, METHODS AND APPARATUS FOR BODY CONTOURING APPLICATIONS";

U.S. Publication No. 2011/0238050 entitled "HOME-USE APPLICATORS FOR NON-INVASIVELY REMOVING HEAT FROM SUBCUTANEOUS LIPID-RICH CELLS VIA PHASE CHANGE COOLANTS, AND ASSOCIATED DEVICES, SYSTEMS AND METHODS";

U.S. Publication No. 2011/0238051 entitled "HOME-USE APPLICATORS FOR NON-INVASIVELY REMOVING HEAT FROM SUBCUTANEOUS LIPID-RICH CELLS VIA PHASE CHANGE COOLANTS, AND ASSOCIATED DEVICES, SYSTEMS AND METHODS";

U.S. Publication No. 2012/0239123 entitled "DEVICES, APPLICATION SYSTEMS AND METHODS WITH LOCALIZED HEAT FLUX ZONES FOR REMOVING HEAT FROM SUBCUTANEOUS LIPID-RICH CELLS";

U.S. patent application Ser. No. 13/830,413 entitled "MULTI-MODALITY TREATMENT SYSTEMS, METHODS AND APPARATUS FOR ALTERING SUBCUTANEOUS LIPID-RICH TISSUE"; and U.S. patent application Ser. No. 13/830,027 entitled "TREATMENT SYSTEMS WITH FLUID MIXING SYSTEMS AND FLUID-COOLED APPLICATORS AND METHODS OF USING THE SAME".

U.S. Patent Publication Nos. 2005/0251120 and 2008/0077211, and U.S. Pat. No. 8,285,390 are attached hereto as an Appendix, the entireties of which are hereby incorporated by reference herein and made a part of this application.

TECHNICAL FIELD

The present disclosure relates generally to treatment devices, systems, and methods for removing heat from subcutaneous lipid-rich tissue. In particular, several embodiments are directed to cryoprotectant compositions, treatment systems and methods for improved cooling of targeted tissue.

BACKGROUND

Excess body fat, or adipose tissue, may be present in various locations of the body, including, for example, the thigh, buttocks, abdomen, knees, back, face, arms, and other areas. Excess adipose tissue can detract from personal appearance and athletic performance. Moreover, excess adipose tissue is thought to magnify the unattractive appearance of cellulite, which forms when subcutaneous fat lobules protrude or penetrate into the dermis and create dimples where the skin is attached to underlying structural fibrous strands. Cellulite and excessive amounts of adipose tissue are often considered to be cosmetically unappealing. Moreover, significant health risks may be associated with higher amounts of excess body fat.

Aesthetic improvement of the human body often involves the selective removal of adipose tissue. Removal of excess adipose tissue has been reported to have health benefits in addition to cosmetic enhancements. Currently, the most common procedures for this purpose are invasive, such as liposuction or other surgical techniques. Invasive procedures, however, tend to be associated with high cost, long recovery times, and increased risk of complications. In many instances, non-invasive or minimally invasive procedures can allow some or all of these disadvantages to be avoided while providing at least comparable clinical outcomes as those of invasive procedures. For example, non-invasive removal of excess subcutaneous adipose tissue can eliminate both unnecessary recovery time and discomfort associated with invasive procedures such as liposuction. Conventional non-invasive treatments for removing excess body fat typically include topical agents, weight-loss drugs, regular exercise, dieting, or a combination of these treatments. One drawback of these treatments is that they may not be effective or even possible under certain circumstances. For example, when a person is physically injured or ill, regular exercise may not be an option. Similarly, weight-loss drugs or topical agents are not an option if, as another example, they cause an allergic or negative reaction. Furthermore, fat loss in selective areas of a person's body often cannot be achieved using general or systemic weight-loss methods.

Other methods designed to reduce subcutaneous adipose tissue include laser-assisted liposuction and mesotherapy. Newer non-invasive methods include applying radiant energy to subcutaneous lipid-rich cells via, e.g., radio frequency and/or light energy, such as described in U.S. Patent Publication No. 2006/0036300 and U.S. Pat. No. 5,143,063, or via, e.g., high intensity focused ultrasound (HIFU) radiation such as described in U.S. Pat. Nos. 7,258,674 and 7,347,855. Additional methods and devices for non-invasively reducing subcutaneous adipose tissue by cooling are disclosed in U.S. Pat. No. 7,367,341 entitled "METHODS AND DEVICES FOR SELECTIVE DISRUPTION OF FATTY TISSUE BY CONTROLLED COOLING" to Anderson et al. and U.S. Patent Publication No. 2005/0251120 entitled "METHODS AND DEVICES FOR DETECTION AND CONTROL OF SELECTIVE DISRUPTION OF FATTY TISSUE BY CONTROLLED COOLING" to Anderson et al., the entire disclosures of which are incorporated herein by reference.

BRIEF DESCRIPTION OF THE DRAWINGS

In the drawings, identical reference numbers identify similar elements or acts. The sizes and relative positions of elements in the drawings are not necessarily drawn to scale. For example, the shapes of various elements and angles may not be drawn to scale, and some of these elements are arbitrarily enlarged and positioned to improve drawing legibility. Further, the particular shapes of the elements as drawn are not intended to convey any information regarding the actual shape of the particular elements, and have been solely selected for ease of recognition in the drawings.

DETAILED DESCRIPTION

A. Overview

Figure 1:
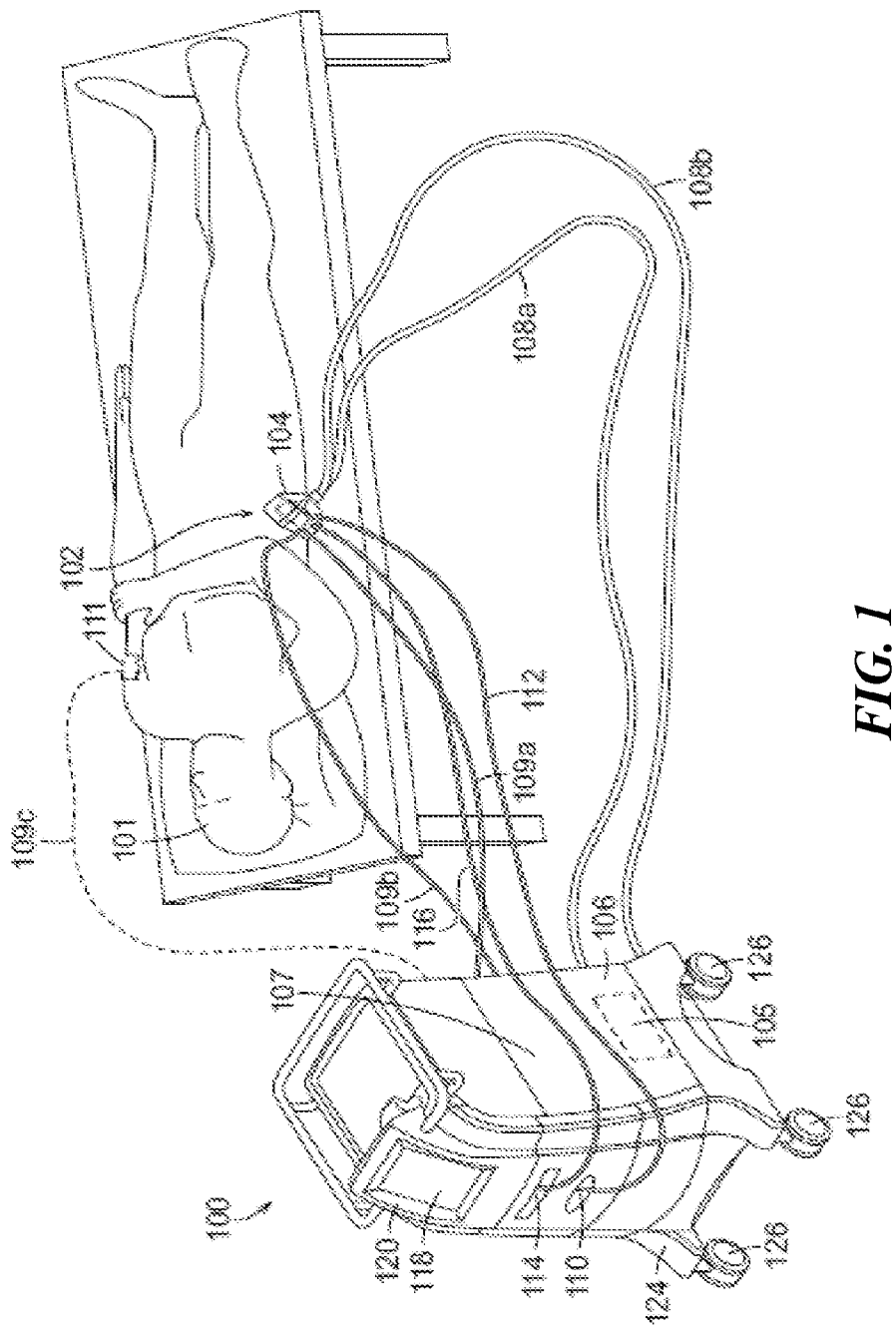
FIG. 1 is a partially schematic, isometric view of a treatment system for non-invasively removing heat from subcutaneous lipid-rich target areas of a subject in accordance with an embodiment of the disclosure.

The present disclosure describes cryoprotectant compositions, treatment systems and methods for cooling of targeted tissue. Several of the details set forth below are provided to describe the following examples and methods in a manner sufficient to enable a person skilled in the relevant art to practice, make and use them. Several of the details and advantages described below, however, may not be necessary to practice certain examples and methods of the technology. Additionally, the technology may include other examples and methods that are within the scope of the technology but are not described in detail.

Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, stages, or characteristics may be combined in any suitable manner in one or more examples of the technology. The headings provided herein are for convenience only and are not intended to limit or interpret the scope or meaning of the technology.

Compositions and formulations for use with devices and systems that enable tissue cooling (e.g., for alteration and reduction of adipose tissue, body contouring and augmentation, for the treatment of acne, for the treatment of hyperhidrosis, etc.), such as cryotherapy applications, are described. Aspects of the disclosure are further directed to methods, compositions and devices that provide protection of non-targeted cells, such as non-lipid-rich cells (e.g., in the dermal and epidermal skin layers), by preventing or limiting freeze damage during dermatological and related aesthetic procedures that require sustained exposure to cold temperatures. For example, pretreatment methods and topical cryoprotectant compositions for use may improve the freeze tolerance and/or freeze avoidance of non-lipid-rich skin cells. Further aspects of the disclosure include systems for enhancing sustained and/or replenishing release of cryoprotectant compositions to a treatment site prior to and/or during cooling applications.

Various tissue cryoprotectant compositions to reduce the susceptibility of non-targeted skin cells exposed to cold-induced damage during heat removal from targeted lipid-rich cells are disclosed and may include a freezing point depressant along with a thickening agent, a pH buffer, a humectant, a surfactant and/or other adjuvants and additives to facilitate protection of the non-lipid cells in the targeted treatment tissue. One embodiment of a composition for use with a system for cooling subcutaneous lipid-rich cells comprises a cryoprotectant configured to be applied to an interface between a treatment device and skin of a human subject. Another embodiment of the compositions includes cryoprotectant formulations configured to be applied topically to a region of subject's skin prior to introduction of cooling treatment and post-cooling applications.

Additional aspects of the technology are directed to methods for treating a target region of a human subject's body to facilitate cryoprotectant absorption and retention in dermal and epidermal layers prior to and during the introduction of cooling. Enhanced cryoprotectant absorption can be facilitated, for example, by increasing a temperature of the dermal and epidermal layers prior to applying a topical cryoprotectant and/or removing heat from lipid-rich cells in the target region. Further embodiments include increasing a permeability of a subject's skin to cryoprotectant compositions using mechanical stimulation, agitation and/or abrasion.

Various aspects of the technology are directed to compositions for use with a system for cooling subcutaneous lipid-rich tissue of a subject having skin. In one embodiment, the composition can include a freezing point depressant (e.g., a cryoprotectant agent) configured to be applied to the skin of the subject. The freezing point depressant can be configured to lower a freezing point of cells in an epidermal layer and/or a dermal layer of the skin. The composition can also include at least one of a thickening agent, a pH buffer, a humectant and a surfactant. For example, the composition can include one or more thickening agents, one or more pH buffers, one or more humectants, and/or one or more surfactants. The composition can further include at least one of (a) an adjuvant configured to increase permeation of the freezing point depressant through a stratum corneum of the skin and into the epidermis and/or dermis (e.g., epidermal and/or dermal skin layers), (b) a solute configured to increase an effective concentration of the solute in an intracellular fluid or an extracellular fluid in the epidermis and/or dermis, (c) a hydrophilic molecule, and (d) a lipophobic molecule. In one embodiment, the solute increases the effective concentration of the freezing point depressant in the intracellular fluid in the epidermis and/or dermis. In other embodiments, the solute increases the effective concentration of the freezing point depressant in the extracellular fluid in the epidermis and/or dermis.

Other aspects of the technology are directed to compositions for use with a system for transdermal cooling of targeted cells of a subject having skin. In one embodiment, the composition can include a freezing point depressant configured to be applied to the skin of the subject. The freezing point depressant can be configured to lower a freezing point of non-targeted cells in a target region of the skin. The composition can also include at least one of a thickening agent, a pH buffer, a humectant and a surfactant. The composition can further include at least one of (a) an adjuvant configured to increase permeation of the freezing point depressant through a stratum corneum of the skin, (b) a solute configured to increase an effective concentration of the solute in an intracellular fluid or an extracellular fluid in the target region, (c) a hydrophilic molecule, and (d) a lipophobic molecule. In some embodiments, the composition is configured to protect the non-targeted cells while allowing targeted cells in the target region to be affected while cooling. In one embodiment, the targeted cells have a higher lipid content than the non-targeted cells. For example, the targeted cells are subcutaneous lipid-rich cells. In another embodiment, the targeted cells are lipid-rich cells in the breast. For example, the cryoprotectant compositions disclosed herein can facilitate non-target cell and mammary gland protection in the breast while transdermal cooling can selectively target the lipid-rich fat cells for breast contouring and/or breast reduction/augmentation procedures. In a further embodiment, the targeted cells are cells associated with exocrine glands within or near the skin (e.g., epidermal and/or dermal layers) of a subject. For example, the targeted cells may be lipid-producing cells residing within or at least proximate to sebaceous glands, or in another embodiment, apocrine sweat glands. The composition can be in contact with at least one of the skin of a subject at a target region and a surface of a treatment device suitable for removing heat from the target region.

Other embodiments of the present technology include systems for affecting lipid-rich cells in a target region of a human subject's body. In one embodiment, the system can include an applicator having a heat-exchanging element configured to reduce a temperature of the target region from a natural body temperature to a lower temperature in the target region. The system can also include a cryoprotectant release structure between a surface of the applicator and a skin surface in the target region. The cryoprotectant release structure can be configured to retain and release a cryoprotectant between the surface of the applicator and the skin surface. In some embodiments, the system can further include a cryoprotectant configured to lower a freezing point of non-targeted cells (e.g., non-lipid-rich cells) in or near the target region. In one embodiment, the cryoprotectant can include one or more of an adjuvant configured to increase absorption of the cryoprotectant into an epidermal layer and/or dermal layer at the target region, a solute configured to raise an effective concentration of the solute in the epidermal layer and/or dermal layer, a hydrophilic molecule, and a lipophilic molecule.

In another embodiment, a system for non-invasive, transdermal removal of heat from lipid-rich cells of a subject's body includes an applicator having a heat-exchanging element. The heat-exchanging element can be configured to reduce a temperature of a target region beneath the epidermis of the subject selectively to reduce the temperature of lipid-rich cells in the target region from a natural body temperature to a lower temperature in the target region. In one embodiment, the lower temperature can be less than −10° C., or in another embodiment between about −10° C. to about −15° C., or in another embodiment between about −15° C. to about −25° C. The system can also include a first cryoprotectant configured to lower a freezing point of non-targeted cells (e.g., non-lipid-rich cells) in or near the target region. In one embodiment, the first cryoprotectant can be configured to lower the freezing point of the cells to about −20° C. to about −10° C., in another embodiment to about −18° C. to about −10° C., or in another embodiment to about −15° C. to about −10° C. In one embodiment, the first cryoprotectant can include one or more of an adjuvant configured to increase absorption of the cryoprotectant into an epidermal layer and/or dermal layer at the target region, a solute configured to raise an effective concentration of the solute in the epidermal layer and/or dermal layer, a hydrophilic molecule, and a lipophilic molecule. The first cryoprotectant, in some embodiments, protects non-lipid cells such that the lipid-rich cells in the target region are substantially affected while non-lipid rich cells in the target region are not substantially affected when the temperature is reduced. In one embodiment, the target region is subcutaneous adipose tissue. In another embodiment, the target region is in the dermal layer of the subject's skin.

Additional embodiments of such systems may include a second cryoprotectant applied to the target region. The second cryoprotectant can be the same composition as the first cryoprotectant, or in other embodiments, the second cryoprotectant can be different. For example, the first cryoprotectant may include alcohol (e.g., isopropyl alcohol) and the second cryoprotectant may be an alcohol-free composition. In other embodiments, the first and second cryoprotectants are combined into a single composition and applied together onto the skin by rubbing the single composition into the skin with a mild abrasive cloth. In other embodiments, the first cryoprotectant is first applied to the skin and thereafter the second cryoprotectant is applied to the skin. In certain embodiments, a series of substances can be applied to the target region. Each substance can be adapted to (1) enhance the delivery or effect of a subsequently applied substance, (2) enhance the effect of cryotherapy, (3) reduce treatment times, and/or (4) reduce adverse effects of cryotherapy.

In yet another embodiment, a system for removing heat from subcutaneous lipid-rich cells of a subject having skin can include a treatment unit and an applicator having a cooling unit in communication with the treatment unit. The system can also include a pre-treatment composition configured to be applied to the skin to increase a permeability of the skin. The pre-treatment composition can, in some embodiments, comprise an alpha-hydroxy acid, glycolic acid, butylene glycol, a fatty acid, d-limonene, a terpene, a terpenoid, N-methyl-2-pyrrolidone, dimethylsulphoxide, 1,3-diphenylurea, dodecyl,N,N-dimethyl-aminoacetate, ethanol, alcohol, Azone®, Azone® derivatives, ethyl acetate, beta-cyclodextrin, alcohol, and/or isopropyl alcohol.

In other embodiments, the pre-treatment composition can be a first cryoprotectant composition configured to lower a freezing point of non-lipid-rich cells at the target region. In one example, the first cryoprotectant can include one or more of an adjuvant configured to increase absorption of the first cryoprotectant into an epidermal layer and/or dermal layer at the target region, a solute configured to raise an effective concentration of the solute in the epidermal layer and/or dermal layer, a hydrophilic molecule, and a lipophilic molecule. In some embodiments, the system can further include a cryoprotectant composition, or second cryoprotectant composition, configured to be applied to the skin to permeate into the skin to lower a freezing point of non-lipid-rich cells in the skin. In some arrangements, the pre-treatment composition can be configured to facilitate an absorption of the cryoprotectant. In many embodiments, any one of the applicator, the treatment site, the pre-treatment composition and/or the cryoprotectant can be warmed prior to contacting the skin.

Further aspects of the present technology are directed to treatment methods for affecting a target region of a human subject's body to alter subcutaneous adipose tissue. In one embodiment, a method can include warming a treatment site (e.g., at or near the target region) and/or warming an applicator, and applying a cryoprotectant to a surface of the skin at the treatment site. In another embodiment, a method can include applying a cryoprotectant to a surface of the skin at a treatment site and, prior to removing heat from the treatment site, mechanically stimulating (e.g., abrading, agitating, brushing, rubbing, massaging, etc.) an upper layer of skin at the treatment site to facilitate penetration and/or absorption of the cryoprotectant (e.g., increase a permeability of the skin to the cryoprotectant). In either of these embodiments, the method can also include removing heat from the target region of the human subject to cool subcutaneous lipid-rich cells in the target region to a temperature below normal body temperature. Additional methods for affecting a target region of a subject's body can include applying a cryoprotectant to a surface of the skin at a treatment site and, prior to removing heat from the treatment site, moving the cryoprotectant along the surface of the skin at the treatment site to facilitate absorption of the cryoprotectant.

Some of the embodiments disclosed herein can be for cosmetically beneficial alterations of a variety of body regions. As such, some treatment procedures may be for the sole purpose of altering the body region to conform to a cosmetically desirable look, feel, size, shape or other desirable cosmetic characteristic or feature. Accordingly, at least some embodiments of the cosmetic procedures can be performed without providing any, or in another embodiment, providing minimal therapeutic effect. For example, some treatment procedures may be directed to treatment goals that do not include restoration of health, physical integrity, or the physical well-being of a subject. In other embodiments, however, the cosmetically desirable treatments may have therapeutic outcomes (whether intended or not), such as, psychological benefits, alteration of body hormones levels (by the reduction of adipose tissue), etc. The cosmetic methods can target subcutaneous regions to change a subject's appearance such as, for example, procedures performed on a subject's "love-handles" (i.e., excess adipose tissue at the side of a subject's waistline). In another embodiment, the cosmetic methods can target sebaceous glands in the subject's skin to change a subject's appearance such as, for example, procedures performed on a subject's face. In another embodiment, the cosmetic methods can target sweat glands in the subject's skin to treat hyperhidrosis.

B. Cryotherapy

FIG. 1 and the following discussion provide a brief, general description of an example of a suitable treatment system 100 in which aspects of the technology can be implemented. In some embodiments, the treatment system 100 can be a temperature-controlled treatment system for exchanging heat from subcutaneous lipid-rich cells of a subject 101. Those skilled in the relevant art will appreciate that other examples of the disclosure can be practiced with other treatment systems and treatment protocols, including invasive, minimally invasive, other non-invasive medical treatment systems, and/or combinations of one or more of the above for treating a subject 101. In general, the term "treatment system", as used generally herein, refers to any of the above-referenced categories of cosmetic or medical treatment systems as well as any treatment regimens or medical device usage. In various embodiments, the treatment system 100 includes a controller, a computing device, a data acquisition device, a chiller, and one or more treatment devices. These components can be implemented in various embodiments to apply selected treatment profiles to the subject 101 (e.g., a human or animal) for reducing adipose tissue.

In one embodiment, the treatment system 100 is suitable for altering a human subject's subcutaneous adipose tissue, such as by cooling. The term "subcutaneous tissue" means tissue lying beneath the dermis and includes subcutaneous fat, or adipose tissue, which primarily is composed of lipid-rich cells, or adipocytes. In another embodiment, the treatment system 100 is suitable for at least partially disrupting exocrine gland function in the skin of a human subject. For example, the treatment system 100 is suitable for altering (e.g., reducing) or affecting sebum production, such as by cooling lipid-producing cells residing in or at least proximate to sebaceous glands (e.g., glandular epithelial cells) in the subject's skin. In another example, the treatment system is suitable for altering (e.g., reducing) or affecting axilla sweat production, such as by cooling apocrine cells residing in axilla apocrine glands in the subject's skin. Such alteration (e.g., by cooling) is believed to be an intermediate and/or final result of one or more mechanisms acting alone or in combination. It is thought that such mechanism or mechanisms can trigger an apoptotic cascade, which is believed to be the dominant form of lipid-rich cell death by non-invasive cooling alone or in combination with other forms of cell interrogation.

In several embodiments, apoptosis of the subcutaneous lipid-rich cells in the region of the subject 101 being treated is a desirable outcome for beneficially altering (e.g., sculpting and/or reducing) adipose tissue. Apoptosis, also referred to as "programmed cell death", is a genetically-induced death mechanism by which cells self-destruct without incurring damage to surrounding tissues. An ordered series of biochemical events may induce cells to morphologically change. These changes include cellular blebbing, loss of cell membrane asymmetry and attachment, cell shrinkage, chromatin condensation, and chromosomal DNA fragmentation. Injury via an external stimulus, such as cold exposure, is one mechanism that can induce apoptosis in cells. Nagle, W. A., Soloff, B. L., Moss, A. J. Jr., Henle, K. J. "Cultured Chinese Hamster Cells Undergo Apoptosis After Exposure to Cold but Nonfreezing Temperatures" Cryobiology 27, 439-451 (1990). One aspect of apoptosis, in contrast to cellular necrosis (a traumatic form of cell death causing, and sometimes induced by, local inflammation), is that apoptotic cells express and display phagocytic markers on the surface of the cell membrane, thus marking the cells for phagocytosis by, for example, macrophages. As a result, phagocytes can engulf and remove the dying cells (e.g., the lipid-rich cells) without eliciting an immune response.

Without being bound by theory, one mechanism of apoptotic lipid-rich cell death by cooling is believed to involve localized crystallization of lipids within the adipocytes at temperatures that do not induce crystallization in non-lipid-rich cells. The crystallized lipids may selectively injure these cells, inducing apoptosis (and may also induce necrotic death if the crystallized lipids damage or rupture the bilayer lipid membrane of the adipocyte). Another mechanism of injury involves the lipid phase transition of those lipids within the cell's bilayer lipid membrane, which results in membrane disruption, thereby inducing apoptosis. This mechanism is well documented for many cell types and may be active when adipocytes, or lipid-rich cells, are cooled. Mazur, P., "Cryobiology: the Freezing of Biological Systems" Science, 68: 939-949 (1970); Quinn, P. J., "A Lipid Phase Separation Model of Low Temperature Damage to Biological Membranes" Cryobiology, 22: 128-147 (1985); Rubinsky, B., "Principles of Low Temperature Preservation" Heart Failure Reviews, 8, 277-284 (2003). Other possible mechanisms of adipocyte damage, described in U.S. Pat. No. 8,192,474, relates to ischemia/reperfusion injury that may occur under certain conditions when such cells are cooled as described herein. For instance, during treatment by cooling as described herein, the targeted adipose tissue may experience a restriction in blood supply and thus be starved of oxygen due to isolation while pulled into, e.g., a vacuum cup, or simply as a result of the cooling which may affect vasoconstriction in the cooled tissue. In addition to the ischemic damage caused by oxygen starvation and the build-up of metabolic waste products in the tissue during the period of restricted blood flow, restoration of blood flow after cooling treatment may additionally produce reperfusion injury to the adipocytes due to inflammation and oxidative damage that is known to occur when oxygenated blood is restored to tissue that has undergone a period of ischemia. This type of injury may be accelerated by exposing the adipocytes to an energy source (via, e.g., thermal, electrical, chemical, mechanical, acoustic or other means) or otherwise increasing the blood flow rate in connection with or after cooling treatment as described herein. Increasing vasoconstriction in such adipose tissue by, e.g., various mechanical means (e.g., application of pressure or massage), chemical means or certain cooling conditions, as well as the local introduction of oxygen radical-forming compounds to stimulate inflammation and/or leukocyte activity in adipose tissue may also contribute to accelerating injury to such cells. Other yet-to-be understood mechanisms of injury may also exist.

In addition to the apoptotic mechanisms involved in lipid-rich cell death, local cold exposure may induce lipolysis (i.e., fat metabolism) of lipid-rich cells. For example, cold stress has been shown to enhance rates of lipolysis from that observed under normal conditions which serves to further increase the volumetric reduction of subcutaneous lipid-rich cells. Vallerand, A. L., Zamecnik. J., Jones, P. J. H., Jacobs, I. "Cold Stress Increases Lipolysis, FFA Ra and TG/FFA Cycling in Humans" Aviation, Space and Environmental Medicine 70, 42-50 (1999).

Without being bound by theory, the selective effect of cooling on lipid-rich cells is believed to result in, for example, membrane disruption, shrinkage, disabling, destroying, removing, killing, or another method of lipid-rich cell alteration. For example, when cooling the subcutaneous tissues to a temperature significantly lower than 37° C., subcutaneous lipid-rich cells can selectively be affected. In general, the cells in the epidermis and dermis of the subject 101 have lower amounts of lipids compared to the underlying lipid-rich cells forming the subcutaneous tissues. Since lipid-rich cells are more sensitive to cold-induced damage than non-lipid-rich epidermal or dermal cells, it is possible to use non-invasive or minimally invasive cooling to destroy lipid-rich cells without harming the overlying skin cells.

As discussed above, deep hypodermal fat cells are more easily damaged by low temperatures than the overlying dermal and epidermal layers of skin, and, as such, thermal conduction can be used to cool the desired layers of skin to a temperature above the freezing point of water, but below the freezing point of fat. However, there is an associated risk of freezing the upper layers of skin. Without being bound by theory, it is believed that low temperatures may potentially cause damage in the epidermis and/or dermis via at least intracellular and/or extracellular ice formation. The ice may expand and rupture the cell wall, but it may also form sharp crystals that locally pierce the cell wall as well as vital internal organelles, either or both resulting in cell death. When extracellular water freezes to form ice, the remaining extracellular fluid becomes progressively more concentrated with solutes. The high solute concentration of the extracellular fluid may cause intracellular fluid be driven through the semi-permeable cellular wall by osmosis resulting in cell dehydration and death.

A freezing point of a material is most reliably ascertained by warming frozen material slowly and measuring a temperature at which melting begins to occur. This temperature is generally not ambiguous if the material is slowly warmed. Partial melting will begin to occur at the freezing/melting point. Conversely, if a non-frozen material is cooled, its freezing/melting point is harder to ascertain since it is known that many materials can simply "supercool," that is they can be cooled to a bulk temperature below their freezing/melting point and still remain in a non-frozen state.

In a typical procedure, a cooling element is positioned at least proximate to the surface of a subject's skin and heat is removed from the underlying adipose tissue through the upper layers of the skin. This creates a thermal gradient with the coldest temperatures near the cooling element (e.g., the upper layers of skin). When cooling is applied to the skin, for example, the resulting thermal gradient causes the temperature of the upper layer(s) of the skin to be lower than that of the targeted underlying lipid-rich cells. This makes it challenging to reduce the temperature of the deep lipid-rich cells low enough to be destructive to these target cells (e.g., induce apoptosis, cell death, etc.) while also maintaining the temperature of the upper and surface skin cells high enough so as to be protective (e.g., non-destructive). The temperature difference between these two thresholds can be small (e.g., approximately, 5° C. to about 10° C., less than 10° C., less than 15° C., etc.). Protection of the overlying non-lipid-rich cells (e.g., typically water-rich dermal and epidermal skin cells) from freeze damage during dermatological and related aesthetic procedures that require sustained exposure to cold temperatures may include improving the freeze tolerance and/or freeze avoidance of these skin cells.

In some embodiments, the treatment system 100 can cool the skin of the patient to a temperature in a range of from about −20° C. to about 20° C. In other embodiments, the cooling temperatures can be from about −20° C. to about 10° C., from about −18° C. to about 5° C., from about −15° C. to about 5° C., or from about −15° C. to about 0° C. In further embodiments, the cooling temperatures can be less than −10° C., or in yet another embodiment, from about −15° C. to about −25° C.

As explained in more detail below, a cryoprotectant having a freezing point in the range of about −40° C. to about 0° C. can be applied to the surface of the skin of the patient or subject 101, or to an interface between the treatment device or applicator 104 and the skin of the patient or subject 101. As used herein, "cryoprotectant," "cryoprotectant agent," and "composition" mean substances (e.g., compositions, formulations, compounds, etc.) that assist in preventing freezing of non-lipid-rich tissue (e.g., dermal and/or epidermal tissue) compared to an absence of the substances(s). In one embodiment, the cryoprotectant allows, for example, the treatment device or applicator 104 to be pre-cooled prior to being applied to the subject 101 for more efficient treatment. In another embodiment, the cryoprotectant allows for enhanced uptake or absorption and/or retention in the dermal and epidermal layers prior to and during the introduction of cooling. Further, the cryoprotectant can also enable the treatment device or applicator 104 to be maintained at a desired temperature while preventing ice from forming on a surface of the treatment device or applicator 104, and thus reduces the delay in reapplying the treatment device or applicator 104 to the subject. Yet another aspect of the technology is that the cryoprotectant may prevent the treatment device or applicator 104 from freezing to the skin of the patient or subject 101. Additionally, the cryoprotectant may protect biological tissues of a subject, such as a mammal, from freezing damage (e.g., damage due to ice formation). The cryoprotectant composition may also include one or more additives present in the compound and configured to provide selected properties to the compound. Further details regarding cryoprotectants suitable for use with the treatment system 100 and/or in treatment regimens associated with cooling lipid-rich tissue are described in greater detail below.

C. Suitable Cryoprotectant and Pre-Treatment Compositions

A cryoprotectant suitable to be used in the treatment system 100 of FIG. 1 and/or in treatment regimens associated with use of suitable treatment systems for cooling lipid-rich or lipid-producing tissue (e.g., subcutaneous adipose tissue, glandular epithelial cells) is a substance that may protect biological tissues of a subject from freezing damage (e.g., damage due to ice formation within the tissue). The cryoprotectant can be used as a pre-treatment formulation applied to the skin of the subject prior to removing heat to increase a permeability of the skin and/or to lower a freezing point of non-lipid or otherwise non-targeted cells (e.g., in epidermal and/or dermal layers). In these or other embodiments, the cryoprotectant can also be used during heat removal when provided with the applicator 104 (FIG. 1) and as further described herein.

The cryoprotectant may contain a freezing point depressant along with one or more other components, e.g., a thickening agent, a pH buffer, a humectant, a surfactant, and/or other additives configured to provide selected properties to the compound. The cryoprotectant may be formulated as a non-freezing liquid (e.g., an aqueous solution or a non-aqueous solution), a non-freezing gel, a non-freezing hydrogel, or a non-freezing paste. The cryoprotectant may be hygroscopic, thermally conductive, and can be biocompatible. In certain embodiments, the cryoprotectant may be formulated to be acoustically transparent to allow ultrasound to pass through the cryoprotectant, such as a water-based gel described in U.S. Pat. No. 4,002,221 issued to Buchalter and U.S. Pat. No. 4,459,854 issued to Richardson et al., the entire disclosures of which are incorporated herein by reference.

The freezing point depressant can include propylene glycol (PG), polyethylene glycol (PEG), polypropylene glycol (PPG), ethylene glycol, dimethyl sulfoxide (DMSO), combinations thereof, or other glycols. The freezing point depressant may also include ethanol, propanol, iso-propanol, butanol, and/or other suitable alcohol compounds. Certain freezing point depressants (e.g., PG, PPG, PEG, etc.) may also be used to improve spreadability of the cryoprotectant and to provide lubrication. The freezing point depressant may lower the freezing point of a solution (e.g., body fluid) to about 0° C. to −40° C. In other embodiments the freezing point of a solution can be lowered to about −10° C. to about −20° C., about −10° C. to about −18° C., or to about −10° C. to about −15° C. In certain embodiments, the freezing point of a solution can be lowered to a temperature less than about 0° C., less than about −5° C., less than about −10° C., less than about −12° C., less than about −15° C., less than about −16° C., less than about −17° C., less than about −18° C., less than about −19° C., or less than about −20° C. For example, the freezing point depressant may lower the freezing point of a solution (e.g., body fluid) to a temperature less than about −20° C. to about −25° C., less than about −20° C. to about −30° C., less than about −25 to about −35° C., or less than about −30° C. to about −40° C.

The thickening agent can include carboxyl polyethylene polymer, hydroxyethyl xylose polymer, carboxyl methylcellulose, hydroxyethyl cellulose (HEC), and/or other viscosity modifiers to provide a viscosity in the range of about 1 cP to about 10,000 cP. In one embodiment, the thickening agent can provide a viscosity in the range of about 4,000 cP to about 8,000 cP. In another embodiment, the thickening agent can provide a viscosity in the range of about 5,000 cP to about 7,000 cP. Other viscosities can be achieved, if needed or desired. In various embodiments, a cryoprotectant having a viscosity in one or more of these ranges may readily adhere to the treatment device, the skin of the subject, and/or the interface between the treatment device and the skin of the subject during treatment.

The pH buffer may include cholamine chloride, cetamide, glycine, tricine, glycinamide, bicine, and/or other suitable pH buffers. The pH buffer may help the cryoprotectant to have a consistent pH of about 3.5 to about 11.5. In other embodiments, the pH can be consistently between about 5 to about 9.5, and in further embodiments between about 6 to about 7.5. In certain embodiments, the pH of the cryoprotectant may be close to the pH of the skin of the subject.

The humectant may include glycerin, alkylene glycol, polyalkylene glycol, propylene glycol, glyceryl triacetate, polyols (e.g., sorbitol and/or maltitol), polymeric polyols (e.g., polydextrose), quillaia, lactic acid, and/or urea. The humectant may promote the retention of water to prevent the cryoprotectant from drying out.

The surfactant may include sodium dodecyl sulfate, ammonium lauryl sulfate, sodium lauryl sulfate, alkyl benzene sulfonate, sodium lauryl ether sulfate, and other suitable surfactants. The surfactant may promote easy spreading of the cryoprotectant when an operator applies the cryoprotectant to the treatment device, the skin of the subject, and/or the interface between the treatment device and the skin of the subject during treatment.

In several embodiments, the cryoprotectant composition may also include adjuvants that increase the concentration of the cryoprotectant at lower tissue depths. Such adjuvants can include, for example, glycolic acid and/or other alpha-hydroxy acids, such as lactic acid, citric acid, mandelic acid, alcohol, and/or isopropyl alcohol. In some embodiments, such adjuvants can induce diminished cohesion between corneocytes at the lowest levels of the stratum corneum allowing facilitated permeation of the cryoprotectant formulation into the epidermis and dermis. In one embodiment, glycolic acid can facilitate cryoprotection of mucopolysaccharides present in the extracellular matrix of the epidermal and dermal tissue layers.

The cryoprotectant composition may also include solutes and/or adjuvants that locally modify colligative properties of the tissue to, for example, depress the freezing point of the non-lipid-rich cells affected by the cryoprotectant. Freezing point depression describes a process in which adding a solute or increasing the effective concentration of a solute in the intracellular fluid compartment of the non-lipid-rich cells or in the extracellular fluid surrounding the non-lipid-rich cells, decreases the freezing point of the respective fluids. Some such solutes and/or adjuvants can include, for example, calcium salts (e.g., calcium chloride), potassium salts (e.g., potassium chloride, potassium acetate), magnesium salts (e.g., magnesium chloride), ammonium sulphate, acetic acid, glucose, urea, camphor, menthyl lactate, mannose, and related compounds.

In some compositions, addition or an increase in concentration of solutes in the cryoprotectant can be used to form a hypertonic formulation that locally dehydrates non-lipid-rich tissue (e.g., via osmotic dehydration). For example, the composition can include sodium salts (e.g., sodium chloride), calcium salts (e.g., calcium chloride), potassium salts (e.g., potassium chloride, potassium acetate), magnesium salts (e.g., magnesium chloride), ammonium sulphate and related compounds.

In further embodiments, the cryoprotectant compositions can include hydrophilic and/or lipophobic molecules that favorably partition the cryoprotectant within the upper layers (e.g., the epidermis and dermis) of the skin. Examples of hydrophilic molecules can include many compounds, especially those that reduce the surface tension of water, such as surfactants, gelatins and hydrogels. In one embodiment, the cryoprotectant includes glycolic acid that is completely miscible in water and is hydrophilic. Examples of lipophobic molecules can include fluorocarbons, which are typically non-polar and immiscible in water.

The cryoprotectant may also include other additives in addition to or in lieu of the composition components described above. For example, some of the embodiments of cryoprotectant compositions may also include a coloring agent, fragrance or perfume, emulsifier, stabilizer, an anesthetic agent, and/or other ingredient.

In a particular embodiment, the cryoprotectant may include about 30% propylene glycol, about 30% glycerin, and about 40% ethanol by weight. In another embodiment, the cryoprotectant may include about 40% propylene glycol, about 0.8% hydroxyethyl cellulose, and about 59.2% water by weight. In a further embodiment, the cryoprotectant may include about 50% polypropylene glycol, about 40% glycerin, and about 10% ethanol by weight. In yet another embodiment, the cryoprotectant may include about 59.5% water, about 40% propylene, and about 0.5% hydroxyethyl cellulose by weight.

In other embodiments, the cryoprotectant can include about 30-40% propylene glycol or polypropylene glycol. In one embodiment, the cryoprotectant can include about 30-50% by volume of one or more freezing point depressants. Some cryoprotectant compositions can further include 50% wt./vol. to about 70% wt./vol. of a combination of one or more of a thickening agent, a pH buffer, a humectant, a surfactant, and one more additives that (a) facilitate permeation of the cryoprotectant into the epidermis and dermis, (b) increase an intracellular concentration of solutes of dermal and epidermal cells, (c) form a hypertonic cryoprotectant formulation and/or (d) hydrophilic and/or lipophobic molecules.

In further embodiments, the cryoprotectant composition can include one or more freezing point depressants in an amount between about 25% wt./vol. and about 55% wt. vol., about 30% wt./vol. and about 50% wt./vol., about 30% wt./vol. and about 40% wt./vol., about 35% wt./vol. and about 48% wt./vol. about 35% wt./vol. and about 45% wt./vol., about 38% wt./vol. and about 42% wt./vol. about 40% wt./vol. and about 50% wt./vol., about 40% wt./vol. and about 45% wt./vol.; or, in other embodiments, greater than about 30% wt./vol., about 35% wt./vol., about 40% wt./vol., about 45% wt./vol., or about 50% wt./vol.

In a particular embodiment, a first cryoprotectant composition for use as a pre-treatment formulation (e.g., for affecting skin at the treatment site prior to the removal of heat), can include about 30% wt./vol. isopropyl alcohol, about 40% propylene glycol, and about 30% water. A second cryoprotectant composition for use during heat removal (e.g., cooling and/or at least partially or totally freezing of targeted tissue) can be the same formulation as the first cryoprotectant composition or can be different. For example, the second cryoprotectant can comprise about 40% propylene glycol and about 60% water.

In other embodiments, the cryoprotectant composition (e.g., first and/or second cryoprotectant compositions) can include a combination of one or more of a thickening agent, a pH buffer, a humectant, a surfactant, and one more additives that (a) facilitate permeation of the cryoprotectant into the epidermis and dermis, (b) increase an intracellular concentration of solutes of dermal and epidermal cells, (c) form a hypertonic cryoprotectant formulation and/or (d) hydrophilic and/or lipophobic molecules in an amount totaling between about 45% wt./vol. and about 75% wt. vol., about 50% wt./vol. and about 70% wt./vol., about 60% wt./vol. and about 70% wt./vol., about 52% wt./vol. and about 65% wt./vol. about 55% wt./vol. and about 65% wt./vol., about 58% wt./vol. and about 62% wt./vol. about 50% wt./vol. and about 60% wt./vol., about 55% wt./vol. and about 60% wt./vol.

One aspect of the present technology described above is that an operator may use lower treatment temperatures for selectively affecting lipid-rich cells of the subject without causing freezing damage to the non-lipid-rich cells in the epidermis and/or dermis of the subject. The applied cryoprotectant may lower the freezing point of the skin of the subject or body fluid in the target region to at least reduce the risk of intracellular and/or extracellular ice formation at such low treatment temperatures.

Another aspect of the present technology is that the non-lipid-rich cells in the epidermis and/or dermis of the patient may be continually protected against freezing damage. It is believed that a topically administered cryoprotectant may protect the treatment region of the skin of the subject. After the cryoprotectant is applied to the skin of the subject, the cryoprotectant is believed to enter the epidermis, the dermis, and eventually the blood stream of the subject. The subject's blood stream then may carry the cryoprotectant away from the treatment region. As a result, the cryoprotectant concentration in the treatment region drops, and the freezing point of the subject's affected body fluid increases to heighten the risk of freezing damage. Accordingly, continually supplying the cryoprotectant to the skin of the subject may at least reduce or even prevent such a risk. Further, topically administering, either before heat removal as a pre-treatment composition or in conjunction with the applicator 104 (FIG. 1) during heat removal, a cryoprotectant that is effectively partitioned in the epidermis and/or dermis of the subject may prevent the cryoprotectant from being carried by the blood stream away from the treatment site during treatment. In some embodiments, a sufficient amount of cryoprotectant can be continuously or periodically delivered to the non-targeted tissue to prevent or inhibit freezing damage to the non-targeted tissue.

Still another aspect associated with several of the embodiments described above is that the additives, adjuvants, solutes, etc. in the cryoprotectant can provide a variety of desired additional properties to the cryoprotectant material, with minimal or no effect on the chemistry and rheological properties of the cryoprotectant. Accordingly, the additives will not interfere with the ability of the cryoprotectant to protect a subject's biological tissues from freezing. Further, various additives described herein will enhance and/or facilitate the ability of the cryoprotectant to protect a subject's biological tissues from freezing or other types of damage.

As described herein, the cryoprotectant can be used with the treatment system 100 to transdermally cool and selectively affect the patient's subcutaneous lipid-rich tissue while protecting non-lipid rich cells (e.g., residing in epidermal and/or dermal layers) from being substantially affected at the reduced temperatures. Subcutaneous lipid-rich tissue can be treated for a variety of therapeutic and cosmetic body-contouring applications, such as reduction of adipose tissue residing in identified portions of the patient's body, such as chin, cheeks, arms, pectoral areas, thighs, calves, buttocks, abdomen, "love handles", back, breast, etc. For example, use of the cryoprotectant with the treatment system 100 to transdermally cool adipose tissue in the breast can be used for breast contouring and size reduction in a manner that facilitates protection of non-target tissue in the breast. Further examples include use of the cryoprotectant and treatment system 100 to contour and/or reduce a volumetric size of love handles, abdominal fat, back fat, etc., without substantially affecting non-targeted cells (e.g., cells in the epidermal and/or dermal layers).

In another embodiment, the cryoprotectant can be used with the treatment system 100 to cool the skin of the patient to selectively affect (e.g., injure, damage, kill) secreting exocrine glandular cells. For example, secreting glandular cells residing in axilla apocrine sweat glands can be targeted by the treatment system 100 for the treatment of hyperhidrosis. In another example, lipid-producing cells residing in or at least proximate to sebaceous glands (e.g., glandular epithelial cells) present in the dermis of a target region can be targeted by the treatment system 100 for the treatment of acne or other skin condition. The lipid-producing cells residing in and/or proximate to sebaceous glands contribute to production of sebum, a waxy and oily secretion that can contribute to acne. For example, the treatment system 100 can be configured to reduce a temperature of a dermal layer of skin to reduce the temperature of lipid-producing cells residing in or at least proximate to sebaceous glands such that the targeted lipid-producing cells excrete a lower amount of sebum, such that there are fewer lipid-producing cells resulting in less sebum production within the targeted sebaceous glands, or in another embodiment, such that the sebaceous glands are destroyed. The treatment system 100 can be configured, for example, to reduce a subject's acne by cooling acne-prone regions of the body, such as the face, back, shoulders and chest.

D. Suitable Treatment System

Referring to FIG. 1, the illustration is a partially schematic, isometric view showing one example of the treatment system 100 for non-invasively removing heat from subcutaneous lipid-rich target areas of the patient or subject 101, such as an abdominal area 102 or another suitable area. The applicator 104 can engage the target area of the subject 101 and a treatment unit 106 that operate together to cool or otherwise remove heat from the subcutaneous lipid-rich cells of the subject 101. The applicator 104 can be part of an application system, and the applicator 104 can have various configurations, shapes and sizes suitable for different body parts such that heat can be removed from any cutaneous or subcutaneous lipid-rich target area of the subject 101. For example, various types of applicators may be applied during treatment, such as a vacuum applicator, a belt applicator (either of which may be used in combination with a massage or vibrating capability), and so forth. Each applicator 104 may be designed to treat identified portions of the patient's body, such as chin, cheeks, arms, pectoral areas, thighs, calves, buttocks, abdomen, "love handles", back, breast, and so forth. For example, the vacuum applicator may be applied at the back region, and the belt applicator can be applied around the thigh region, either with or without massage or vibration. Exemplary applicators and their configurations usable or adaptable for use with the treatment system 100 variously are described in, e.g., commonly assigned U.S. Pat. No. 7,854,754 and U.S. Patent Publication Nos. 2008/0077201, 2008/0077211 and 2008/0287839. In further embodiments, the system 100 may also include a patient protection device (not shown) incorporated into or configured for use with the applicator 104 that prevents the applicator from directly contacting a patient's skin and thereby reducing the likelihood of cross-contamination between patients, minimizing cleaning requirements for the applicator. The patient protection device may also include or incorporate various storage, computing, and communications devices, such as a radio frequency identification (RFID) component, allowing for example, use to be monitored and/or metered. Exemplary patient protection devices are described in commonly assigned U.S. Patent Publication No. 2008/0077201.

In the present example, the system 100 can also include the treatment unit 106 and supply and return fluid lines 108a-b between the applicator 104 and the treatment unit 106. A treatment unit 106 is a device that can increase or decrease the temperature at a connected applicator 104 that is configured to engage the subject and/or the target region of the subject. The treatment unit 106 can remove heat from a circulating coolant to a heat sink and provide a chilled coolant to the applicator 104 via the fluid lines 108a-b. Alternatively, the treatment unit 106 can circulate warm coolant to the applicator 104 during periods of warming. In further embodiments, the treatment unit 106 can circulate coolant through the applicator 104 and increase or decrease the temperature of the applicator by controlling power delivery to one or more Peltier-type thermoelectric elements incorporated within the applicator. Examples of the circulating coolant include water, glycol, synthetic heat transfer fluid, oil, a refrigerant, and/or any other suitable heat conducting fluid. The fluid lines 108a-b can be hoses or other conduits constructed from polyethylene, polyvinyl chloride, polyurethane, and/or other materials that can accommodate the particular circulating coolant. The treatment unit 106 can be a refrigeration unit, a cooling tower, a thermoelectric chiller, or any other device capable of removing heat from a coolant. In one embodiment, the treatment unit 106 can include a fluid chamber 105 configured to house and provide the coolant. Alternatively, a municipal water supply (e.g., tap water) can be used in place of or in conjunction with the treatment unit 106. In a further embodiment, the applicator 104 can be a fluid-cooled applicator capable of achieving a desired temperature profile such as those described in U.S. patent application Ser. No. 13/830,027, incorporated herein by reference in its entirety. One skilled in the art will recognize that there are a number of other cooling technologies that could be used such that the treatment unit, chiller, and/or applicator need not be limited to those described herein.

The system 100 can optionally include an energy-generating unit 107 for applying energy to the target region, for example, to further interrogate cooled lipid-rich cells in cutaneous or subcutaneous layers via power-lines 109a-b between the applicator 104 and the energy-generating unit 107. In one embodiment, the energy-generating unit 107 can be an electroporation pulse generator, such as a high voltage or low voltage pulse generator, capable of generating and delivering a high or low voltage current, respectively, through the power lines 109a, 109b to one or more electrodes (e.g., cathode, anode) in the applicator 104. In other embodiments, the energy-generating unit 107 can include a variable powered RF generator capable of generating and delivering RF energy, such as RF pulses, through the power lines 109a, 109b or to other power lines (not shown). In a further embodiment, the energy-generating unit 107 can include a microwave pulse generator, an ultrasound pulse laser generator, or high frequency ultrasound (HIFU) phased signal generator, or other energy generator suitable for applying energy, for example, to further interrogate cooled lipid-rich cells in cutaneous or subcutaneous layers. In some embodiments (e.g., RF return electrode, voltage return when using a monopolar configuration, etc.), the system 100 can include a return electrode 111 located separately from the applicator 104; power line 109c (shown in dotted line) can electrically connect the return electrode 111, if present, and the energy-generating unit 107. In additional embodiments, the system 100 can include more than one energy generator unit 107 such as any one of a combination of the energy modality generating units described herein. Systems having energy-generating units and applicators having one or more electrodes are described in commonly assigned U.S. Patent Publication No. 2012/0022518 and U.S. patent application Ser. No. 13/830,413.

In the illustrated example, the applicator 104 is associated with at least one treatment unit 106. The applicator 104 can provide mechanical energy to create a vibratory, massage, and/or pulsatile effect. The applicator 104 can include one or more actuators, such as, motors with eccentric weight, or other vibratory motors such as hydraulic motors, electric motors, pneumatic motors, solenoids, other mechanical motors, piezoelectric shakers, and so on, to provide vibratory energy or other mechanical energy to the treatment site. Further examples include a plurality of actuators for use in connection with a single applicator 104 in any desired combination. For example, an eccentric weight actuator can be associated with one section of an applicator 104, while a pneumatic motor can be associated with another section of the same applicator 104. This, for example, would give the operator of the treatment system 100 options for differential treatment of lipid-rich cells within a single region or among multiple regions of the subject 101. The use of one or more actuators and actuator types in various combinations and configurations with an applicator 104 may be possible.

The applicator 104 can include one or more heat-exchanging units. Each heat-exchanging unit can include or be associated with one or more Peltier-type thermoelectric elements, and the applicator 104 can have multiple individually controlled heat-exchanging zones (e.g., between 1 and 50, between 10 and 45; between 15 and 21, approximately 100, etc.) to create a custom spatial cooling profile and/or a time-varying cooling profile. Each custom treatment profile can include one or more segments, and each segment can include a specified duration, a target temperature, and control parameters for features such as vibration, massage, vacuum, and other treatment modes. Applicators having multiple individually controlled heat-exchanging units are described in commonly assigned U.S. Patent Publication Nos. 2008/0077211 and 2011/0238051.

The system 100 can further include a power supply 110 and a controller 114 operatively coupled to the applicator 104. In one embodiment, the power supply 110 can provide a direct current voltage to the applicator 104 to remove heat from the subject 101. The controller 114 can monitor process parameters via sensors (not shown) placed proximate to the applicator 104 via a control line 116 to, among other things, adjust the heat removal rate and/or energy delivery rate based on the process parameters. The controller 114 can further monitor process parameters to adjust the applicator 104 based on treatment parameters, such as treatment parameters defined in a custom treatment profile or patient-specific treatment plan, such as those described, for example, in commonly assigned U.S. Pat. No. 8,275,442.

The controller 114 can exchange data with the applicator 104 via an electrical line 112 or, alternatively, via a wireless or an optical communication link. Note that control line 116 and electrical line 112 are shown in FIG. 1 without any support structure. Alternatively, control line 116 and electrical line 112 (and other lines including, but not limited to fluid lines 108a-b and power lines 109a-b) may be bundled into or otherwise accompanied by a conduit or the like to protect such lines, enhance ergonomic comfort, minimize unwanted motion (and thus potential inefficient removal of heat from and/or delivery of energy to subject 101), and to provide an aesthetic appearance to the system 100. Examples of such a conduit include a flexible polymeric, fabric, or composite sheath, an adjustable arm, etc. Such a conduit (not shown) may be designed (via adjustable joints, etc.) to "set" the conduit in place for the treatment of the subject 101.

The controller 114 can include any processor, Programmable Logic Controller, Distributed Control System, secure processor, and the like. A secure processor can be implemented as an integrated circuit with access-controlled physical interfaces; tamper resistant containment; means of detecting and responding to physical tampering; secure storage; and shielded execution of computer-executable instructions. Some secure processors also provide cryptographic accelerator circuitry. Secure storage may also be implemented as a secure flash memory, secure serial EEPROM, secure field programmable gate array, or secure application-specific integrated circuit.

In another aspect, the controller 114 can receive data from an input device 118 (shown as a touch screen), transmit data to an output device 120, and/or exchange data with a control panel (not shown). The input device 118 can include a keyboard, a mouse, a stylus, a touch screen, a push button, a switch, a potentiometer, a scanner, an audio component such as a microphone, or any other device suitable for accepting user input. The output device 120 can include a display or touch screen, a printer, video monitor, a medium reader, an audio device such as a speaker, any combination thereof, and any other device or devices suitable for providing user feedback.

In the embodiment of FIG. 1, the output device 120 is a touch screen that functions as both an input device 118 and an output device 120. The control panel can include visual indicator devices or controls (e.g., indicator lights, numerical displays, etc.) and/or audio indicator devices or controls. The control panel may be a component separate from the input device 118 and/or output device 120, may be integrated with one or more of the devices, may be partially integrated with one or more of the devices, may be in another location, and so on. In alternative examples, the control panel, input device 118, output device 120, or parts thereof (described herein) may be contained in, attached to, or integrated with the applicator 104. In this example, the controller 114, power supply 110, control panel, treatment unit 106, input device 118, and output device 120 are carried by a rack 124 with wheels 126 for portability. In alternative embodiments, the controller 114 can be contained in, attached to, or integrated with the multi-modality applicator 104 and/or the patient protection device described above. In yet other embodiments, the various components can be fixedly installed at a treatment site. Further details with respect to components and/or operation of applicators 104, treatment units 106, and other components may be found in commonly-assigned U.S. Patent Publication No. 2008/0287839.

In operation, and upon receiving input to start a treatment protocol, the controller 114 can cause one or more power supplies 110, one or more treatment units 106, and one or more applicators 104 to cycle through each segment of a prescribed treatment plan. In so doing, power supply 110 and treatment unit 106 provide coolant and power to one or more functional components of the applicator 104, such as thermoelectric coolers (e.g., TEC "zones"), to begin a cooling cycle and, for example, activate features or modes such as vibration, massage, vacuum, etc.

Using temperature sensors (not shown) proximate to the one or more applicators 104, the patient's skin, a patient protection device, or other locations or combinations thereof, the controller 114 can determine whether a temperature or heat flux is sufficiently close to the target temperature or heat flux. It will be appreciated that while a region of the body (e.g., adipose tissue) has been cooled or heated to the target temperature, in actuality that region of the body may be close but not equal to the target temperature, e.g., because of the body's natural heating and cooling variations. Thus, although the system may attempt to heat or cool the tissue to the target temperature or to provide a target heat flux, a sensor may measure a sufficiently close temperature or heat flux. If the target temperature has not been reached, power can be increased or decreased to change heat flux to maintain the target temperature or "set-point" selectively to affect lipid-rich subcutaneous adipose tissue.

When the prescribed segment duration expires, the controller 114 may apply the temperature and duration indicated in the next treatment profile segment. In some embodiments, temperature can be controlled using a variable other than or in addition to power.

In some embodiments, heat flux measurements can indicate other changes or anomalies that can occur during treatment administration. For example, an increase in temperature detected by a heat flux sensor can indicate a freezing event at the skin or underlying tissue (i.e., dermal tissue). An increase in temperature as detected by the heat flux sensors can also indicate movement associated with the applicator, causing the applicator to contact a warmer area of the skin, for example. Methods and systems for collection of feedback data and monitoring of temperature measurements are described in commonly assigned U.S. Pat. No. 8,285,390.

The applicators 104 may also include additional sensors to detect process treatment feedback. Additional sensors may be included for measuring tissue impedance, treatment application force, tissue contact with the applicator and energy interaction with the skin of the subject 101 among other process parameters.

In one embodiment, feedback data associated heat removal from lipid-rich cells in the cutaneous or subcutaneous layer can be collected in real-time. Real-time collection and processing of such feedback data can be used in concert with treatment administration to ensure that the process parameters used to alter or reduce subcutaneous adipose tissue are administered correctly and efficaciously.

Examples of the system 100 may provide the applicator 104 which damages, injures, disrupts or otherwise reduces lipid-rich cells generally without collateral damage to non-lipid-rich cells in the treatment region. In general, it is believed that lipid-rich cells selectively can be affected (e.g., damaged, injured, or disrupted) by exposing such cells to low temperatures that do not so affect non-lipid-rich cells. Moreover, as discussed above, a cryoprotectant can be administered topically to the skin of the subject 101 at the treatment site and/or used with the applicator 104 to, among other advantages, assist in preventing freezing of the non-lipid-rich tissue (e.g., in the dermal and epidermal skin layers) during treatment to selectively interrogate lipid-rich cells in the treatment region so as to beneficially and cosmetically alter subcutaneous adipose tissue, treat sweat glands, and/or reduce sebum secretion. As a result, lipid-rich cells, such as subcutaneous adipose tissue and glandular epithelial cells, can be damaged while other non-lipid-rich cells (e.g., dermal and epidermal skin cells) in the same region are generally not damaged even though the non-lipid-rich cells at the surface may be subject to even lower temperatures. In some embodiment, the mechanical energy provided by the applicator 104 may further enhance the effect on lipid-rich cells by mechanically disrupting the affected lipid-rich cells. In one mode of operation, the applicator 104 may be configured to be a handheld device such as the device disclosed in commonly-assigned U.S. Pat. No. 7,854,754.

Applying the applicator 104 with pressure or with a vacuum type force to the subject's skin or pressing against the skin can be advantageous to achieve efficient treatment. In general, the subject 101 has an internal body temperature of about 37° C., and the blood circulation is one mechanism for maintaining a constant body temperature. As a result, blood flow through the skin and subcutaneous layer of the region to be treated can be viewed as a heat source that counteracts the cooling of the subdermal fat. As such, cooling the tissue of interest requires not only removing the heat from such tissue but also that of the blood circulating through this tissue. Thus, temporarily reducing or eliminating blood flow through the treatment region, by means such as, e.g., applying the applicator with pressure, can improve the efficiency of tissue cooling and avoid excessive heat loss through the dermis and epidermis. Additionally, a vacuum can pull skin away from the body which can assist in cooling targeted underlying tissue.

Figure 2:
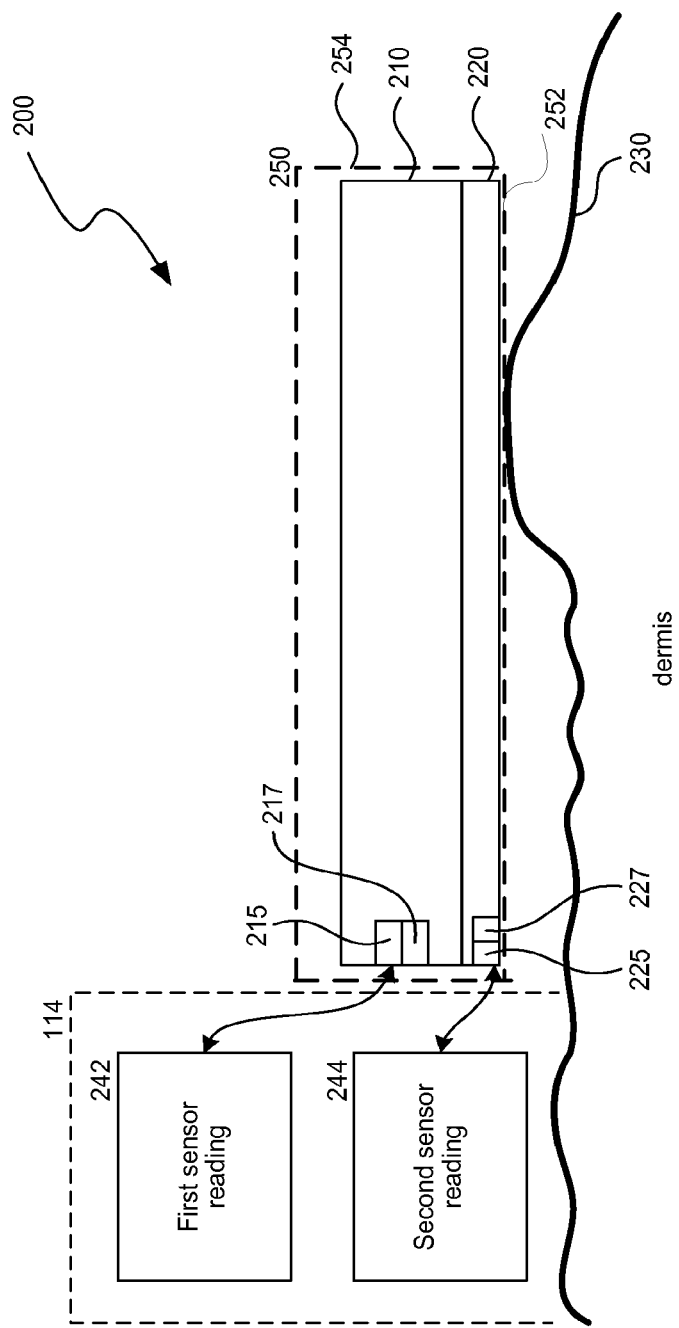
FIG. 2 is a partial cross-sectional view illustrating an applicator suitable to be used in the system of FIG. 1 in accordance with embodiments of the technology.

FIG. 2 is a schematic, cross-sectional view illustrating a treatment device or applicator 200 for non-invasively removing heat from subcutaneous lipid-rich target areas of the subject 101 (FIG. 1) in accordance with an embodiment of the present technology. The applicator 200 can include a heat-exchanging unit (e.g., a cooling unit), such as a heat-exchanging plate 210, and an interface layer 220. In one embodiment, the heat-exchanging plate 210 is associated with one or more Peltier-type TEC elements supplied with coolant and power from the treatment unit 106 (FIG. 1).

The heat-exchanging plate 210 can contain a communication component 215 that communicates with the controller 114 to provide a first sensor reading 242 as described herein, and a sensor 217 that measures, e.g., temperature of the heat-exchanging plate 210, heat flux across a surface of or plane within the heat-exchanging plate 210. The interface layer 220 can be a plate, a film, a covering, a sleeve, a cryoprotectant reservoir or other suitable materials described herein and may serve as the patient protection device described herein. The interface layer 220 is located between the heat-exchanging plate 210 and the skin 230 of a subject 101 (FIG. 1), such as the skin of a patient receiving treatment via the treatment system 100 and applicator 104 (FIG. 1). Other interface layers may be present.

The interface layer 220 can also contain a similar communication component 225 that communicates with the controller 114 to provide a second sensor reading 244 and a sensor 227 that measures, e.g., the temperature of the interface layer 220, heat flux across a surface of or plane within the interface layer 220 or contact pressure with the skin 230 of the patient. For example, one or both of the communication components 215, 225 can receive and transmit information from the controller 114, such as temperature and/or heat flux information as determined by one or both of the sensors 217, 227. The sensors 217, 227 are configured to measure a parameter of the interface without substantially impeding heat transfer between the heat-exchanging plate 210 and the subject's skin 230. The applicator 200 can also contain power components and other components described with respect to FIG. 1 and related applications.

In certain embodiments, the applicator 200 can include a sleeve 250 or liner for contacting the patient's skin 230, for example, to prevent direct contact between the applicator 200 and the patient's skin 230, and thereby reduce the likelihood of cross-contamination between patients, minimize cleaning requirements for the applicator 200, etc. The sleeve 250 can include a first sleeve portion 252 and a second sleeve portion 254 extending from the first sleeve portion. The first sleeve portion 252 can contact and/or facilitate the contact of the applicator 200 with the patient's skin 230, while the second sleeve portion 254 can be an isolation layer extending from the first sleeve portion 252. The second sleeve portion 254 can be constructed from latex, rubber, nylon, Kevlar®, or other substantially impermeable or semi-permeable material. The second sleeve portion 254 can prevent contact between the patient's skin 230 and the heat-exchanging plates 210, among other things.

Further details regarding a patient protection device may be found in U.S. Patent Publication No. 2008/0077201.

In other embodiments, the applicator 200 can include a belt (not shown) that assists in forming a contact between the applicator 200 (such as via an interface layer 220) and the patient's skin 230. For example, the applicator 200 can include retention devices (not shown) coupled to a frame. The retention devices may be rotatably connected to the frame by a plurality of coupling elements that can be, for example, pins, ball joints, bearings, or other type of rotatable joints. Alternatively, the retention devices can be rigidly affixed to the end portions of heat-exchanging element housings. Further details regarding a suitable belt device may be found in U.S. Patent Publication No. 2008/0077211.

In further embodiments, the applicator 200 can include a vacuum (not shown) that assists in forming a contact between the applicator 200 (such as via the interface layer 220 or sleeve 250) and the patient's skin 230. For example, the applicator 200 can provide mechanical energy to a treatment region. Imparting mechanical vibratory energy to the patient's tissue by repeatedly applying and releasing a vacuum to the subject's tissue, for instance, creates a massage action during treatment. Further details regarding a vacuum type device may be found in U.S. Patent Application Publication No. 2008/0287839.

Figure 3:
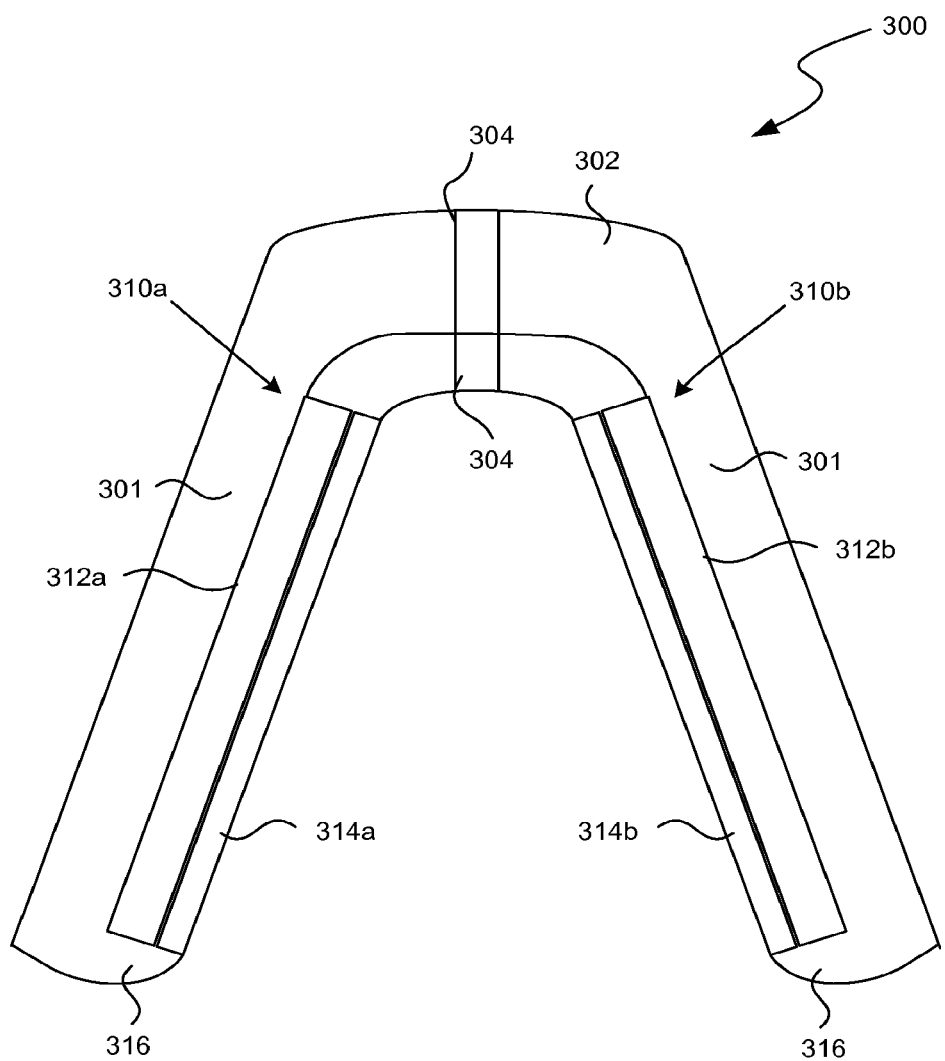
FIG. 3 is a partial cross-sectional view illustrating an applicator suitable to be used in the system of FIG. 1 in accordance with another embodiment of the technology.

FIG. 3 is a schematic cross-sectional view of an applicator 300 for non-invasively removing heat from subcutaneous lipid-rich target areas of the subject 101 (FIG. 1) in accordance with another embodiment of the technology. The applicator 300 includes a housing 301 having a vacuum cup 302 with a vacuum port 304 disposed in the vacuum cup 302. The housing 301 is coupled to or otherwise supports a first applicator unit 310a on one side of the cup 302, and a second applicator unit 310b on an opposing side of the cup 302. Each of the first and second applicator units 310a and 310b can include a heat-exchanging unit (e.g., a cooling unit), such as a heat-exchanging plate 312 (shown individually as 312a and 312b), and an interface layer 314 (shown individually as 314a and 314b). In one embodiment, the heat-exchanging plate 312 is associated with one or more Peltier-type TEC elements supplied with coolant and power from the treatment unit 106 (FIG. 1). As such, the heat-exchanging plates 312a, 312b can be similar to the heat-exchanging plate 210 described above with reference to FIG. 2.

The interface layers 314a and 314b are adjacent to the heat-exchanging plates 312a and 312b, respectively. Similar to the interface layer 220 illustrated in FIG. 2, the interface layers 314a and 314b can be plates, films, a covering, a sleeve, a cryoprotectant reservoir or other suitable materials located between the heat-exchanging plates 312a and 312b and the skin (not shown) of a subject. In one embodiment, the interface layers 314a and 314b can serve as patient protection devices as described herein. The interface layers 314a and 314b can include communication components (not shown) and sensors (not shown) similar to those described with respect to the interface layer 220 of FIG. 2 for communicating with the controller 114 (FIG. 1).

In operation, the rim 316 of the vacuum cup 302 is placed against the skin of a subject (not shown) and a vacuum is drawn within the cup 302. The vacuum pulls the tissue of the subject into the cup 302 and coapts the target area with the interface layers 314a and 314b of the corresponding first and second applicator units 310a, 310b. One suitable vacuum cup 302 with cooling units is described in U.S. Pat. No. 7,367,341.

The applicator units 310a and 310b can be in communication with the controller 114, treatment unit 106, energy-generating unit 107, if present, and power supply 110 (FIG. 1) such that the heat-exchanging plates 312a, 312b can provide cooling or other energy to the target region based on a predetermined or real-time determined treatment protocol. For example, the heat-exchanging plates 312a, 312b can first be cooled to cool the adjacent tissue of the target region to a temperature below 37° C. (e.g., to a temperature in the range of between about −20° C. to about 20° C.). The heat-exchanging plates 312a, 312b can be cooled using Peltier devices, cooling channels (e.g., channels through which a chilled fluid flows), cryogenic fluids, or other similar cooling techniques. In one embodiment, the heat-exchanging plates 312a, 312b are cooled to a desired treatment temperature (−20° C., −18° C., −15° C., −10° C., 0° C.) to cool subcutaneous lipid-rich cells. The lipid-rich cells can be maintained at a sufficiently low temperature to damage or destroy the lipid rich cells.

Referring back to FIGS. 1-3 together and in some examples of the system 100, the treatment device or applicator may be used with a substance that may (a) provide a thermal coupling between the subject's skin and the heat-exchanging unit(s) or plates to improve heat transfer therebetween; and/or (b) protect biological tissues of a subject from freezing damage (e.g., damage due to ice formation). The substance may be a fluid, e.g., a liquid, a gel, or a paste, which may be hygroscopic, thermally conductive, and biocompatible.

Some embodiments according to the present technology may use a cryoprotectant including a freezing point depressant that can assist in preventing freezing of non-lipid-rich tissue (e.g., dermal and epidermal tissue) during treatment. Suitable cryoprotectants and processes for implementing cryoprotectants are described herein and in commonly-assigned U.S. Patent Publication No. 2007/0255362. The freezing point depressant can be part of a cryoprotectant that may additionally include a thickening agent, a pH buffer, a humectant, a surfactant, and/or other additives and adjuvants as described herein. The freezing point depressant may include, for example, propylene glycol (PG), polyethylene glycol (PEG), dimethyl sulfoxide (DMSO), or other suitable alcohol compounds. In a particular embodiment, a cryoprotectant may include about 40% propylene glycol and about 60% water. In other embodiments, a cryoprotectant may include about 30% propylene glycol, about 30% glycerin (a humectant), and about 40% ethanol. In another embodiment, a cryoprotectant may include about 40% propylene glycol, about 0.8% hydroxyethyl cellulose (a thickening agent), and about 59.2% water. In a further embodiment, a cryoprotectant may include about 50% polypropylene glycol, about 40% glycerin, and about 10% ethanol. In yet a further embodiment, the cryoprotectant can include about 30-50% by volume of one or more freezing point depressants and include about 50% wt./vol. to about 70% wt./vol. of a combination of one or more of a thickening agent, a pH buffer, a humectant, a surfactant, and one more additives that (a) facilitate permeation of the cryoprotectant into the epidermis and dermis, (b) increase an intracellular concentration of solutes of dermal and epidermal cells, (c) form a hypertonic cryoprotectant formulation and/or (d) hydrophilic and/or lipophobic molecules.

The cryoprotectant may also provide a means of reducing friction at the interface between the patient's skin and the treatment device or applicator. This is expected to improve the draw of tissue against the applicator, thereby providing a more complete and effective treatment. By way of example, in one specific treatment process, an interface member is placed directly over the target area of the patient, and the applicator 104, 200, 300 with a disposable sleeve or liner is placed in contact with the interface member for treatment. The interface member can be a reservoir containing a desired volume of cryoprotectant. The interface member can include, for example, a non-woven cotton fabric pad saturated with the cryoprotectant. Suitable pads include Webril™ pads manufactured by Covidien of Mansfield, Mass. Further details regarding the interface member and associated systems and methods are described in commonly-assigned U.S. Patent Publication No. 2010/0280582. In other embodiments, however, the interface member can include other suitable pads or devices.

Without being bound by theory, it is believed that effective conductive cooling from the treatment device or applicator 104 depends on a number of factors. Examples of factors that impact heat removal or extraction from the skin and related tissue include, for example, the surface area of the treatment unit, the temperature of the interface member, the mechanical energy delivered to the tissue, the distribution of cryoprotectant, and the extent of non-uniformities in the contact between the interface member and the skin.

E. Structures for Sustained and/or Replenishing Release of Cryoprotectant

Figure 4:
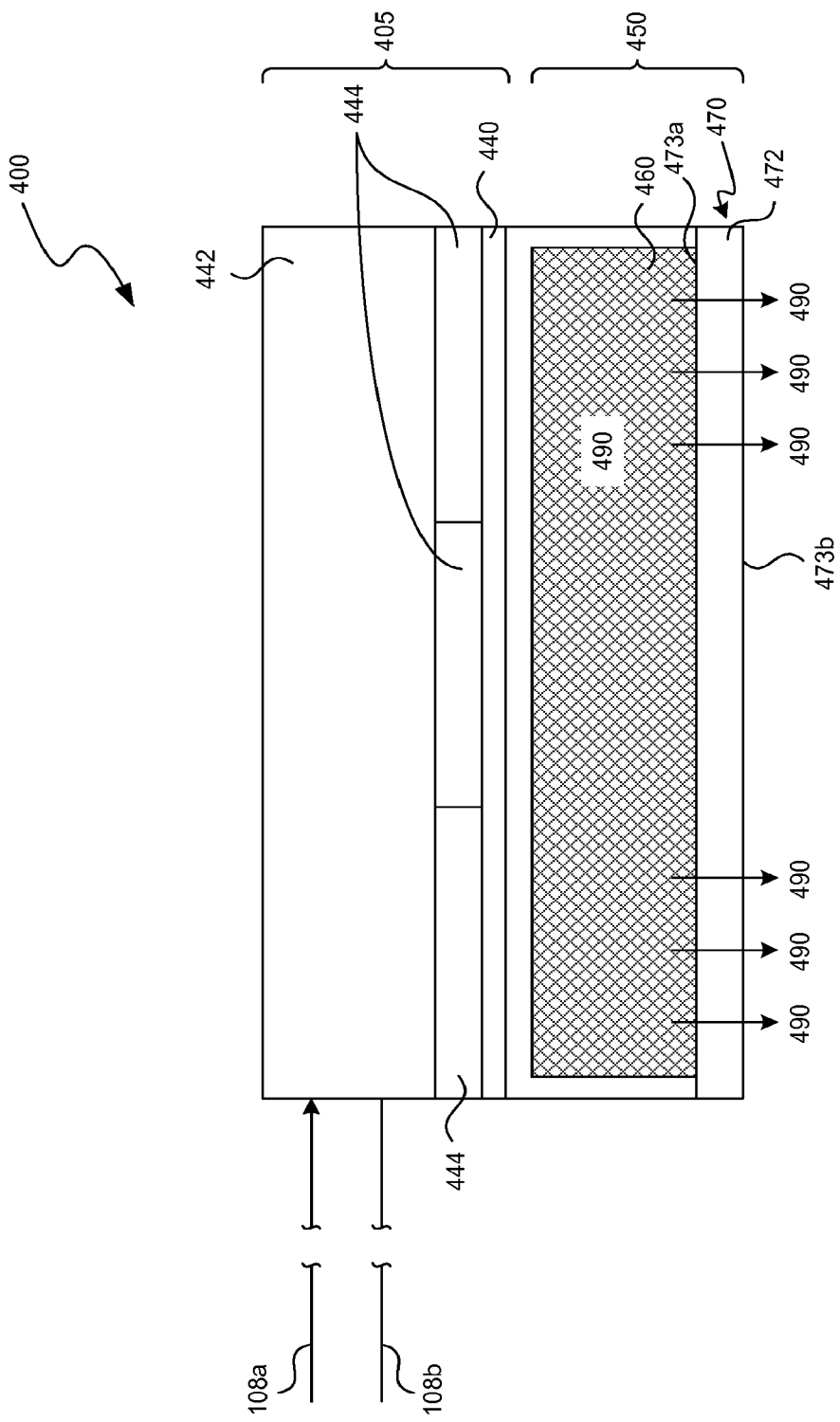
FIG. 4 is a partial cross-sectional view illustrating an applicator suitable to be used in the system of FIG. 1 in accordance with a further embodiment of the technology.

Several embodiments of the system can include structures for enhancing sustained and/or replenishing release of cryoprotectant to a treatment site. In some embodiments, such sustained release structures can be incorporated within the interface member. For example, FIG. 4 is an enlarged schematic cross-sectional view of another applicator 400 in accordance with another aspect of the present technology. For purposes of illustration, a number of components of the applicator 400 are not shown or described. The applicator 400 includes (a) an interface assembly 450 configured to contact the target area, and (b) a cooling unit 405. In this embodiment, the cooling unit 405 is a component of a cooling system integrated with the applicator 400. The cooling unit 405 can include a plate 440 having a high thermal conductivity, a coolant chamber 442, and one or more Peltier-type thermoelectric elements 444, such as a plurality of individually controlled thermal segments that create a custom spatial cooling profile and/or a time-varying cooling profile. Each custom treatment profile can include one or more segments, and each segment can include a specified duration, a target temperature, and control parameters for features such as vibration, massage, vacuum, and other treatment modes. Cooling devices having multiple individually controlled heat-exchanging units are described, e.g., in commonly assigned U.S. Patent Publication No. US 2008/0077211.

A coolant can circulate through the coolant chamber 442 via supply and return 108a and 108b, respectively, and the thermoelectric elements 444 can selectively heat and/or cool relative to the temperature of the coolant in the coolant chamber 442 to control the temperature over relatively large areas of the cooling plate 440. Other embodiments of the cooling unit 405 do not include the thermoelectric elements 444 such that the coolant chamber 442 extends to the plate 440. In either case, the cooling unit 405 provides a heat sink that cools the interface assembly 450. In still other embodiments, the cooling unit 405 may have a different arrangement and/or different features.

The interface assembly 450 of the applicator 400 further controls the heat flux through a plurality of smaller zones and delivers a freezing point depressant composition (e.g., cryoprotectant) to the target area. In the illustrated embodiment, the interface assembly 450 includes a cryoprotectant container 460 that contains a cryoprotectant 490, and an interface element 470 through which the cryoprotectant 490 can flow. The reservoir 460 is configured to provide a continuous or at least an approximately continuous supply of cryoprotectant 490 to the target area during treatment. In other embodiments, the cryoprotectant 490 may be applied directly to an engagement surface of the applicator 400, the skin of the subject 101, or both, in addition to or in lieu of supplying the cryoprotectant 490 via the container 460.

The interface element 470 can include a contact member 472 having a back side 473a in contact with the cryoprotectant 490 and a front side 473b configured to contact the epidermis of the subject and/or an interface member on the subject's skin. The contact member 472 can be a flexible barrier (e.g., membrane), a mesh, fabric or other suitable material through which the cryoprotectant 490 can flow from the back side 473a to the front side 473b. In other embodiments, the contact member 472 can be a substantially rigid barrier that is thermally conductive and configured to allow the cryoprotectant 490 to pass from the back side 473a to the front side 473b. A rigid contact member, for example, can be a plate with holes or a panel made from a porous metal material. In other embodiments, the interface element 470 can have a different arrangement and/or include different features.

Referring to FIGS. 1 and 4 together, the treatment unit 106 (FIG. 1) may be a refrigeration unit, a cooling tower, a thermoelectric chiller or cooler or any other device or cooling unit capable of removing heat from a coolant in addition to or in lieu of the cooling unit 405 (FIG. 4) at the applicator 400. The treatment unit 106 can be operatively coupled to the applicator 400 by supply and return fluid lines 108a and 108b that circulate chilled fluid (e.g., a coolant) through the applicator 400. Alternatively, the treatment unit 106 can circulate warm fluid to the applicator 400 during periods of warming. Furthermore, one skilled in the art will recognize that there are a number of other cooling technologies that could be used such that the cooling units or coolers of the treatment unit 106 or the applicator 400 need not be limited to those described herein.

Figure 5:
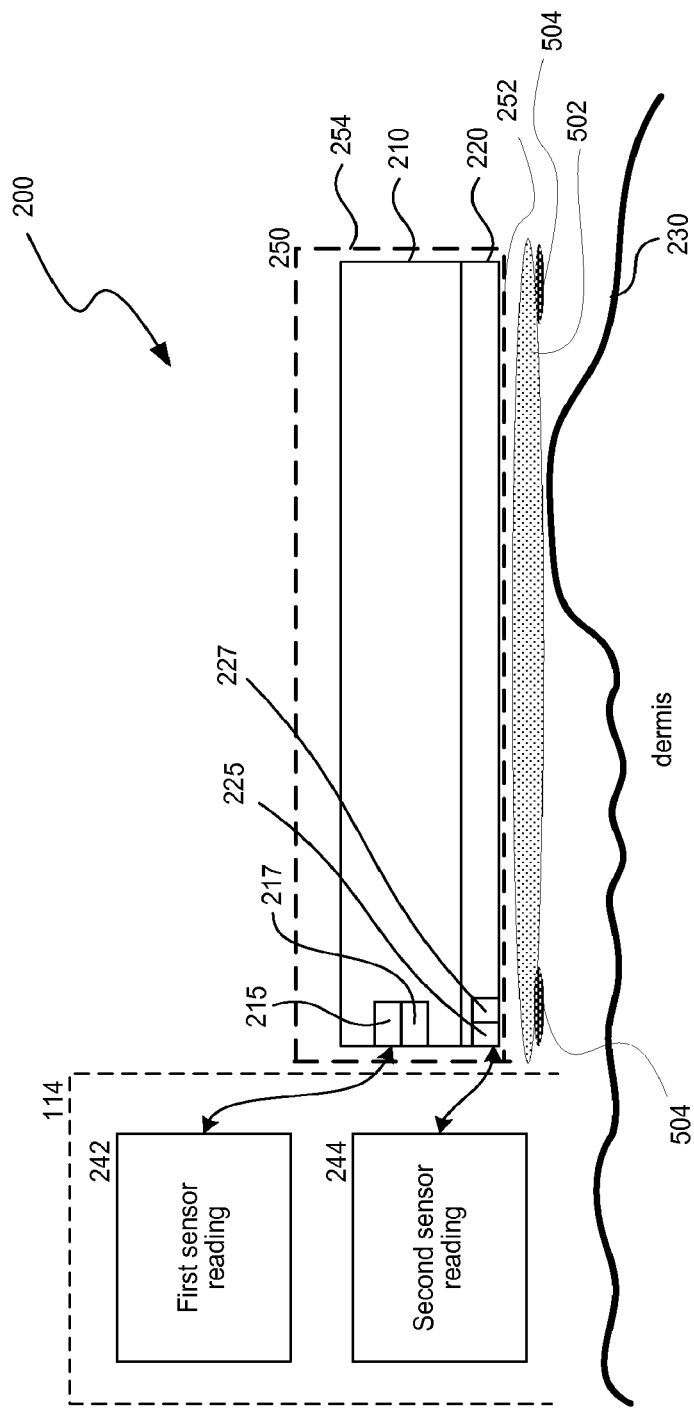
FIG. 5 is a partial cross-sectional view illustrating the applicator of FIG. 2 and a freezing depressant release structure suitable to be used in the system of FIG. 1 in accordance with yet another embodiment of the technology.

In accordance with other aspects of the present disclosure sustained and/or replenishing release of freezing point depressant compositions (e.g., cryoprotectant) can be provided by structures separate from or in lieu of the interface member. For example, FIG. 5 is a schematic, cross-sectional view illustrating the treatment device or applicator 200 of FIG. 2 and having a cryoprotectant release structure 502 in accordance with an embodiment of the present technology. The cryoprotectant release structure 502 can be configured to absorb and/or otherwise hold a freezing point depressant composition (e.g., cryoprotectant) and release the composition in a time dependent manner to the skin 230 of the subject and/or the applicator 200. Accordingly, the release structure 502 can be configured to be placed on the skin 230 of the subject at the targeted treatment site prior to the placement of the applicator 200. In another embodiment, the release structure 200 can be adhered to the applicator 200 such that it comes in contact with the skin 230 of the subject as the applicator 200 is positioned at the treatment site.

In some embodiments, the cryoprotectant release structure 502 can be configured to continuously or periodically release cryoprotectant. The release rate of cryoprotectant can be related to the absorption and/or dispersion rate of the cryoprotectant. In one embodiment, the cryoprotectant release structure 502 can deliver cryoprotectant at a generally constant rate throughout most or all of the treatment process. In other embodiments, the cryoprotectant release structure 502 can maintain contact between the subject's skin 230 and the cryoprotectant. The subject's skin 230 can absorb the cryoprotectant to prevent or limit damage to non-targeted tissue.

The cryoprotectant release structure 502, in some embodiments, can continuously deliver cryoprotectant for a duration of time equal to or greater than about 15 minutes, about 20 minutes, about 30 minutes, 1 hour, or 2 hours. The cryoprotectant release structure 502 can be replaced for longer treatments. In other embodiments, the release structure 502 can be configured to be reloadable during treatment so that, for example, the release structure 502 can continue to deliver cryoprotectant for a longer duration of time.

In one embodiment, the release structure 502 can include an absorbent containing a bioabsorbable freezing point depressant (e.g., a cryoprotectant). The absorbent can be constructed from cotton material and/or gauze material and the freezing point depressant can be absorbed on and/or therein. In some embodiments, and while the subject is being treated, the absorbent can be positioned between the subject's skin 230 and a heat-exchanging surface of a treatment device or applicator 200. A liner or protective sleeve (e.g., sleeve 250) may be positioned between the absorbent and the applicator 200 to shield the applicator and to provide a sanitary barrier that is, in some embodiments, inexpensive and thus disposable.

In another embodiment, the release structure 502 can be a microporous or gel pad. For example, the freezing point depressant (e.g., cryoprotectant) can be absorbed or delivered within the microporous or gel pad that is positioned between the subject's skin 230 and a heat-exchanging surface of a treatment device or applicator 200. The gel pad can release the cryoprotectant to the subject's skin either prior to or during treatment. In some embodiments, the microporous gel pad can continually release quantities of freezing point depressant over time and/or during a treatment session. In some embodiments, the freezing point depressant can be released at higher concentrations, higher volumes and/or at more controlled rates than by conventional spreading the cryoprotectant on the skin 230 of the subject.

In a further embodiment, the release structure 502 can include an adhesive 504 (e.g., tape strips, textile tapes, etc.), such that the release structure 502 can be releasably retained on the surface of the skin 230 at the treatment site. In one embodiment, the adhesive 504 can be on a bottom surface of the release structure 502 such that when the release structure 502 is placed on a surface of the skin 230 at the treatment site, the release structure 502 is adhered to the skin 230. In several embodiments, the adhesive 504 can prevent slipping or moving of the release structure 502 while positioning the applicator 200 and/or during treatment. In one embodiment, the adhesive 504 can be positioned around an outside perimeter of the release structure 502 and be configured to retain the release structure 502 at the treatment site while preventing cryoprotectant from leaking or spreading to a surface of the skin 230 adjacent to but outside of the treatment site. Accordingly, in such embodiments, the cryoprotectant is retained or sealed against the surface of the skin 230 at the treatment site.

In other embodiments, the adhesive 504 can include layers of adhesive material that can store freezing point depressant compositions and release quantities of freezing point depressant to the surface of the skin 230. Such adhesive layers may include silicone gels, waxes, hydrocarbon resins, terpene-phenol resins, as well as natural and synthetic resins. In some embodiments, adhesive layers can provide cryoprotectant to the surface of the skin 230 at higher volumes and/or at more controlled rates than by conventional means.

Although a noninvasive applicator unit is illustrated and discussed with respect to FIGS. 2-5, minimally invasive applicators may also be employed. In such a case, the applicator and patient protection device may be integrated. As an example, a cryoprobe and/or electrode that may be inserted directly into the subcutaneous adipose tissue to cool or freeze the tissue is an example of such a minimally invasive applicator. Cryoprobes manufactured by, e.g., Endocare, Inc., of Irvine, Calif. are suitable for such applications. This patent application incorporates by reference U.S. Pat. No. 6,494,844, entitled "DEVICE FOR BIOPSY AND TREATMENT OF BREAST TUMORS"; U.S. Pat. No. 6,551,255, entitled "DEVICE FOR BIOPSY OF TUMORS"; U.S. Publication No. 2007/0055173, entitled "ROTATIONAL CORE BIOPSY DEVICE WITH LIQUID CRYOGEN ADHESION PROBE"; U.S. Pat. No. 6,789,545, entitled "METHOD AND SYSTEM FOR CRYOABLATING FIBROADENOMAS"; U.S. Publication No. 2004/0215294, entitled "CRYOTHERAPY PROBE"; U.S. Pat. No. 7,083,612, entitled "CRYOTHERAPY SYSTEM"; and U.S. Publication No. 2005/0261753, entitled "METHODS AND SYSTEMS FOR CRYOGENIC COOLING".

The treatment device or applicator, the cryoprotectant, and/or other components of the treatment system 100 can be included in a kit (not shown) for removing heat from cutaneous or subcutaneous lipid rich cells of the subject 101. The kit can also include instruction documentation containing information regarding how to (a) apply the composition to a target region and/or a heat-exchanging surface of the treatment device or applicator and (b) reduce a temperature of the target region such that lipid rich cells in the region are affected while preserving non-lipid rich cells proximate to the heat-exchanging surface. In other embodiments, the kit can include pre-treatment and/or post-treatment compositions. The kit can further include one or more dermatological pre-treatment and/or post-treatment components such as a dermal agitation brush, cleaning solutions and pads, gauze, bandages, etc.

F. Additional Pre-Treatment Methods and Compositions

Prior to the introduction of cooling treatment, the treatment site can be pretreated to facilitate or enhance cooling of lipid-rich cells, prevent freezing of non-lipid-rich tissue layers and/or facilitate efficacy of freezing point depressant (e.g., cryoprotectant) formulations applied to the skin of the subject at the treatment site. For example, pre-treatment of the treatment site can enhance the effect of a freezing point depressant. In some embodiments, the first composition can be applied to pre-treat the treatment site to facilitate permeability of the skin to the freezing point depressant.

In operation, one embodiment according to the present technology may include preparing a target area for treatment by topically applying to the patient's skin a pad, e.g., Webril™ manufactured by Covidien, which is saturated with thermal coupling fluid such as a cryoprotectant gel including a temperature or freezing point depressant. The pad can be placed at the treatment site for a period of time (e.g., about 1 minute to about 5 minutes, about 1 minute to about 2 minutes, about 5 minutes to about 10 minutes, less than about 10 minutes, less than about 5 minutes, etc.) prior to commencing cooling treatment with a treatment device. In some embodiments, the pad can be at a natural body surface temperature (e.g., 30° C.-34° C.), at an internal body temperature (e.g., 37° C.) or warmer prior to positioning the pad at the treatment site.

Figure 6:
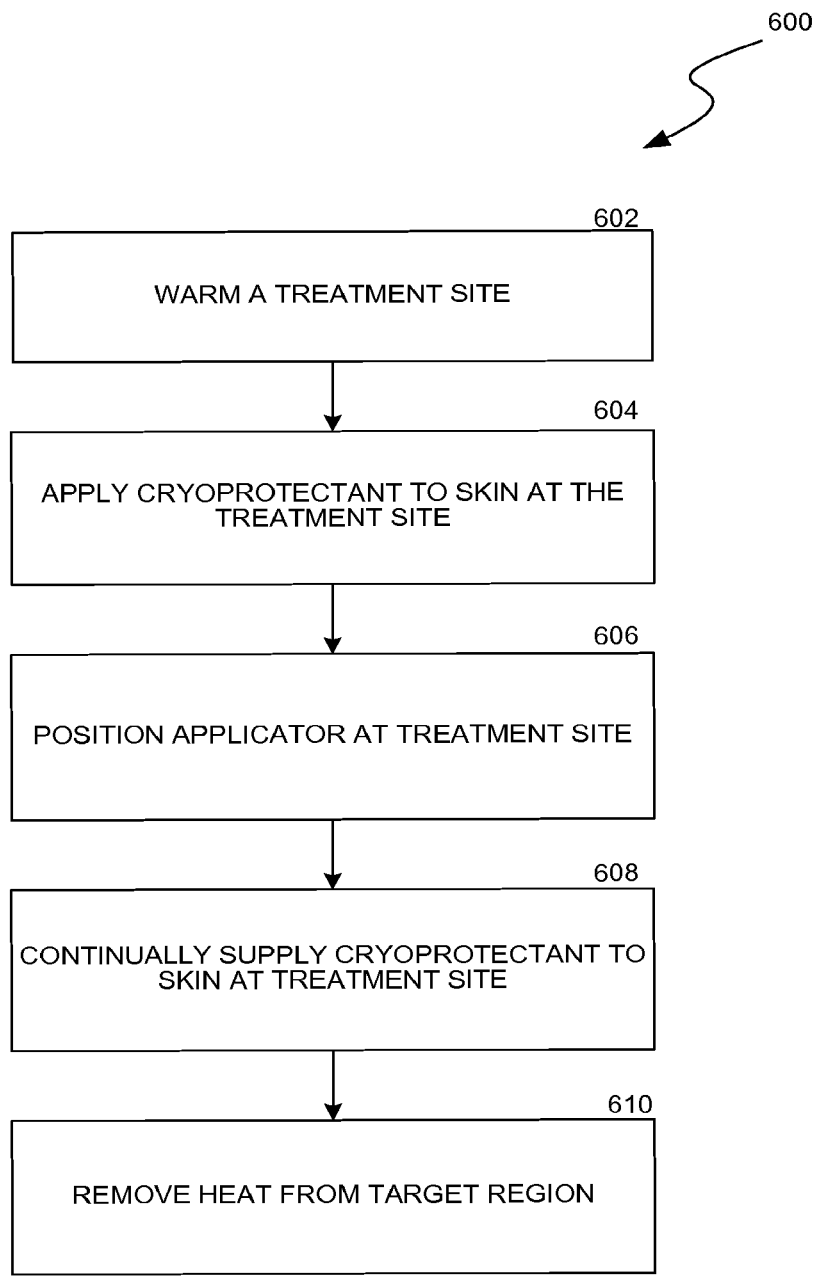
FIG. 6 is a flow diagram illustrating a method for pre-treating a target site prior to cooling the target site in accordance with an embodiment of the technology.

In another embodiment, heat can be applied to the treatment site prior to introduction of cooling treatment for the destruction or alteration of lipid-rich cells. FIG. 6 is a flow diagram illustrating a method 600 for pre-treating a target site using heat prior to cooling the target site in accordance with an embodiment of the present technology. Even though the method 600 is described below with reference to the treatment system 100 of FIG. 1 and the applicators 104, 200, 300 and 400 of FIGS. 1, 2, 3 and 4, respectively, the method 600 may also be applied in other treatment systems with additional or different hardware and/or software components.

As shown in FIG. 6, the method 600 can include warming the treatment site (block 602) and applying a freezing point depressant (block 604). For example, a surface of a heating element can warm the upper layers (e.g., epidermal and dermal layers) of the treatment site prior to applying a freezing point depressant (e.g., cryoprotectant). Alternatively, the freezing point depressant can be heated prior to applying the composition to the treatment site. Without being bound by theory, it is believed that higher temperatures may potentially facilitate greater cryoprotectant loading, absorption rates, and/or retention in the epidermal and dermal layers above the lipid-rich cells of the target region. In one embodiment, pre-heating the upper layers of the skin (e.g., the non-lipid rich cells) can increase the skin permeability to freezing point depressant formulations. In some embodiments, warming of the treatment region would facilitate use of cryoprotectants having higher viscosities (e.g. >10,000 cP) at low temperatures (e.g. about 5° C. to about −15° C., 20° C. to about −20° C.). In one embodiment, the epidermis and/or dermis layers can be warmed to a temperature of between about 25° C. to about 45° C., about 25° C. to about 40° C., about 25° C. to about 35° C., about 26° C. to about 30° C., or about 35° C. to about 45° C. (e.g., about 40° C.). In other embodiments, the surface of the skin can warmed to about 30° C. to about 40° C.

In various embodiments, heat can be applied to the treatment site prior to introduction of cooling for a predetermined period of time prior to the introduction of cooling treatment. For example, heat can be applied to the treatment site for about 1 minute to about 30 minutes. In another embodiment, heat can be applied to the treatment site for about 15 minutes, about 20 minutes, about 30 minutes or greater than 30 minutes.

Following warming of the upper layers of the skin, freezing point depressant (e.g., cryoprotectant) can be applied topically to the skin of the treatment site by administering a volume of cryoprotectant in a liquid or gel form, for example, directly to the skin. For example, applying the cryoprotectant may include spraying or smearing the cryoprotectant onto the skin using an instrument including, e.g., a spatula, a spray bottle or syringe, or by an operator's gloved hand. In another embodiment, a pad having cryoprotectant absorbed therein can be placed on the skin of the subject at the treatment site.

The method 600 can continue by positioning one or more applicators on the subject (block 606). For example, surfaces of the applicator unit(s) can couple with the surface of the subject's skin at a target region. In one embodiment, the applicator unit can include a heat-exchanging unit, a heat-exchanging plate or cooling plate. In another embodiment, the surface of the applicator unit can be the surface of an interface layer or a patient protection sleeve/liner. Coupling of the surface(s) of the applicator unit(s) to the surface of the skin can be facilitated by using restraining means, such as a belt or strap. In other embodiments, a force (e.g., vacuum or suction force) can be used to positively couple the subject's skin at the target region to the surfaces.

Additionally, the method 600 can also include continually supplying cryoprotectant to the skin of the subject (block 608). The continually supplied cryoprotectant may maintain a sufficient concentration of absorbed cryoprotectant in the epidermis and/or dermis of the subject at the treatment site for reducing the risk of freezing damage. In one embodiment, a freezing point depressant release structure can be positioned between a subject's skin and the applicator to facilitate sustained and/or replenishing release of the cryoprotectant to the skin during a treatment session. The cryoprotectant composition supplied during a treatment session can be the same composition or, in other embodiments, a different composition than the cryoprotectant composition initially applied in step 604.

The method 600 can also include removing heat from the target region of the subject (e.g., human or animal patient) during a treatment process selectively to cool lipid-rich cells in the target region to a temperature below normal body temperature (block 610). For example, the lipid-rich tissue can be cooled to a temperature below about 37° C., below about 20° C., below about 10° C. or below about 0° C. such that lipid-rich cells are affected without substantially affecting non-lipid-rich cells. In some embodiments, the lipid-rich tissue can be cooled to about −20° C. to about 20° C., to about −18° C. to about 5° C. or to about −15° C. to about 0° C.

Figure 7:
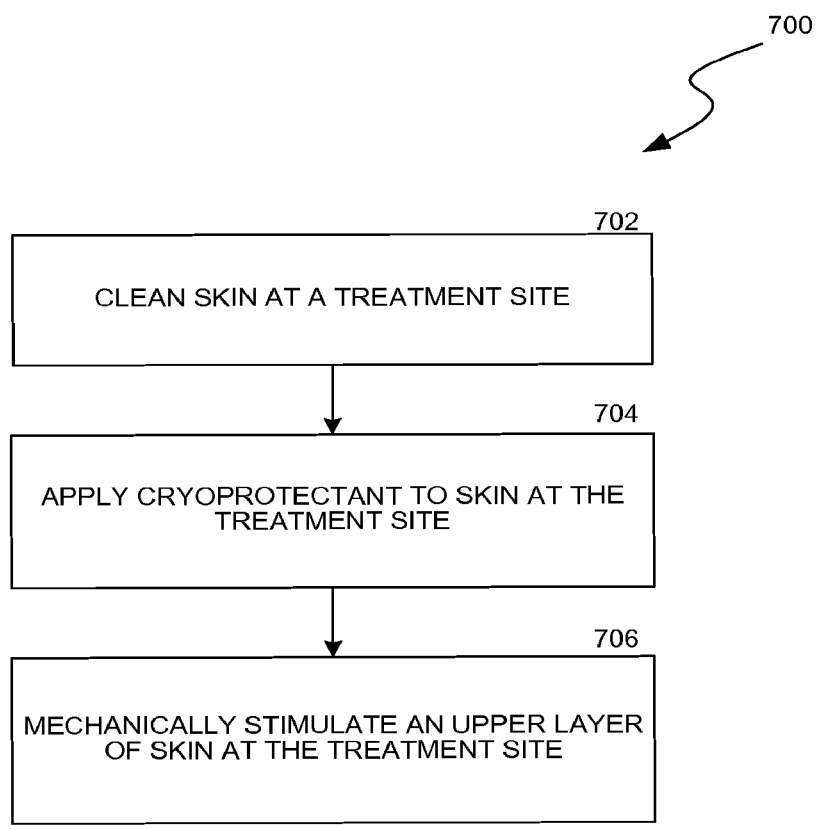
FIG. 7 is a flow diagram illustrating another method for pre-treating a target site using mechanical stimulation in accordance with an embodiment of the technology.

In further embodiments, methods that facilitate uptake (e.g., absorption) of cryoprotectant in the dermal and epidermal skin layers (e.g., across the stratum corneum) prior to or during cooling treatment can also include applying mechanical stimulation/agitation of the skin at the treatment site prior to introduction of cooling treatment for the destruction or alteration of lipid-rich cells. FIG. 7 is a flow diagram illustrating a method 700 for pre-treating a target site using mechanical stimulation of the skin in accordance with an embodiment of the present technology. Even though the method 700 is described below with reference to the treatment system 100 of FIG. 1 and the applicators 104, 200, 300 and 400 of FIGS. 1, 2, 3 and 4, respectively, the method 700 may also be applied in other treatment systems with additional or different hardware and/or software components.

As shown in FIG. 7, the method 700 can, optionally, include cleaning a treatment site to remove oil and/or other debris from the surface of the skin at the treatment site (block 702). The method 700 can also include applying a freezing point depressant (block 704) to the treatment site. In one embodiment, the freezing point depressant (e.g., cryoprotectant) can be applied topically to the skin of the treatment site by administering a volume of cryoprotectant in a liquid or gel form, for example, directly to the skin. For example, applying the cryoprotectant may include spraying, coating or rubbing the cryoprotectant onto the skin using an instrument including, e.g., a spatula, a spray bottle or syringe, or by an operator's gloved hand.

The method 700 can continue with mechanically stimulating the skin at the treatment site (block 706). Mechanical stimulation can include, for example, stimulation or agitation by brushing, rubbing, ultrasound or other means which can cause the barrier of the stratum corneum (i.e., the outermost layer of the epidermis consisting of dead cells) to be temporarily reduced and/or increase movement (e.g., turbulence) of the cryoprotectant with respect to the skin. Without being bound by theory, it is believed that mechanical stimulation of the skin (e.g., agitation of, reduction of, or penetration of the stratum corneum) can enhance the permeation of the cryoprotectant into the underlying epidermal and dermal skin layers. In one embodiment, the skin can be mechanically stimulated (e.g., abrading, brushing, rubbing, etc.) for about 1 minute to about 10 minutes. In another embodiment, mechanical stimulation can be applied to the treatment site for about 1 minute, about 2 minutes, about 5 minutes or greater than 5 minutes. In some embodiments, mechanical stimulation could be performed with, for example, a dermal agitation brush, a brush having rotating bristles, a portion of gauze or the like. Brushing or rubbing the skin can include, in some embodiments, moving across the skin at the treatment site in a circular motion or in other embodiments, in linear strokes.

In other embodiments, mechanical stimulation can include mechanical abrasion of the skin that can induce at least mild exfoliation of the stratum corneum thereby enhancing uptake of the topically applied cryoprotectant. Examples of mechanical abrasion can include vigorous brushing, scrubbing or other related means for causing exfoliation of the skin.

In some embodiments, cryoprotectant could be topically applied following mechanical stimulation of the skin at the treatment site. In further embodiments, aspects of the methods 600 and 700 could be combined to increase uptake of cryoprotectant prior to cooling the treatment site. For example, heat may be applied prior to administering cryoprotectant and these steps could be followed by mechanical agitation of the treatment area to further facilitate uptake of the freezing point depressant in the epidermal and dermal layers of the skin.

Various aspects of the methods 600 and 700 can include a cosmetic treatment method for treating the target region of a human subject's body to achieve a cosmetically beneficial alteration of subcutaneous adipose tissue, a reduction in undesirable sweat secretion, or reduction in sebum secretion. Such a method could be administered by a non-medically trained person.

One expected advantage of several of the embodiments of the methods 600 and 700 is that an operator may use lower treatment temperatures for selectively affecting lipid-rich cells of the subject without causing freezing damage to the dermal and epidermal tissue layers of the subject. The applied freezing point depressant compositions (e.g., cryoprotectant) may lower the freezing point of the skin of the subject or body fluid in the target region to at least reduce the risk of intracellular and/or extracellular ice formation at such low treatment temperatures. Additionally, aspects of the methods 600, 700 enhance loading and/or retention of the cryoprotectant in the epidermal and dermal layers.

Another expected advantage of some of the embodiments of the methods 600 and 700 is that the dermis and/or epidermis of the subject may be continually protected against freezing damage due to the sustaining and/or replenishing administration of cryoprotectant, and/or due to the administration of longer-lasting cryoprotectant formulations disclosed herein.

Additional aspects of the present technology include pre-treatment compositions, which can in some embodiments be a first cryoprotectant composition, that can be applied to the skin of the subject prior to applying a second composition (e.g., a cryoprotectant delivered in conjunction with a system applicator) and initiating cooling treatment. In various embodiments, application of the pre-treatment composition or first cryoprotectant composition, to the skin of the subject prior to application of a second cryoprotectant composition can facilitate an absorption of the freezing point depressant in the first and/or second cryoprotectant compositions. For example, in some embodiments, pre-treatment compositions can enhance skin permeability (e.g., to facilitate cryoprotectant penetration and distribution within the dermis and epidermis of the treatment site). In one embodiment, the pre-treatment composition can be applied to the skin when the skin is at or above a natural body surface temperature (e.g., 30° C.-34° C.) to enhance skin permeability. In another embodiment, the pre-treatment composition can be pre-warmed and applied to the skin at a temperature that is at or above the natural body surface temperature (e.g., 30° C.-34° C.). In one embodiment, a pre-treatment composition can include glycolic acid or other alpha-hydroxy acids. In another embodiment, a pre-treatment composition can contain on or more of: butylene glycol, oleic acid or other fatty acids, d-limonene or related terpenes and terpenoids, N-methyl-2-pyrrolidone, dimethylsulphoxide, 1,3-diphenylurea, dodecyl,N,N-dimethyl-aminoacetate, ethanol and other alcohols, Azone® and derivatives, ethyl acetate and related esters, beta-cyclodextrin or other cyclodextrins, alcohol, and/or isopropyl alcohol.

In another embodiment, the pre-treatment composition includes a freezing point depressant and, optionally, additional adjuvants, for facilitating preservation of non-targeted tissue at the treatment site. For example, the pre-treatment composition can include a freezing point depressant (e.g., propylene glycol) and an alcohol (e.g., isopropyl alcohol). In various embodiments, the pre-treatment composition can also include at least one of a thickening agent, a pH buffer, a humectant and a surfactant, and can further include at least one of (a) an adjuvant configured to increase permeation of the freezing point depressant through a stratum corneum of the skin, (b) a solute configured to increase an effective concentration of the solute in an intracellular fluid or an extracellular fluid in the target region, (c) a hydrophilic molecule, and (d) a lipophobic molecule. In a particular embodiment, the pre-treatment composition includes about 40% propylene glycol, about 30% isopropyl alcohol and about 30% water.

In other embodiments, pre-treatment and/or post-treatment compositions can be provided to increase actual or a subject's perception of efficacy associated with a cooling treatment for aesthetic benefit. For example, a pre-treatment or post-treatment composition can include an anesthetic (e.g., benzocaine, lidocaine, butamben, pramoxine, tetracaine), cosmeceuticals (e.g., *Daucus carota sativa* extract, perfluorodecalin, perfluoro-n-octane), skin conditioners (e.g., squalene, dimethicone, divinyldimethicone, silsesquioxane crosspolymer and related compounds), anti-aging pro-collagen elements (e.g., glycolic acid, superoxide dismutase, niacinimide), fragrances, etc. In other embodiments, a pre-treatment or post-treatment composition can include menthyl lactate or related compounds that may enhance or promote vasoconstriction and/or impart a cooling sensation.

In various embodiments, pre-treatment and/or post-treatment compositions can be used in combination with other aspects of the technology described herein. For example, a pre-treatment composition can be administered either during or before performing the methods 600 or 700. Likewise, post-treatment compositions can be administered at the conclusion of any treatment for removing heat from a treatment site to selectively affect lipid-rich cells.

In many embodiments, a series of substances can be applied to the target region during the course of a treatment. For example, a first substance can be a pre-treatment composition, second and third substances can include a first cryoprotectant applied prior to heat removal from the target region and a second cryoprotectant applied to the target region (e.g., in conjunction with the applicator) during the heat removal/cooling portion of the treatment. A fourth substance can be applied to the target region following the cooling process. Such a substance can be a post-treatment formulation. In particular, various treatments can include the application of one or more substances applied in series and/or, in other embodiments, simultaneously, to facilitate protection of non-targeted tissue and/or for tissue recovery post-treatment. Each substance can be adapted to (1) enhance the delivery or effect of a subsequently applied substance, (2) enhance the effect of cryotherapy, (3) reduce treatment times, and/or (4) reduce adverse effects of cryotherapy. In certain embodiments, the substances may include compositions having the same or at least similar formulations. For example, the application of a second substance may be simply the re-application or replenishment of the first substance. In other embodiments, the substances applied in series may comprise different compositions. In such embodiments, the earlier applied substances may be wiped or cleaned from the surface of the skin at the treatment site prior to application of the next substance to be applied in series. In other embodiments, the later-applied substance(s) can be added to remaining earlier-applied substances at the surface of the skin.

The system 100 (FIG. 1) can be used to perform several pre-treatment and treatment methods. Although specific examples of methods are described herein, one skilled in the art is capable of identifying other methods that the system could perform. Moreover, the methods described herein can be altered in various ways. As examples, the order of illustrated logic may be rearranged, sub-stages may be performed in parallel, illustrated logic may be omitted, other logic may be included, etc.

G. Treatment Examples

Example 1: Effect of Pre-Treating a Treatment Site with Mechanical Stimulation Prior to Cooling Treatment This section describes an example of the clinical use of pre-treating the skin of a patient at a treatment site with mechanical stimulation in the presence of topically applied cryoprotectant prior to applying cooling treatment for affecting subcutaneous lipid-rich cells. Additional embodiments of the present technology may be practiced with features similar to or different than those described with respect to this example. Among other features of the present technology, this example illustrates that mechanical stimulation in the presence of cryoprotectant prior to cooling treatment may have utility in the prevention of freezing events or damage when cooling subcutaneous lipid-rich tissue for aesthetic or health-related reasons.

Thirteen patients scheduled for abdominoplasty where offered to undergo a CoolSculpting® treatment on abdominal treatment sites. Each patient underwent two CoolSculpting® treatment sessions having a 60 minute cycle time and a −15° C. applicator temperature set point. The vacuum was set at 60 per typical recommended settings and a standard CoolSculpting® gel pad and liner were used per instructions. Six patients were assigned to a control group and had no pre-treatment performed prior to the CoolSculpting® treatment. Seven patients were pre-treated using mechanical stimulation prior to the CoolSculpting® treatment. The pre-treatment protocol included (a) applying 3 cc of cryoprotectant containing 100% propylene glycol (PG), (b) manually spreading the cryoprotectant over the surface of the skin using a gloved hand, (c) mildly brushing the cryoprotectant and skin at the treatment site using a cosmetic brush with rotating bristles for 2 minutes. Following the pre-treatment protocol, pre-treated patients and control patients began CoolSculpting® treatment with placement of a gel pad over the treatment site followed by placement of a vacuum CoolCore® applicator. Freeze events were detected using a freeze detection algorithm such as that described in U.S. Pat. No. 8,285,390. The results are as follows:

TABLE 1

Clinical Detection of Freeze Events for Abdominal CoolSculpting® Patients With and Without Pre-Treatment of Mechanical Stimulation

|  | Pre-Treatment using 100% PG for 2 minutes | Control |
| --- | --- | --- |
| Total Cycles @ −15° C. | 14 | 12 |
| Freeze Events | 0 | 5 |
| Probability of Freeze Event | 0% | 42% |

In the control group of patients, three patients experienced a total of five freeze events at −15° C. The pre-treated group of patients did not experience any freeze events at −15° C. In a further control group, three patients underwent six cycles of CoolSculpting® treatment with an applicator temperature of −13° C. and without pre-treatment. No freeze events occurred at the −13° C. treatment temperature.

The findings suggest that mechanical stimulation of the skin in the presence of cryoprotectant prior to cooling treatment can facilitate lowering the treatment temperature during the cooling treatment. Without being bound by theory, it is believed that mechanical stimulation pre-treatment enhances uptake of the cryoprotectant in the tissue susceptible of freeze events (e.g., the dermal and epidermal skin layers). It is further believed that lowering the treatment temperature of the cooling treatment can have one or more advantages such as decreasing a cycle time while achieving similar benefit, decreasing variability in treatment results between patients, increasing consistent freezing of deeper adipose tissue which could provide better treatment results.

Example 2: Pre-Treatment of a Treatment Site with a Pre-Treatment Composition Followed by Cooling Treatment This section describes an example of the clinical use of pre-treating the skin of a patient at a treatment site with a topically applied pre-treatment composition prior to applying cooling treatment for affecting targeted cells. Additional embodiments of the present technology may be practiced with features similar to or different than those described with respect to this example. Among other features of the present technology, this example describes the use of topically-applied pre-treatment compositions prior to cooling treatment, which may have utility in the prevention of freezing events or damage when cooling targeted tissue for aesthetic or health-related reasons.

In this example, and in clinical or other treatment settings, a pre-treatment composition is rubbed (e.g., spread, abraded, dispersed, etc.) onto the skin by a clinician for about 30 to about 45 seconds with a mild abrasive cloth (e.g., a nonwoven textured cloth wipe). The pre-treatment composition comprises about 30% isopropyl alcohol and/or an adjuvant for increasing permeability of the skin at the treatment site. The pre-treatment composition also comprises about 40% propylene glycol and about 30% water. The application of the pre-treatment composition in this manner can allow the propylene glycol (e.g., freezing point depressant) to permeate the skin.

Following application of the pre-treatment composition as described, and without removing the pre-treatment composition, the clinician applies the system applicator having a liner with cryoprotectant pre-loaded within the liner to the surface of the skin at the treatment site. Certain examples may include steps for removing the pre-treatment composition prior to positioning the applicator. The cryoprotectant comprises about 40% propylene glycol and about 60% water. In other examples, the cryoprotectant can be about 50% propylene glycol and about 50% water, or about 60% propylene glycol and about 40% water. Following positioning of the cryoprotectant-loaded applicator, heat can be removed transdermally from the target region. The heat removal process can last approximately 30 minutes to about 120 minutes. Other time intervals are also contemplated. In certain instances, the applicator and/or cryoprotectant can be pre-heated (e.g., to about 26° C., greater than about 26° C., etc.), for example, to facilitate attachment of the liner to the applicator. Warming of the applicator and/or treatment site may increase the cooling treatment time slightly beyond that otherwise needed when no preheat is used. Typical cooling treatment times are approximately 30 minutes to approximately 120 minutes.

Without being bound by theory, it is believed that the clinical use of pre-treatment compositions enhances uptake of the cryoprotectant in the tissue susceptible of freeze events (e.g., the dermal and epidermal skin layers). It is further believed that lowering the treatment temperature of the cooling treatment can have one or more advantages such as decreasing a cycle time while achieving similar benefit, decreasing variability in treatment results between patients, increasing consistent freezing of deeper adipose tissue which could provide better treatment results.

H. Suitable Computing Environments

Figure 8:
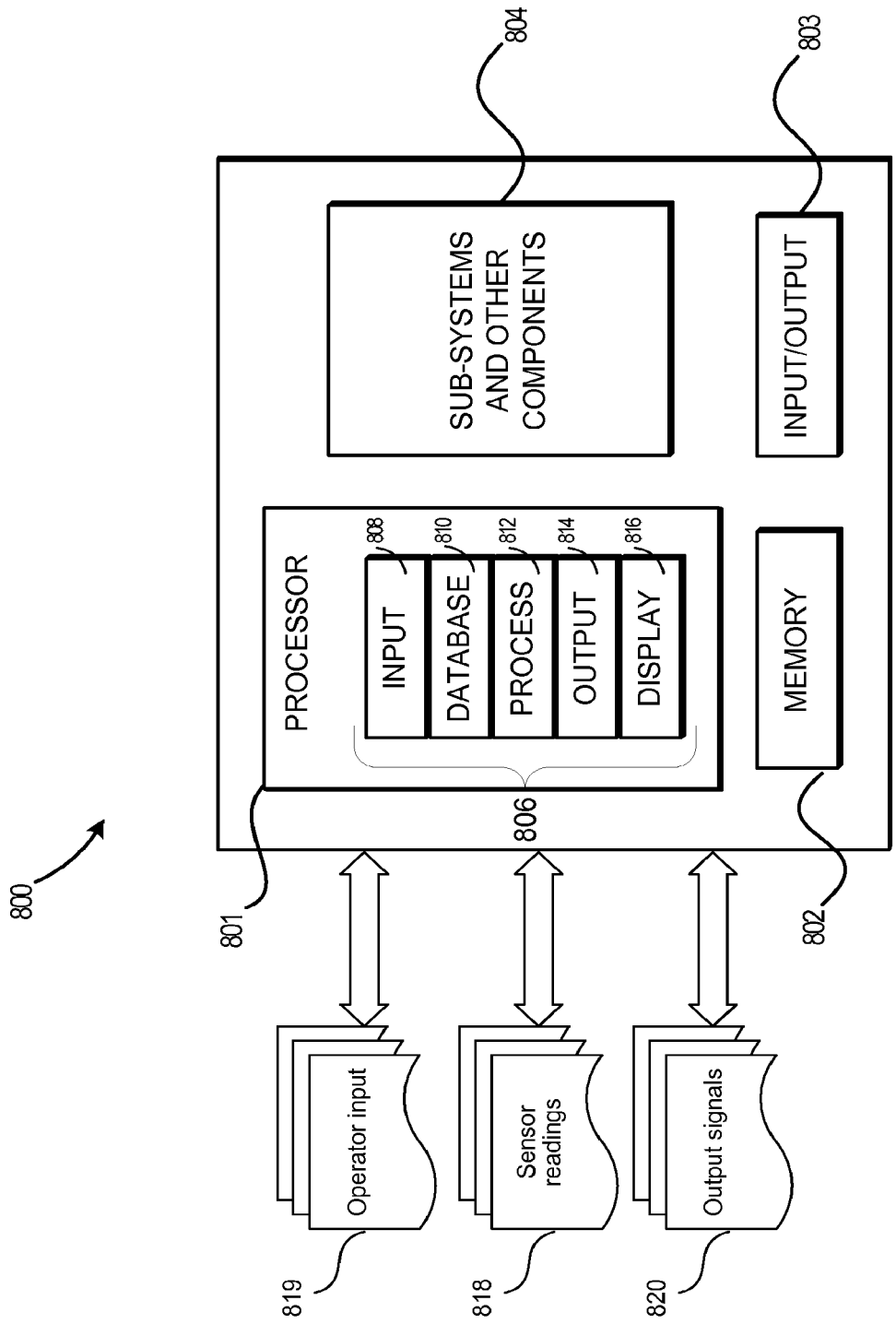
FIG. 8 is a schematic block diagram illustrating computing system software modules and subcomponents of a computing device suitable to be used in the system of FIG. 1 in accordance with an embodiment of the technology.

FIG. 8 is a schematic block diagram illustrating subcomponents of a computing device 800 in accordance with an embodiment of the disclosure. The computing device 800 can include a processor 801, a memory 802 (e.g., SRAM, DRAM, flash, or other memory devices), input/output devices 803, and/or subsystems and other components 804. The computing device 800 can perform any of a wide variety of computing processing, storage, sensing, imaging, and/or other functions. Components of the computing device 800 may be housed in a single unit or distributed over multiple, interconnected units (e.g., though a communications network). The components of the computing device 800 can accordingly include local and/or remote memory storage devices and any of a wide variety of computer-readable media.

As illustrated in FIG. 8, the processor 801 can include a plurality of functional modules 806, such as software modules, for execution by the processor 801. The various implementations of source code (i.e., in a conventional programming language) can be stored on a computer-readable storage medium or can be embodied on a transmission medium in a carrier wave. The modules 806 of the processor can include an input module 808, a database module 810, a process module 812, an output module 814, and, optionally, a display module 816.

In operation, the input module 808 accepts an operator input 819 via the one or more input devices described above with respect to FIG. 1, and communicates the accepted information or selections to other components for further processing. The database module 810 organizes records, including patient records, treatment data sets, treatment profiles and operating records and other operator activities, and facilitates storing and retrieving of these records to and from a data storage device (e.g., internal memory 802, an external database, etc.). Any type of database organization can be utilized, including a flat file system, hierarchical database, relational database, distributed database, etc.

In the illustrated example, the process module 812 can generate control variables based on sensor readings 818 from sensors (e.g., the temperature measurement components 217 and 227 of FIG. 2) and/or other data sources, and the output module 814 can communicate operator input to external computing devices and control variables to the controller 114 (FIG. 1). The display module 816 can be configured to convert and transmit processing parameters, sensor readings 818, output signals 820, input data, treatment profiles and prescribed operational parameters through one or more connected display devices, such as a display screen, printer, speaker system, etc. A suitable display module 816 may include a video driver that enables the controller 114 to display the sensor readings 818 or other status of treatment progression on the output device 120 (FIG. 1).

In various embodiments, the processor 801 can be a standard central processing unit or a secure processor. Secure processors can be special-purpose processors (e.g., reduced instruction set processor) that can withstand sophisticated attacks that attempt to extract data or programming logic. The secure processors may not have debugging pins that enable an external debugger to monitor the secure processor's execution or registers. In other embodiments, the system may employ a secure field programmable gate array, a smartcard, or other secure devices.

The memory 802 can be standard memory, secure memory, or a combination of both memory types. By employing a secure processor and/or secure memory, the system can ensure that data and instructions are both highly secure and sensitive operations such as decryption are shielded from observation.

Suitable computing environments and other computing devices and user interfaces are described in commonly assigned U.S. Pat. No. 8,275,442, entitled "TREATMENT PLANNING SYSTEMS AND METHODS FOR BODY CONTOURING APPLICATIONS," which is incorporated herein in its entirety by reference.

I. Conclusion

Various embodiments of the technology are described above. It will be appreciated that details set forth above are provided to describe the embodiments in a manner sufficient to enable a person skilled in the relevant art to make and use the disclosed embodiments. Several of the details and advantages, however, may not be necessary to practice some embodiments. Additionally, some well-known structures or functions may not be shown or described in detail, so as to avoid unnecessarily obscuring the relevant description of the various embodiments. Although some embodiments may be within the scope of the technology, they may not be described in detail with respect to the Figures. Furthermore, features, structures, or characteristics of various embodiments may be combined in any suitable manner. Moreover, one skilled in the art will recognize that there are a number of other technologies that could be used to perform functions similar to those described above. While processes or blocks are presented in a given order, alternative embodiments may perform routines having stages, or employ systems having blocks, in a different order, and some processes or blocks may be deleted, moved, added, subdivided, combined, and/or modified. Each of these processes or blocks may be implemented in a variety of different ways. Also, while processes or blocks are at times shown as being performed in series, these processes or blocks may instead be performed in parallel, or may be performed at different times. The headings provided herein are for convenience only and do not interpret the scope or meaning of the described technology.

The terminology used in the description is intended to be interpreted in its broadest reasonable manner, even though it is being used in conjunction with a detailed description of identified embodiments.

Unless the context clearly requires otherwise, throughout the description, the words "comprise," "comprising," and the like are to be construed in an inclusive sense as opposed to an exclusive or exhaustive sense; that is to say, in a sense of "including, but not limited to." Words using the singular or plural number also include the plural or singular number, respectively. Use of the word "or" in reference to a list of two or more items covers all of the following interpretations of the word: any of the items in the list, all of the items in the list, and any combination of the items in the list. Furthermore, the phrase "at least one of A, B, and C, etc." is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.).

Some of the functional units described herein have been labeled as modules, in order to more particularly emphasize their implementation independence. For example, modules (e.g., modules discussed in connection with FIG. 8) may be implemented in software for execution by various types of processors. An identified module of executable code may, for instance, comprise one or more physical or logical blocks of computer instructions which may, for instance, be organized as an object, procedure, or function. The identified blocks of computer instructions need not be physically located together, but may comprise disparate instructions stored in different locations which, when joined logically together, comprise the module and achieve the stated purpose for the module.

A module may also be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

A module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network.

Any patents, applications and other references cited herein, are incorporated herein by reference. Aspects of the described technology can be modified, if necessary, to employ the systems, functions, and concepts of the various references described above to provide yet further embodiments.

These and other changes can be made in light of the above Detailed Description. While the above description details certain embodiments and describes the best mode contemplated, no matter how detailed, various changes can be made. Implementation details may vary considerably, while still being encompassed by the technology disclosed herein. As noted above, particular terminology used when describing certain features or aspects of the technology should not be taken to imply that the terminology is being redefined herein to be restricted to any specific characteristics, features, or aspects of the technology with which that terminology is associated.

What is claimed is:

1. A method for cooling a subcutaneous tissue region of a human subject having skin, the method comprising:
    applying a cryoprotectant to a surface of the skin, wherein the cryoprotectant has a viscosity greater than 5,000 cP at a temperature below 5° C.; and
    cooling the subcutaneous tissue region of the human subject having skin using an applicator while the cryoprotectant is absorbed into the skin and the subcutaneous tissue region is lowered to a temperature below 5° C.

2. The method of claim 1, wherein the cryoprotectant adheres to a temperature-controlled surface of the applicator when cooled by the applicator.

3. The method of claim 1, further comprising spreading the cryoprotectant along subject's skin prior to cooling the subcutaneous tissue region to the temperature below 5° C.

4. The method of claim 1, wherein the cryoprotectant has a viscosity greater than 10,000 cP at a temperature below 5° C.

5. The method of claim 1, wherein the cryoprotectant includes at least one thickening agent that causes the cryoprotectant to have a viscosity greater than 10,000 cP at a temperature lower than 5° C.

6. The method of claim 1, wherein a sufficient amount of cryoprotectant is applied such that the cryoprotectant is continuously absorbed into the skin for a time period of at least 15 minutes.

7. The method of claim 1, further comprising continuously supplying the cryoprotectant to the skin during heat removal from the subcutaneous tissue region.

8. The method of claim 1, further comprising continuously supplying the cryoprotectant to the skin while removing heat from the subcutaneous tissue region.

9. The method of claim 1, further comprising applying a pre-treatment composition to a surface of the skin prior to cooling the subcutaneous tissue region.

10. A method for cooling a subcutaneous tissue region of a human subject having skin, the method comprising:
  applying an applicator to the subject's skin; and
  cooling, using the applicator, the subcutaneous tissue region while a cryoprotectant is absorbed into the skin underlying the applicator and the subcutaneous tissue region is at a temperature below 5° C., wherein the cryoprotectant has a viscosity greater than 5,000 cP at a temperature below 5° C.

11. The method of claim 10, wherein the cryoprotectant adheres to a temperature-controlled surface of the applicator when cooled by the applicator.

12. The method of claim 10, further comprising applying the cryoprotectant to a cooling surface of the applicator.

13. The method of claim 10, wherein the cryoprotectant has a viscosity greater than 10,000 cP at a temperature between 0° C. to about −15° C.

14. The method of claim 10, wherein the cryoprotectant includes at least one thickening agent that causes the cryoprotectant to have a viscosity greater than 10,000 cP at a temperature lower than 5° C.

* * * * *